US010363116B2

(12) United States Patent
Boronkay

(10) Patent No.: US 10,363,116 B2
(45) Date of Patent: Jul. 30, 2019

(54) DIRECT FABRICATION OF POWER ARMS

(71) Applicant: ALIGN TECHNOLOGY, INC., San Jose, CA (US)

(72) Inventor: Allen Boronkay, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 155 days.

(21) Appl. No.: 15/202,299

(22) Filed: Jul. 5, 2016

(65) Prior Publication Data

US 2017/0007363 A1   Jan. 12, 2017

Related U.S. Application Data

(60) Provisional application No. 62/189,291, filed on Jul. 7, 2015, provisional application No. 62/189,312, filed on Jul. 7, 2015, provisional application No. 62/189,317, filed on Jul. 7, 2015.

(51) Int. Cl.

| | |
|---|---|
| *A61C 7/00* | (2006.01) |
| *A61C 7/08* | (2006.01) |
| *A61C 7/36* | (2006.01) |
| *A61C 7/10* | (2006.01) |
| *A61C 7/14* | (2006.01) |
| *B33Y 50/02* | (2015.01) |
| *B33Y 80/00* | (2015.01) |
| *G05B 19/4097* | (2006.01) |
| *G05B 19/042* | (2006.01) |

(Continued)

(52) U.S. Cl.
CPC ............... *A61C 7/002* (2013.01); *A61C 7/08* (2013.01); *A61C 7/10* (2013.01); *A61C 7/14* (2013.01); *A61C 7/146* (2013.01); *A61C 7/36* (2013.01); *B33Y 50/02* (2014.12); *B33Y 80/00* (2014.12); *G05B 15/02* (2013.01); *G05B 19/042* (2013.01); *G05B 19/4097* (2013.01); *B29L 2031/753* (2013.01); *B29L 2031/7532* (2013.01); *G05B 2219/2647* (2013.01); *G05B 2219/35134* (2013.01); *G05B 2219/49007* (2013.01)

(58) Field of Classification Search
CPC ....... A61C 19/063; A61C 19/066; A61C 7/00; A61C 7/002; A61C 7/008
USPC ....................................................... 433/6, 7
See application file for complete search history.

(56) References Cited

U.S. PATENT DOCUMENTS

| | | | |
|---|---|---|---|
| 2,467,432 A | 4/1949 | Kesling | |
| 3,407,500 A | 10/1968 | Kesling | |
| 3,600,808 A | 8/1971 | Reeve | |

(Continued)

FOREIGN PATENT DOCUMENTS

| | | | |
|---|---|---|---|
| AU | 3031677 A | 5/1979 | |
| AU | 517102 B2 | 7/1981 | |

(Continued)

OTHER PUBLICATIONS

International search report and written opinion dated Nov. 23, 2016 for PCT Application No. PCT/US2016/041391.

(Continued)

*Primary Examiner* — Wade Miles
*Assistant Examiner* — Matthew P Saunders
(74) *Attorney, Agent, or Firm* — Wilson Sonsini Goodrich & Rosati

(57) ABSTRACT

Systems, methods, and devices for improved orthodontic treatment of a patient's teeth are provided herein.

10 Claims, 33 Drawing Sheets

(51) Int. Cl.
    *G05B 15/02*  (2006.01)
    *B29L 31/00*  (2006.01)

(56) References Cited

U.S. PATENT DOCUMENTS

| | | |
|---|---|---|
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,272,240 A | 6/1981 | Glassman |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,450,807 B1 | 9/2002 | Chishti et al. |
| 6,471,511 B1 | 10/2002 | Chishti et al. |
| 6,482,298 B1 | 11/2002 | Bhatnagar |
| 6,524,101 B1 | 2/2003 | Phan et al. |
| 6,554,611 B2 | 4/2003 | Shishti et al. |
| 6,572,372 B1 | 6/2003 | Phan et al. |
| 6,629,840 B2 | 10/2003 | Chishti et al. |

(56) References Cited

U.S. PATENT DOCUMENTS

| | | |
|---|---|---|
| 6,705,863 B2 | 3/2004 | Phan et al. |
| 6,722,880 B2 | 4/2004 | Chishti et al. |
| 6,749,414 B1 | 6/2004 | Hanson et al. |
| 6,830,450 B2 | 12/2004 | Knopp et al. |
| 7,077,646 B2 | 7/2006 | Hilliard et al. |
| 7,553,157 B2 | 6/2009 | Abolfathi et al. |
| 7,658,610 B2 | 2/2010 | Knopp |
| 7,878,801 B2 | 2/2011 | Abolfathi et al. |
| 7,892,474 B2 | 2/2011 | Shkolnik et al. |
| 8,439,672 B2 | 5/2013 | Matov et al. |
| 8,439,674 B2 | 5/2013 | Li et al. |
| 8,444,412 B2 | 5/2013 | Baughman et al. |
| 8,641,414 B2 | 2/2014 | Borovinskih et al. |
| 8,758,009 B2 | 6/2014 | Chen et al. |
| 8,899,976 B2 | 12/2014 | Chen et al. |
| 9,144,512 B2 | 9/2015 | Wagner |
| 9,408,743 B1 | 8/2016 | Wagner |
| 9,439,802 B2 | 9/2016 | Wagner et al. |
| 9,445,938 B1 | 9/2016 | Wagner |
| 9,808,327 B1 | 11/2017 | Kim et al. |
| 2001/0041320 A1 | 11/2001 | Phan et al. |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer |
| 2004/0067463 A1* | 4/2004 | Rosenberg ............... A61C 7/12 433/6 |
| 2004/0128010 A1 | 7/2004 | Pavlovskaia et al. |
| 2005/0055118 A1 | 3/2005 | Nikolskiy et al. |
| 2005/0186524 A1 | 8/2005 | Abolfathi et al. |
| 2006/0248749 A1 | 11/2006 | Ellis et al. |
| 2007/0065768 A1* | 3/2007 | Nadav .................... A61C 7/006 433/6 |
| 2007/0231765 A1 | 10/2007 | Phan et al. |
| 2008/0268400 A1 | 10/2008 | Moss et al. |
| 2010/0006111 A1 | 1/2010 | Spiridigliozzi et al. |
| 2010/0092905 A1 | 4/2010 | Martin |
| 2010/0119996 A1 | 5/2010 | Kaigler, Sr. et al. |
| 2010/0129763 A1 | 5/2010 | Kuo |
| 2010/0138025 A1 | 6/2010 | Morton et al. |
| 2011/0027743 A1 | 2/2011 | Cinader, Jr. et al. |
| 2011/0269092 A1 | 11/2011 | Kuo et al. |
| 2011/0281229 A1 | 11/2011 | Abolfathi |
| 2012/0058443 A1 | 3/2012 | Tamura et al. |
| 2012/0129117 A1* | 5/2012 | McCance ................ A61C 7/10 433/7 |
| 2013/0089828 A1* | 4/2013 | Borovinskih ............ A61C 7/08 433/6 |
| 2013/0095446 A1* | 4/2013 | Andreiko ................ A61C 7/08 433/6 |
| 2013/0122448 A1 | 5/2013 | Kitching et al. |
| 2013/0183630 A1 | 7/2013 | Krikorian et al. |
| 2013/0209952 A1 | 8/2013 | Kuo et al. |
| 2013/0266907 A1 | 10/2013 | Lopes et al. |
| 2013/0323665 A1 | 12/2013 | Dinh et al. |
| 2014/0061974 A1 | 3/2014 | Tyler |
| 2014/0363779 A1* | 12/2014 | Kopelman ............... A61C 7/08 433/6 |
| 2015/0097315 A1 | 4/2015 | Desimone et al. |
| 2015/0097316 A1 | 4/2015 | Desimone et al. |
| 2015/0102532 A1 | 4/2015 | Desimone et al. |
| 2015/0157421 A1* | 6/2015 | Martz ..................... A61C 7/08 433/6 |
| 2015/0216627 A1* | 8/2015 | Kopelman ............... A61C 7/08 433/6 |
| 2016/0081768 A1 | 3/2016 | Kopelman et al. |
| 2016/0100917 A1 | 4/2016 | Howe et al. |
| 2016/0199216 A1 | 7/2016 | Cam et al. |
| 2016/0256240 A1 | 9/2016 | Shivapuja et al. |
| 2016/0288412 A1 | 10/2016 | Stampfl et al. |
| 2016/0367394 A1 | 12/2016 | Wagner |
| 2017/0007359 A1 | 1/2017 | Kopelman et al. |
| 2017/0007361 A1 | 1/2017 | Boronkay |
| 2017/0007362 A1 | 1/2017 | Chen et al. |
| 2017/0007363 A1 | 1/2017 | Boronkay |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0007386 A1 | 1/2017 | Mason |
| 2017/0008333 A1 | 1/2017 | Mason |
| 2017/0056138 A1 | 3/2017 | Zandinejad et al. |
| 2018/0071057 A1 | 3/2018 | Rudman et al. |
| 2018/0153643 A1 | 6/2018 | Lambert et al. |
| 2018/0168776 A1 | 6/2018 | Webber et al. |
| 2018/0215091 A1 | 8/2018 | Einav et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 2581062 A2 | 4/2013 |
| ES | 463897 A1 | 1/1980 |
| FR | 2369828 A1 | 6/1978 |
| FR | 2652256 A1 | 3/1991 |
| GB | 1550777 A | 8/1979 |
| GB | 15500777 | 8/1979 |
| JP | S5358191 A | 5/1978 |
| JP | H0428359 A | 1/1992 |
| JP | 08508174 | 9/1996 |
| JP | H08508174 A | 9/1996 |
| JP | 2013063243 A | 4/2013 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-0032132 A1 | 6/2000 |
| WO | WO-2006096558 A2 | 9/2006 |

OTHER PUBLICATIONS

AADR. American Association for Dental Research, Summary of Activities, Mar. 20-23,1980, Los Angeles, CA, p. 195.

Alcaniz, et al, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

(56) References Cited

OTHER PUBLICATIONS

Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL< http://astronomy.swin.edu.au/-pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).
Carbon3D. Clip Technology. A new approach to 3D printing. 2015. http://carbon3d.com/ Accessed Jul. 1, 2015.
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Composite material. Wikipedia. Last modified Jun. 22, 2015. https://en.wikipedia.org/wiki/Composite_material.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside, Part 2 F. Duret—A Man with a Vision, Part 3 The Computer Gives New Vision—Literally, Part 4 Bytes 'N Bites—The Computer Moves from the Front Desk to the Operatory," Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for gingiva. Dictionary.com p. 1-3. Retrieved from the internet Nov. 5, 2004<http://reference.com/search/search?q= gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Desimone. What if 3D printing was 100% faster? TEDtalk. Mar. 2015. http://www.ted.com/talks/joe_desimone_what_if3d_printing_was_25x_faster.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese lnformatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet<http://wscg.zcu.cz/wscg98/papers98/Strasser 98.pdf>, 8 pages.

(56) References Cited

OTHER PUBLICATIONS

Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottlieb et al., "JCO Interviews Dr. James A. McNamura, Jr., on the Frankel Appliance: Part 2: Clinical 1-1 Management,"J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Halterman. A path to the future—continuous composite 3D printing. Nov. 12, 2014. http://www.3dprinterworld.com/article/path-future-continuous-composite-3d-printing.
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hipolite. Helios One 3D Printer—New Heliolithography Technology Could Eventually Replace SLA and FDM. Jul. 2, 2014. http://3dprint.com/7958/orange-maker-helio-one-3d/ .
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Objet Geometries. Wikipedia. Last modified Jul. 17, 2014 https://en.wikipedia.org/wiki/Objet_Geometries.
Orange Maker. High resolution 3D printing technology. 2015. http://www.orangemaker.com/. Accessed Jul. 1, 2015.
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www.essix.com/magazine/defaulthtml> Aug. 13, 1997.
Rapid prototyping. Protosys Technologies. 2005. http://www.protosystech.com/rapid-prototyping.htm. Accessed Jul. 1, 2015.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

(56) References Cited

OTHER PUBLICATIONS

Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Orange Maker Spins the Plate to Make Better 3D Prints. Newloop Tech and Gadgets. YouTube. Jul. 11, 2014. https://www.youtube.com/watch?v=MpzPWURWfZk.
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: the Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: the Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method

(56) References Cited

OTHER PUBLICATIONS and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances-Pro Lab product information for patients, 2 pages (2002).
The 7 Categories of Additive Manufacturing Website: http://www.lboro.ac.uk/research/annrg/about/the7categoriesofadditivemanufacturing/ Published: Mar. 15, 2015 (Year: 2015).

* cited by examiner

Buccal ←→ Lingual

Mesial ←→ Distal

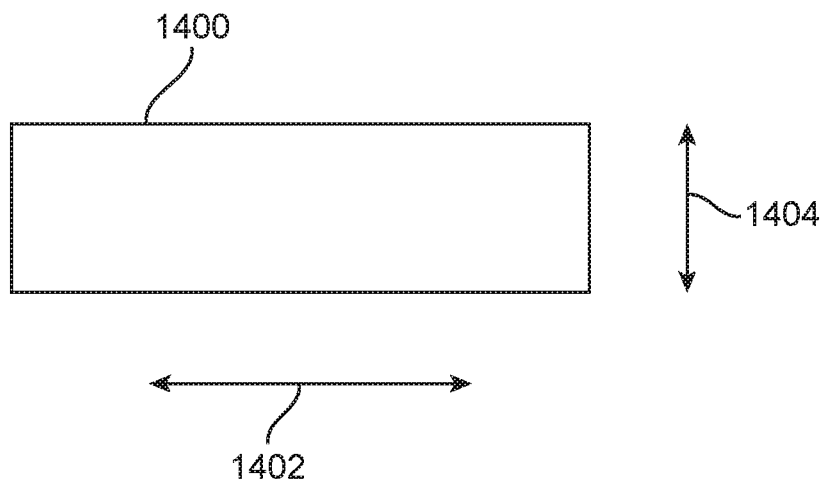
FIG. 14A
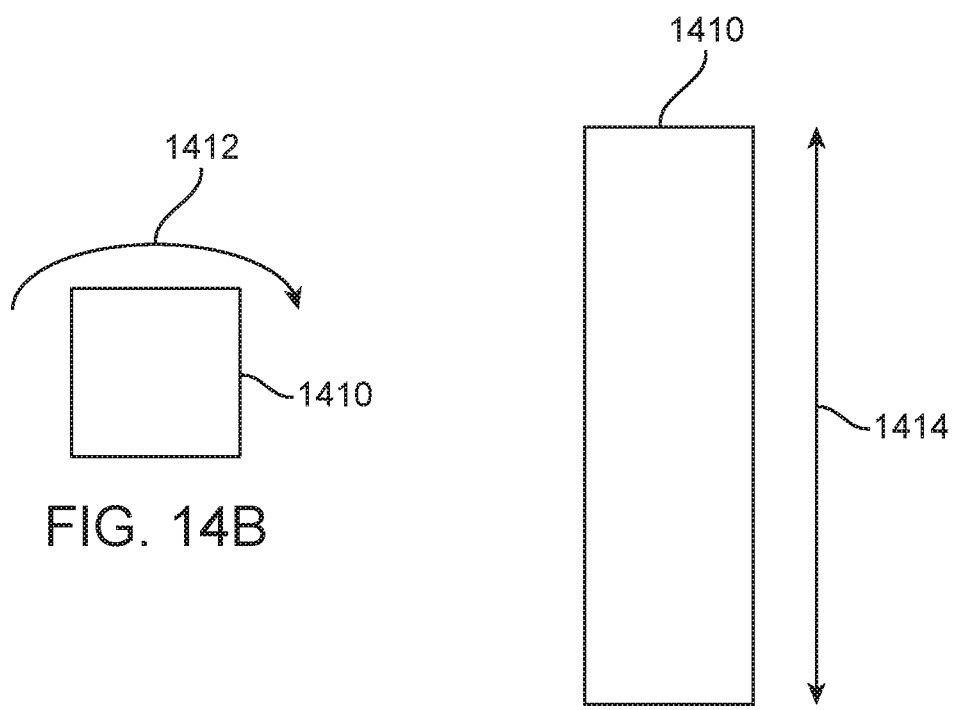
FIG. 14B
FIG. 14C

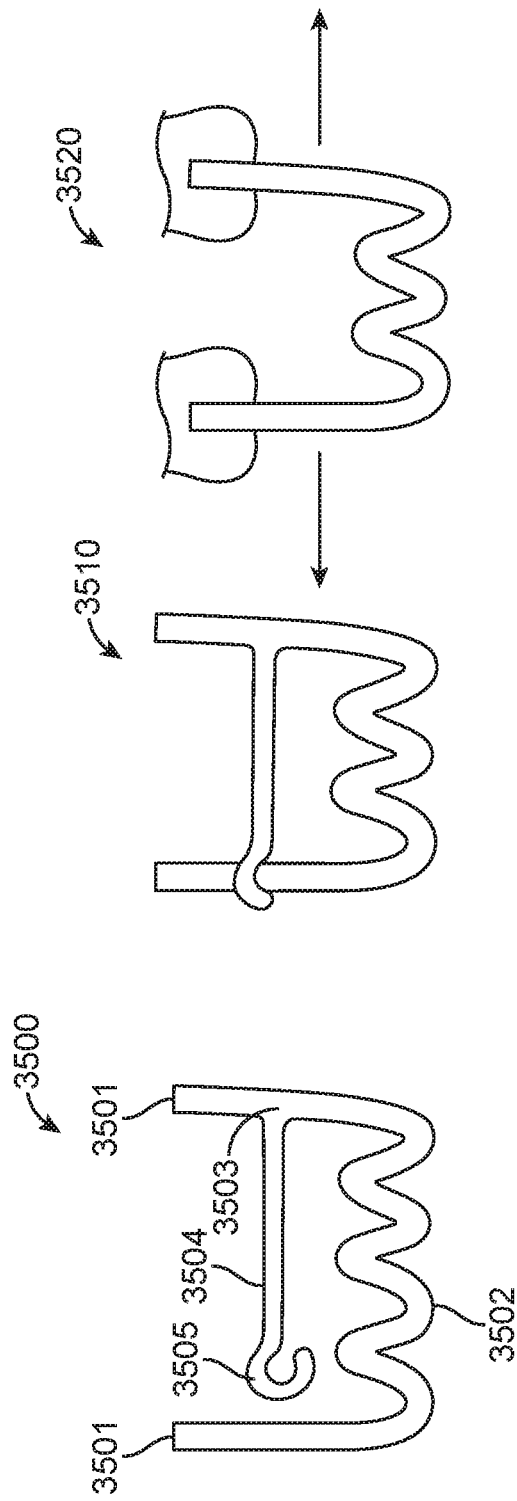

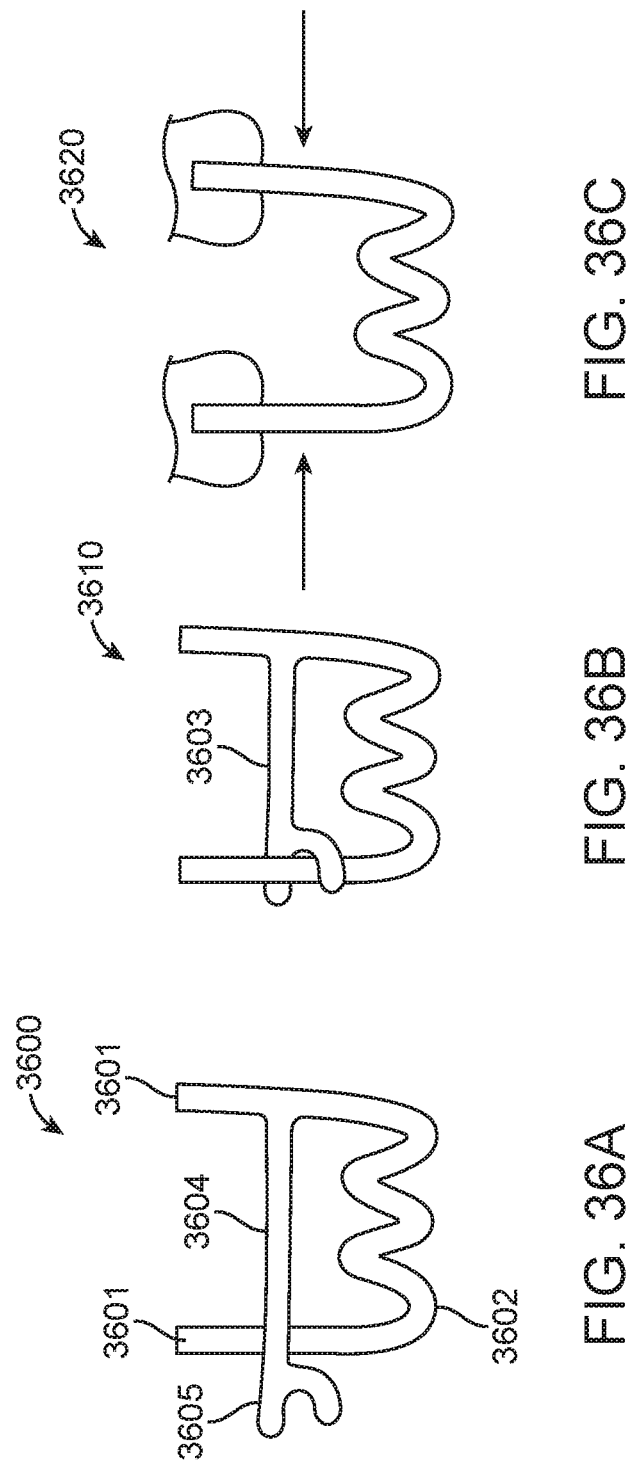

DIRECT FABRICATION OF POWER ARMS

CROSS-REFERENCE

This application claims the benefit of U.S. Provisional Application No. 62/189,291, filed Jul. 7, 2015, U.S. Provisional Application No. 62/189,312, filed Jul. 7, 2015, and U.S. Provisional Application No. 62/189,317, filed Jul. 7, 2015, the disclosures of each of which are incorporated herein by reference in their entirety.

The subject matter of the following co-pending patent applications is related to the present application: U.S. application Ser. No. 15/202,342, filed Jul. 5, 2016, entitled "MULTI-MATERIAL ALIGNERS", which claims the benefit of U.S. Provisional Application No. 62/189,259, filed Jul. 7, 2015 and U.S. Provisional Application No. 62/189,282, filed Jul. 7, 2015; U.S. application Ser. No. 15/202,472, filed Jul. 5, 2016, entitled "DIRECT FABRICATION OF ALIGNERS WITH INTERPROXIMAL FORCE COUPLING", which claims the benefit of U.S. Provisional Application No. 62/189,263, filed Jul. 7, 2015; U.S. application Ser. No. 15/202,452, filed Jul. 5, 2016, entitled "DIRECT FABRICATION OF ALIGNERS FOR ARCH EXPANSION", which claims the benefit of U.S. Provisional Application No. 62/189,271, filed Jul. 7, 2015, and U.S. Provisional Application No. 62/189,301, filed Jul. 7, 2015; U.S. application Ser. No. 15/202,348, filed Jul. 5, 2016, entitled "DIRECT FABRICATION OF ATTACHMENT TEMPLATES WITH ADHESIVE", which claimed the benefit of U.S. Provisional Application No. 62/189,259, filed Jul. 7, 2015 and U.S. Provisional Application No. 62/189,282, filed Jul. 7, 2015; U.S. application Ser. No. 15/202,467, filed Jul. 5, 2016, entitled "DIRECT FABRICATION CROSSLINKING FOR PALATE EXPANSION AND OTHER APPLICATIONS", which claims the benefit of U.S. Provisional Application No. 62/189,301, filed Jul. 7, 2015, and U.S. Provisional Application No. 62/189,271, filed Jul. 7, 2015; U.S. application Ser. No. 15/202,254, filed Jul. 5, 2016, entitled "SYSTEMS, APPARATUSES AND METHODS FOR DENTAL APPLIANCES WITH INTEGRALLY FORMED FEATURES", which claims the benefit of U.S. Provisional Application No. 62/189,291, filed Jul. 7, 2015, U.S. Provisional Application No. 62/189,312, filed Jul. 7, 2015, and U.S. Provisional Application No. 62/189,317, filed Jul. 7, 2015; U.S. application Ser. No. 15/202,187, filed Jul. 5, 2016, entitled "DIRECT FABRICATION OF ORTHODONTIC APPLIANCES WITH VARIABLE PROPERTIES", which claims the benefit of U.S. Provisional Application No. 62/189,291, filed Jul. 7, 2015, U.S. Provisional Application No. 62/189,312, filed Jul. 7, 2015, and U.S. Provisional Application No. 62/189,317, filed Jul. 7, 2015; U.S. application Ser. No. 15/202,139, filed Jul. 5, 2016, entitled "SYSTEMS, APPARATUSES AND METHODS FOR SUBSTANCE DELIVERY FROM DENTAL APPLIANCE, which claims the benefit of U.S. Provisional Application No. 62/189,303, filed Jul. 7, 2015; U.S. Application Ser. No. 62/189,303, filed Jul. 5, 2016, entitled "DENTAL MATERIALS USING THERMOSET POLYMERS", which claims the benefit of U.S. Provisional Application No. 62/189,380, filed Jul. 7, 2015; and U.S. application Ser. No. 15/202,083, filed Jul. 5, 2016, entitled "DENTAL APPLIANCE HAVING ORNAMENTAL DESIGN", which claims the benefit of U.S. Provisional Application No. 62/189,318, filed Jul. 7, 2015, the entire disclosures of which are incorporated herein by reference.

BACKGROUND

Prior orthodontic procedures typically involve repositioning a patient's teeth to a desired arrangement in order to correct malocclusions and/or improve aesthetics. To achieve these objectives, orthodontic appliances such as braces, retainers, shell aligners, and the like can be applied to the patient's teeth by an orthodontic practitioner. The appliance can be configured to exert force on one or more teeth in order to effect desired tooth movements. The application of force can be periodically adjusted by the practitioner (e.g., by altering the appliance or using different types of appliances) in order to incrementally reposition the teeth to a desired arrangement.

The prior orthodontic methods and apparatus to move teeth can be less than ideal in at least some respects. In some instances, prior orthodontic approaches that employ an appliance with homogeneous and/or continuous material properties may not provide sufficient control over the forces applied to the teeth. In some instances, prior orthodontic treatment involves using a repositioning appliance in combination with a supplementary device that is fabricated separately. In some instances, although prior power arms can be used to apply torque to teeth, the use and placement of power arms can be less than ideal.

In light of the above, improved orthodontic appliances are needed. Ideally such appliances would provide more accurate tooth movement with improved control over the forces applied to the teeth.

SUMMARY

Improved systems, methods, and devices for repositioning a patient's teeth are provided herein. An orthodontic appliance for repositioning teeth can comprise variable localized properties in order to improve control of force and/or torque application onto different subsets of teeth. In some embodiments, an orthodontic appliance comprises a heterogeneous thickness, stiffness, and/or material composition across different portions of the appliance in order to provide more precise control over the forces applied to the teeth. An appliance with a heterogeneous thickness, stiffness, and/or material composition can be produced by direct fabrication techniques which provide control of the appliance geometry and material composition in three dimensions. The direct fabrication methods herein allow for the production of appliances with complex and heterogeneous appliance geometries and compositions that would otherwise be difficult to achieve using prior fabrication methods.

Systems, methods, and devices for orthodontic appliances with integrally formed features are provided herein. An orthodontic appliance with integrally formed features can include an appliance shell adapted to be worn over one or more teeth and a feature integrally formed into the appliance, e.g., by direct fabrication. Advantages of the system, methods and devices described herein include one or more of the following: (1) the appliance and feature are produced in a single fabrication step such that the feature is integrally formed into the appliance; (2) use of direct fabrication allows for integrally formed features with geometries that are otherwise complicated, cumbersome, and often precluded by previous indirect fabrication technologies; and (3) appliances directly fabricated with integrally formed features may allow for more flexible and convenient orthodontic treatment.

Systems, methods, and devices for improved power arms for moving teeth are provided herein. The power arms can be directly fabricated with an appliance to move teeth in order to provide additional amounts of force to the teeth with the appliance. Alternatively, the power arms may comprise attachment structures to adhere the power arms to the teeth.

The power arms can be directly fabricated with a connecting spring structure extending between the power arms. The connecting spring structure can be directly fabricated to generate predetermined amounts of force when placed on the teeth to provide improved tooth movement. The power arms can be directly fabricated with a three dimensional shape profile determined in response to a scan of the mouth of the patient, in order to improve comfort. The power arms can be directly fabricated with alignment structures shaped to receive features of the teeth in order to accurately place the power arms accurately on the teeth. The power arms can be directly fabricated with a preloaded connecting structure extending between the power arms to apply force to the power arms, and a counter-force connector extending between the power arms to oppose the preloaded connecting structure and facilitate placement.

In another aspect, a method for fabricating an orthodontic appliance comprising an integrally formed component is provided. The method can comprise: determining a movement path to move one or more teeth from an initial arrangement to a target arrangement; determining an appliance geometry for an orthodontic appliance comprising a shell and an integrally formed component, wherein the shell comprises a plurality of teeth receiving cavities shaped to move the one or more teeth from the initial arrangement to the target arrangement; and generating instructions for direct fabrication of the orthodontic appliance, wherein the instructions are configured to cause direct fabrication of the shell using a first material and direct fabrication of the integrally formed component using a second, different material.

In another aspect, a system for fabricating an orthodontic appliance comprising an integrally formed component is provided. The system can comprise one or more processors configured with instructions to: determine a movement path to move one or more teeth from an initial arrangement to a target arrangement; determine an appliance geometry for an orthodontic appliance comprising a shell and an integrally formed component, wherein the shell comprises a plurality of teeth receiving cavities shaped to move the one or more teeth from the initial arrangement to the target arrangement; and generate instructions for direct fabrication of the orthodontic appliance, wherein the instructions are configured to cause direct fabrication of the shell using a first material and direct fabrication of the integrally formed component using a second, different material.

In another aspect, an appliance for placement on teeth of a patient is provided. The appliance comprises: a plurality of power arms; a connecting structure coupled to the plurality of power arms to apply a first force to the plurality of power arms; and a counter-force connector coupled to the plurality of power arms to apply a second force to the plurality of power arms opposing the first force.

In another aspect, a method of fabricating an orthodontic appliance is provided. The method comprises: determining a movement path to move one or more teeth from an initial arrangement to a target arrangement; determining an appliance geometry for an orthodontic appliance configured to produce movement of the one or more teeth from the initial arrangement to the target arrangement, the orthodontic appliance comprising a plurality of power arms; and generating instructions for direct fabrication of the orthodontic appliance comprising the plurality of power arms.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 14A through 14C illustrate use of anisotropic properties for reducing unwanted pairing of movements, in accordance with embodiments;

FIGS. 35A through 35C illustrates the operation of a counter-force connecter to pre-load a pair of power arms for installation, in accordance with embodiments;

FIGS. 36A through 36C illustrates the operation of a counter-force connecter to pre-load a pair of power arms for installation, in accordance with embodiments;

DETAILED DESCRIPTION

Figure 1A:
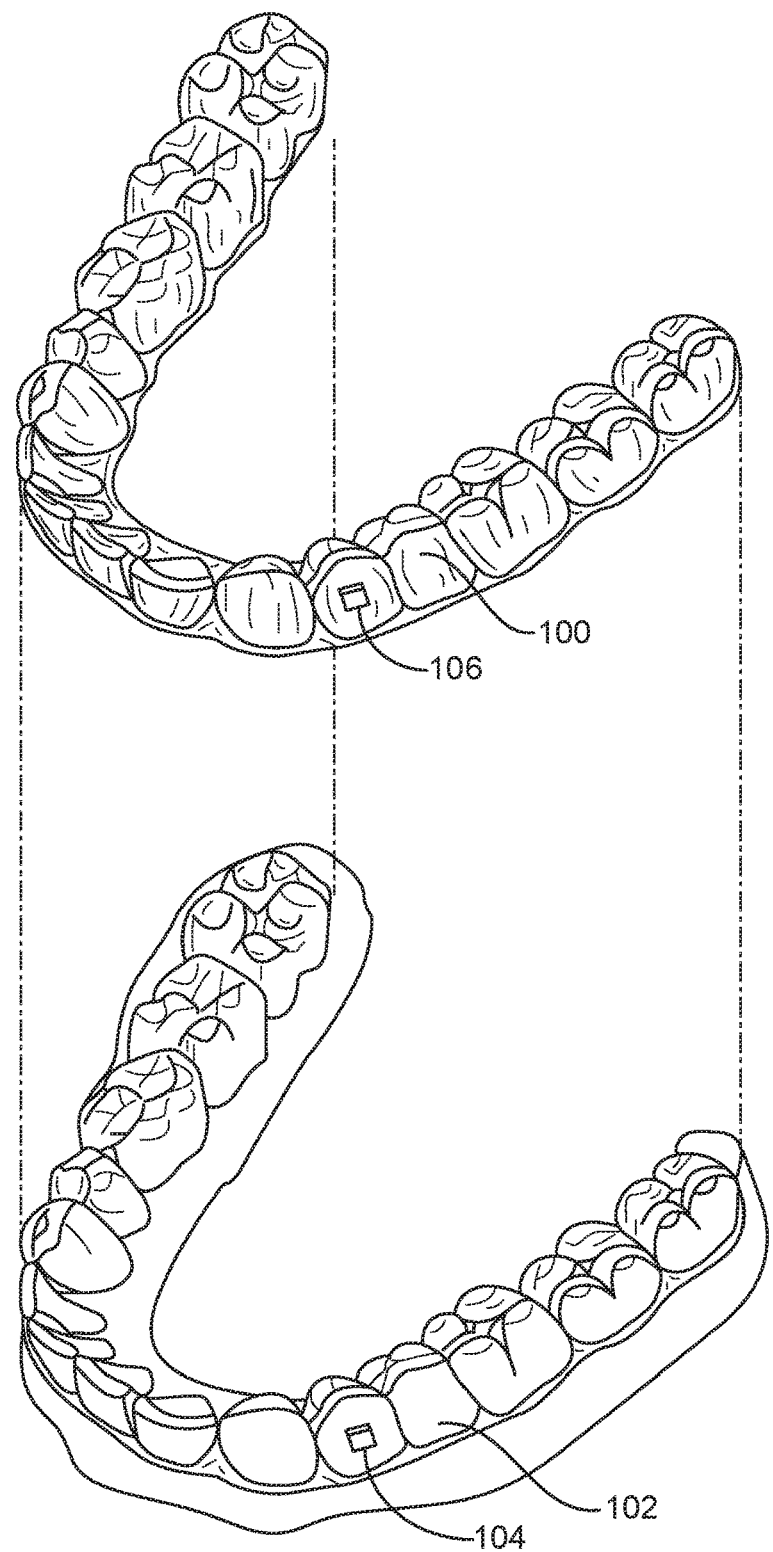
FIG. 1A illustrates a tooth repositioning appliance, in accordance with embodiments.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the methods, systems, and apparatus of the present disclosure provided herein without departing from the spirit and scope of the invention as described herein.

As used herein the terms "dental appliance," "orthodontic appliance," and "tooth receiving appliance" are treated synonymously.

As used herein the terms "rigid" and "stiff" are treated synonymously.

As used herein the term "and/or" is used as a functional word to indicate that two words or expressions are to be taken together or individually. For example, A and/or B encompasses A alone, B alone, and A and B together.

As used herein the terms "torque" and "moment" are treated synonymously.

As used herein a "moment" encompasses a force acting on an object such as a tooth at a distance from a center of resistance. The moment may be calculated with a vector cross product of a vector force applied to a location corresponding to a displacement vector from the center of resistance, for example. The moment may comprise a vector pointing in a direction. A moment opposing another moment may encompass one of the moment vectors oriented toward a first side of the object such as the tooth and the other moment vector oriented toward an opposite side of the object such as tooth, for example. Any discussion herein referring to application of forces on a patient's teeth is equally applicable to application of moments on the teeth, and vice-versa.

As used herein a "plurality of teeth" encompasses two or more teeth. In some embodiments, one or more posterior teeth comprises one or more of a molar, a premolar or a canine, and one or more anterior teeth comprising one or more of a central incisor, a lateral incisor, a cuspid, a first bicuspid or a second bicuspid.

The present disclosure provides orthodontic systems and related methods for designing and providing improved or more effective tooth moving systems for eliciting a desired tooth movement and/or repositioning teeth into a desired arrangement.

The embodiments disclosed herein can be used to couple groups of one or more teeth to each other. The groups of one or more teeth may comprise a first group of one or more anterior teeth and a second group of one or more posterior teeth. The first group of teeth can be coupled to the second group of teeth with the polymeric shell appliances as disclosed herein.

The embodiments disclosed herein are well suited for moving one or more teeth of the first group of one or more teeth or moving one or more of the second group of one or more teeth, and combinations thereof.

The embodiments disclosed herein are well suited for combination with one or known commercially available tooth moving components such as attachments and polymeric shell appliances. In some embodiments, the appliance and one or more attachments are configured to move one or more teeth along a tooth movement vector comprising six degrees of freedom, in which three degrees of freedom are rotational and three degrees of freedom are translation.

The present disclosure provides orthodontic appliances and related systems, methods, and devices. Repositioning of teeth may be accomplished with the use of a series of removable elastic positioning appliances such as the Invisalign® system available from Align Technology, Inc., the assignee of the present disclosure. Such appliances may have a thin shell of elastic material that generally conforms to a patient's teeth but is slightly out of alignment with an initial or immediately prior tooth configuration. Placement of the appliance over the teeth applies controlled forces in specific locations to gradually move the teeth into the new configuration. Repetition of this process with successive appliances comprising new configurations eventually moves the teeth through a series of intermediate configurations or alignment patterns to a final desired configuration.

The force generating components disclosed herein can generate forces based on a target tooth displacement or orientation. For example, an amount of tooth displacement can be selected, and the force generating component can be fabricated such that a tooth displacement force is generated when the appliance is worn, so long as the amount of tooth displacement is less than the target tooth displacement. Thus, an appliance can generate tooth displacement forces without causing excessive tooth displacement. In some cases, the target tooth displacement can be adjustable; for example, adjustable screws, springs, bands, or other components can be adjusted to change the size of the aligner, thereby changing the target tooth displacement. An adjustable aligner can be used to generate a slow tooth displacement, for example.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated with machining such as an appliance fabricated from a block of material with computer numeric control machining.

Turning now to the drawings, in which like numbers designate like elements in the various figures, FIG. 1A illustrates an exemplary tooth repositioning appliance or aligner 100 that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using additive manufacturing techniques, from a digital model of an appliance. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Optionally, in cases involving more complex movements or treatment plans, it may be beneficial to utilize auxiliary components (e.g., features, accessories, structures, devices, components, and the like) in conjunction with an orthodontic appliance. Examples of such accessories include but are not limited to elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, and the like. In some embodiments, the appliances, systems and methods described herein include improved orthodontic appliances with integrally formed features that are shaped to couple to such auxiliary components, or that replace such auxiliary components.

Figure 1B:
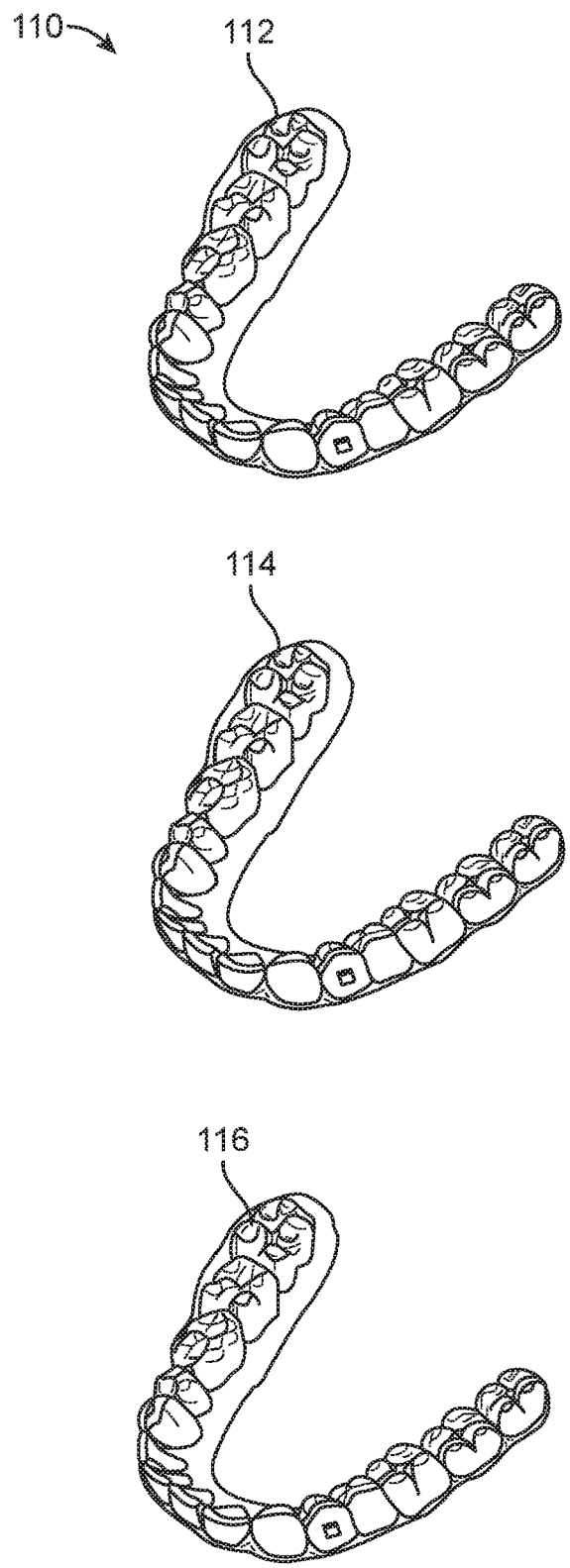
FIG. 1B illustrates a tooth repositioning system, in accordance with embodiments.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 1C:
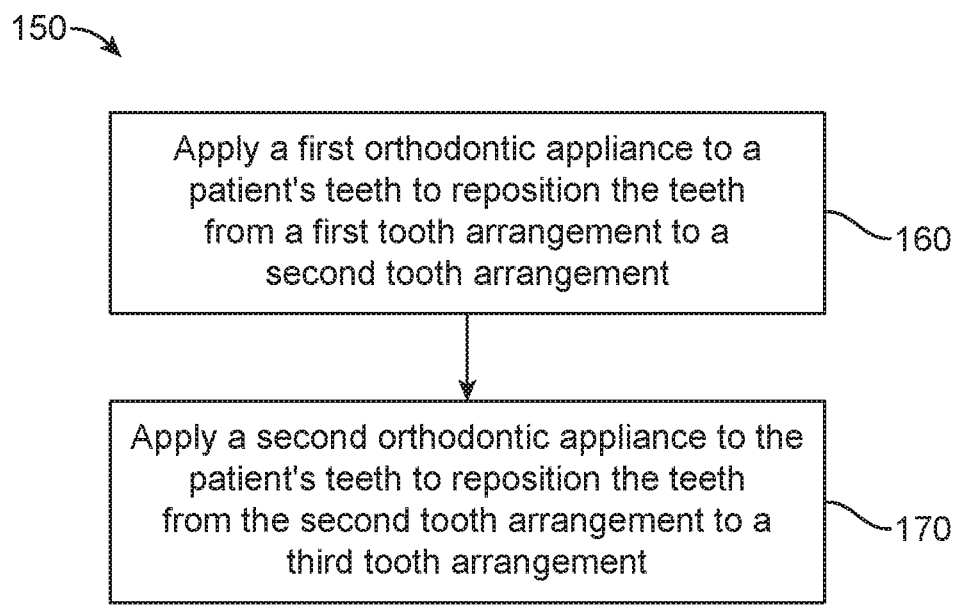
FIG. 1C illustrates a method of orthodontic treatment using a plurality of appliances, in accordance with embodiments.

FIG. 1C illustrates a method 150 of orthodontic treatment using a plurality of appliances, in accordance with embodiments. The method 150 can be practiced using any of the appliances or appliance sets described herein. In step 160, a first orthodontic appliance is applied to a patient's teeth in order to reposition the teeth from a first tooth arrangement to a second tooth arrangement. In step 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Orthodontic Appliances with Variable Properties

Systems, methods, and devices for improved orthodontic treatment of a patient's teeth are provided herein. In some embodiments, the present disclosure provides improved orthodontic appliances having different portions with different properties. The use of appliances with variable localized properties as described herein can improve control over the application of forces to different subsets of teeth, thus enhancing the flexibility and effectiveness of orthodontic treatment. In some embodiments, the appliances with variable localized properties herein are produced using direct fabrication methods which provide precise control over the geometry, composition, and/or properties of the appliance in three dimensions. Direct fabrication permits manufacturing of appliances with complex geometries and heterogeneous properties that would otherwise be difficult to produce using other fabrication techniques.

In one aspect, an orthodontic appliance for treating a patient's teeth is provided, the appliance comprising: a first appliance portion receiving a first subset of the patient's teeth; and a second appliance portion receiving a second subset of the patient's teeth, wherein the first and second appliance portions differ from each other with respect to two or more of thickness, stiffness, or material composition.

In some embodiments, the first appliance portion comprises an increased thickness relative to the second appliance portion. The first appliance portion can comprise an anterior occlusal portion and the second appliance portion can comprise a posterior occlusal portion, or the first appliance portion can comprise a posterior occlusal portion and the second appliance portion can comprise an anterior occlusal portion. The first appliance portion can comprise a gingival portion shaped to engage undercuts of teeth and the second appliance portion can comprise an occlusal portion shaped to receive crowns of teeth.

In some embodiments, the first appliance portion comprises a force application structure arranged to engage and apply force to a tooth. The first appliance portion can comprise a handle structure to facilitate removal of the appliance from the patient's teeth. The first appliance portion can comprise a rib structure on a buccal surface of the appliance (e.g., near canine teeth of the patient), on an occlusal surface of the appliance, on a lingual surface of the appliance, or on a gingival portion of the appliance.

In some embodiments, the second appliance portion comprises recesses or apertures shaped to reduce stiffness of the second appliance portion relative to the first appliance portion.

In some embodiments, the first appliance portion comprises an increased stiffness relative to the second appliance portion. The first appliance portion can comprise an increased degree of photopolymerization relative to the second appliance portion so as to produce the increased stiffness. The first appliance portion can comprise a gingival portion and the second appliance portion can comprise an occlusal portion. The first appliance portion can comprise a buccal portion and the second appliance portion can comprise a lingual portion.

In some embodiments, the first appliance portion comprises a stiff band extending along a buccal and/or lingual surface of a tooth.

In some embodiments, the first appliance portion comprises a plurality of shell segments and the second appliance portion comprises an elastic portion joining the plurality of shell segments.

In some embodiments, the first appliance portion comprises a first material and the second appliance portion comprises a second material different from the first material. At least one of the first or second materials can comprise a stiffness along a first direction different from a stiffness along a second direction. The first direction can be a transverse direction and the second direction can be a vertical direction, or the first direction can be a rotational direction and the second direction can be a vertical direction.

In some embodiments, the first appliance portion or the second appliance portion comprises an occlusal structure, an arch expander, an elastic, an air flow structure, a pontic, ornamental feature, inflatable structure, or functional layer or coating.

In some embodiments, the first appliance portion is integrally formed with the second appliance portion as a single piece using a direct fabrication technique. The direct fabrication technique can be an additive manufacturing technique or a subtractive manufacturing technique. The additive manufacturing technique can comprise one or more of: vat photopolymerization, material jetting, binder jetting, material extrusion, powder bed fusion, sheet lamination, or directed energy deposition.

In some embodiments, the appliance further comprises a third appliance portion receiving a third subset of the patient's teeth, the third appliance portion differing from one or more of the first and second appliance portions with respect to two or more of thickness, stiffness, or material composition.

In another aspect, a method for treating a patient's teeth comprises providing an appliance as in any of the embodiments herein.

In another aspect, a method for fabricating an orthodontic appliance for treating a patient's teeth is provided, the method comprising: determining a movement path to move one or more teeth from an initial arrangement to a target arrangement; determining a force system to move the one or more teeth along the movement path; determining an appliance geometry and material composition of an appliance configured to produce the force system, wherein the appliance comprises two or more of a heterogeneous thickness, a heterogeneous stiffness, or a heterogeneous material composition; and generating instructions for fabricating the appliance with the appliance geometry and the material composition using a direct fabrication technique.

In some embodiments, the direct fabrication technique is an additive manufacturing technique or a subtractive manufacturing technique. The additive manufacturing technique can comprise one or more of: vat photopolymerization, material jetting, binder jetting, material extrusion, powder bed fusion, sheet lamination, or directed energy deposition.

In some embodiments, the appliance comprises the heterogeneous thickness, and thicker portions of the appliance are configured to exert a different force (e.g., more or less force) on the one or more teeth than thinner portions of the appliance. The method can further comprise determining locations and geometries for the thicker portions and the thinner portions.

In some embodiments, the appliance comprises the heterogeneous stiffness, and stiffer portions of the appliance are configured to exert a different force (e.g., more or less force) on the one or more teeth than more elastic portions of the appliance. The method can further comprise determining locations and geometries for the stiffer portions and the more elastic portions. The stiffer portions can comprise a different material composition than the more elastic portions. The stiffer portions can comprise a different degree of photopolymerization than the more elastic portions.

In some embodiments, the appliance comprises an increased stiffness along a targeted tooth movement direction and a decreased stiffness away from the targeted tooth movement direction.

In some embodiments, the appliance comprises a plurality of relatively stiff segments joined to each other by one or more relatively elastic portions so as to isolate the forces generated by the plurality of relatively stiff segments from each other.

In some embodiments, the appliance further comprises one or more of: a heterogeneous elastic modulus, a heterogeneous hardness, a heterogeneous strength, a heterogeneous compressibility, a heterogeneous stress relaxation, a heterogeneous hydrophobicity, a heterogeneous hydrophilicity, a heterogeneous Poisson ratio, a heterogeneous strain rate, a heterogeneous viscoelasticity, or a heterogeneous polarity.

In another aspect, a system for fabricating an orthodontic appliance for treating a patient's teeth is provided. The system can comprise one or more processors configured with instructions to: determine a movement path to move one or more teeth from an initial arrangement to a target arrangement; determine a force system to move the one or more teeth along the movement path; determine an appliance geometry and material composition of an appliance configured to produce the force system, wherein the appliance comprises two or more of a heterogeneous thickness, a heterogeneous stiffness, or a heterogeneous material composition; and generate instructions for fabricating the appliance with the appliance geometry and the material composition using a direct fabrication technique.

In some embodiments, the direct fabrication technique is an additive manufacturing technique or a subtractive manufacturing technique. The additive manufacturing technique can comprise one or more of: vat photopolymerization, material jetting, binder jetting, material extrusion, powder bed fusion, sheet lamination, or directed energy deposition.

In some embodiments, the appliance comprises the heterogeneous thickness, and thicker portions of the appliance are configured to exert a different force on the one or more teeth than thinner portions of the appliance.

In some embodiments, the one or more processors are further configured with instructions to determine locations and geometries for the thicker portions and the thinner portions.

In some embodiments, the appliance comprises the heterogeneous stiffness, and stiffer portions of the appliance are configured to exert a different force on the one or more teeth than more elastic portions of the appliance.

In some embodiments, the one or more processors are further configured with instructions to determine locations and geometries for the stiffer portions and the more elastic portions.

In some embodiments, the stiffer portions comprise a different material composition than the more elastic portions.

In some embodiments, the stiffer portions comprise a different degree of photopolymerization than the more elastic portions.

In some embodiments, the appliance comprises an increased stiffness along a targeted tooth movement direction and a decreased stiffness away from the targeted tooth movement direction.

In some embodiments, the appliance comprises a plurality of relatively stiff segments joined to each other by one or more relatively elastic portions so as to isolate the forces generated by the plurality of relatively stiff segments from each other.

In some embodiments, the appliance further comprises one or more of: a heterogeneous elastic modulus, a heterogeneous hardness, a heterogeneous strength, a heterogeneous compressibility, a heterogeneous stress relaxation, a heterogeneous hydrophobicity, a heterogeneous hydrophilicity, a heterogeneous Poisson ratio, a heterogeneous strain rate, a heterogeneous viscoelasticity, or a heterogeneous polarity.

In another aspect, a system configured to perform any embodiment of the methods herein is provided.

The ability of an orthodontic appliance to effectively treat a patient's teeth can depend on its properties, such as stiffness, elastic modulus, hardness, thickness, strength, compressibility, stress relaxation, hydrophobicity/hydrophilicity, Poisson ratio, strain rate, viscoelasticity, and/or polarity. For instance, these properties can influence the amount of force and/or torque that can be exerted by the appliance onto the teeth, as well as the extent to which such forces and/or torques can be controlled (e.g., with respect to location of application, direction, magnitude, etc.). The optimal properties for tooth repositioning may vary based on the type of tooth to be repositioned (e.g., molar, premolar, canine, incisor), movement type (e.g., extrusion, intrusion, rotation, torquing, tipping, translating), targeted movement distance, use of tooth-mounted attachments, or combinations thereof. Different teeth in the patient's jaw may require different types of appliance properties in order to be effectively repositioned. In some instances, it can be relatively difficult to effectively reposition multiple teeth using an orthodontic appliance with uniform and/or homogeneous properties.

Accordingly, various embodiments of the present disclosure provide orthodontic appliances having properties that are heterogeneous and/or variable across different portions of appliance in order to allow for more effective repositioning of multiple teeth. In such embodiments, one or more portions of the appliance can have one or more properties that differ from those of one or more other portions, such as with respect to one or more of stiffness, elastic modulus, hardness, thickness, strength, compressibility, stress relaxation, hydrophobicity/hydrophilicity, Poisson ratio, strain rate, viscoelasticity, and/or polarity. An appliance can include any number of portions with different properties, such as two, three, four, five, six, seven, eight, nine, ten, twenty, thirty, forty, fifty, or more portions with different properties. For example, an appliance can include a first appliance portion receiving a first subset of the patient's teeth and a second appliance portion receiving a second subset of the patient's teeth, and the first and second portions can differ from each other with respect to one or more of thickness, stiffness, or material composition. In some embodiments, the first and second portions can differ from each other with respect to two or more of thickness, stiffness, or material composition. In some embodiments, the first and second portions can differ from each other with respect to thickness, stiffness, and/or material composition, or any other appliance property described herein.

An appliance portion can include any part of an appliance, such as one or more tooth-receiving cavities or portions thereof. The size and location of an appliance portion can be varied as desired. For example, an appliance portion can be arranged to receive and/or engage a subset of the patient's teeth, such as a single tooth, a plurality of teeth, a portion of a tooth (e.g., a lingual, buccal, or occlusal surface), or combinations thereof. In some embodiments, appliance portions that receive different subsets of teeth (e.g., anterior teeth, posterior teeth, teeth to be repositioned, teeth to be retained in a current position) have different properties. Alternatively or in combination, appliance portions that engage different surfaces of the teeth (e.g., buccal surfaces, lingual surfaces, occlusal surfaces) can have different properties. The use of orthodontic appliances with variable localized properties can allow for improved control over the forces and/or torques to be applied to the patient's teeth, as described further herein.

In some embodiments, a property of an orthodontic appliance (e.g., stiffness, thickness, material composition, etc.) varies along one or more directions (e.g., mesial-distal direction, occlusal-gingival direction, buccal-lingual direction, anterior-posterior direction, interior-exterior direction), also referred to herein as a "functionally graded property." The property may vary gradually along the one or more directions (e.g., vary according to a continuous function), or may exhibit discrete changes (e.g., vary according to a non-continuous function such as a step function). The property may vary according to a linear or non-linear function, as desired.

Optionally, the directionality of a property of an orthodontic appliance (e.g., stiffness, thickness, material composition, etc.) may be varied. For example, mechanical properties of a material or structure of the appliance (e.g., stiffness, elongation, tensile strength, compressive strength, bending properties, viscoelastic properties, etc.) may be anisotropic, such that the properties are different when measured along x, y, and z directions. By changing the directionality of the structures and/or materials of an appliance, varying properties can be developed along different directions (e.g., mesial-distal direction, occlusal-gingival direction, buccal-lingual direction, anterior-posterior direction, interior-exterior direction). Such variations in directionality can be achieved using the direct fabrication methods described herein, such as 3D printing.

In some embodiments, the orthodontic appliances with variable localized properties presented herein are produced by direct fabrication. The direct fabrication techniques presented herein may be particularly suited for manufacturing of appliances with different localized properties that would otherwise be difficult to achieve with other fabrication methods (e.g., indirect fabrication methods such as thermoforming a material sheet over a mold). For instance, in some embodiments, the direct fabrication techniques herein are used to fabricate orthodontic appliances exhibiting variable thicknesses, variable stiffnesses, and/or variable material compositions at different portions of the appliance. Additional description of direct fabrication methods suitable for producing the appliances of the present disclosure are provided further herein.

In some embodiments, direct fabrication is advantageous for producing appliances with variable thicknesses. In contrast to indirect fabrication methods such as thermoforming, in which the thickness of the resultant appliance is generally limited by the thickness of the thermoformed sheet, may vary based on the location of the appliance (e.g., gingival portions may experience more stretching during thermoforming and thus may be thinner), and may be sensitive to variations in process parameters (e.g., thermoforming temperature, vacuum pressure applied, material type, etc.), direct fabrication allows for control over the thickness of the fabricated appliance at any desired location. For example, the thickness of an appliance may be varied between one or more of the following locations: a buccal portion, a lingual portion, an occlusal portion, a gingival portion, an anterior portion, a posterior portion, or combinations thereof. Optionally, an appliance can have a thickness varying from about 0.05 mm to about 8 mm, or from about 0.1 mm to about 2 mm. These values are provided as examples only and not intended to be limiting. It shall be appreciated that the dimensions of the appliances herein can be varied as desired. In some embodiments, the minimum thickness of the appliance can be about 10%, 20%, 30%, 40%, 50%, 60%, 70%, 80%, or 90% of the maximum thickness of the appliance. The thickness of the appliance can be varied in order to control the forces exerted by the appliance onto the patient's teeth. For example, relatively thick portions of the appliance can exert more force on the teeth (e.g., due to the increased stiffness of such portions), while relatively thin portions of the appliance can exert less force on the teeth (e.g., due to the reduced stiffness of such portions). Accordingly, the varying thicknesses of an appliance can be configured to apply a specified force system to a patient's teeth at any desired location.

Figure 2A:
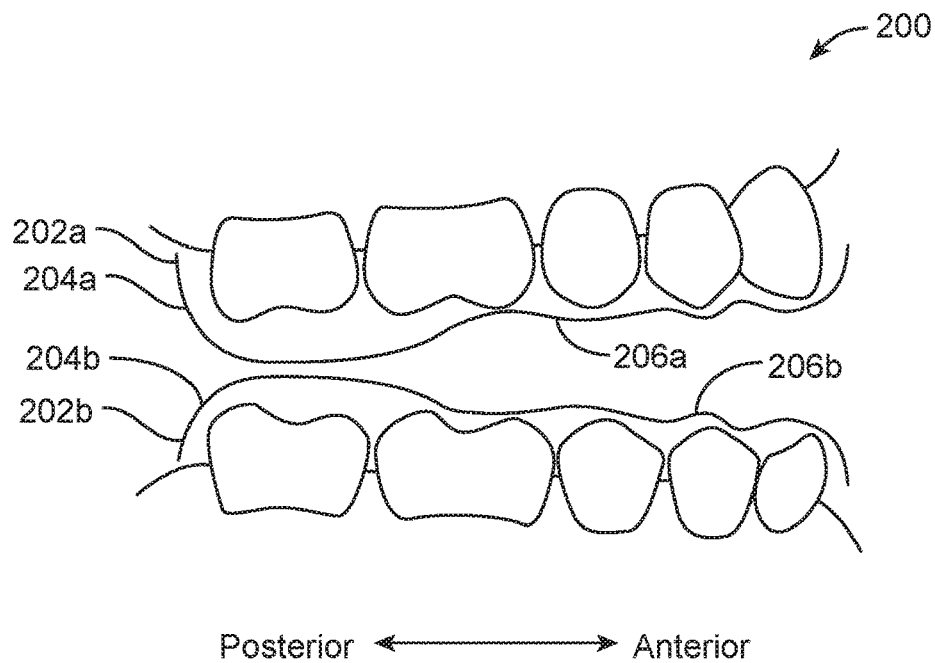
FIGS. 2A and 2B illustrate orthodontic appliances with varying occlusal thicknesses, in accordance with embodiments.
Figure 2B:
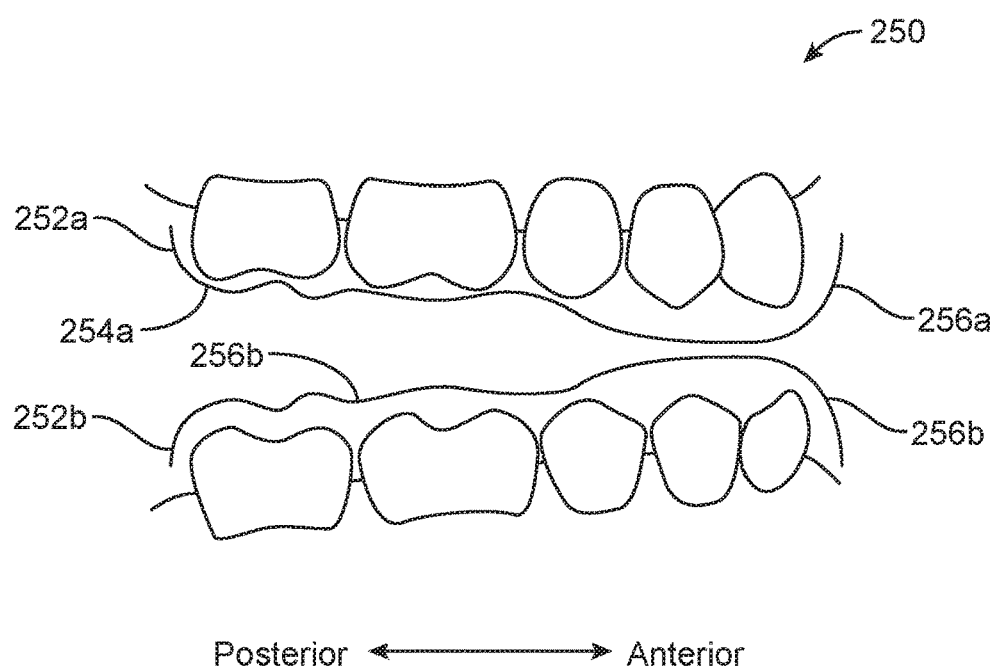

FIGS. 2A and 2B illustrate orthodontic appliances with varying occlusal thicknesses, in accordance with embodiments. Thicker occlusal portions can be used to apply intrusion forces on selected teeth, while thinner occlusal portions can be used where tooth intrusion is not desired. In some embodiments, thinner occlusal portions can improve patient comfort by reducing the vertical spacing between the upper and lower arches, and can help reduce open bite when wearing the appliance. Additionally, thinner occlusion portions may be beneficial for maintaining the natural inter-digitation between upper and lower teeth during treatment. FIG. 2A illustrates an appliance 200 including an upper shell 202a and a lower shell 202b. Each shell includes a thicker posterior occlusal portion 204a, 204b, and a thinner anterior occlusal portion 206a, 206b. The appliance 200 can be used to intrude the posterior teeth relative to the anterior teeth, e.g., to close an open bite. FIG. 2B illustrates an appliance 250 including an upper shell 252a and a lower shell 252b. Each shell includes a thinner posterior occlusal portion 254a, 254b, and a thicker anterior occlusal portion 256a, 256b. The thinner posterior occlusal portion can be used to intrude the anterior teeth relative to the posterior teeth, e.g., to close a deep bite or overbite. In some embodiments, a thinner occlusal portion provides a better match for the natural articulation of the patient's jaws, e.g., to reduce temporomandibular joint issues.

In some embodiments, occlusal structures for controlling the relative positioning (e.g., left-right, anterior-posterior, etc.) of the upper and lower jaws such as twin blocks, occlusal blocks, mandibular advancement structures, and the like can be directly built into the appliance by varying the thickness of the occlusal surfaces. These occlusal structures can be used to correct various issues related to the patient's bite, including but not limited to class II malocclusions, class III malocclusions, cross bite, open bite, and sleep apnea. Additional examples of integrally formed occlusal structures and features suitable for use with the embodiments herein are discussed below.

Figure 3A:
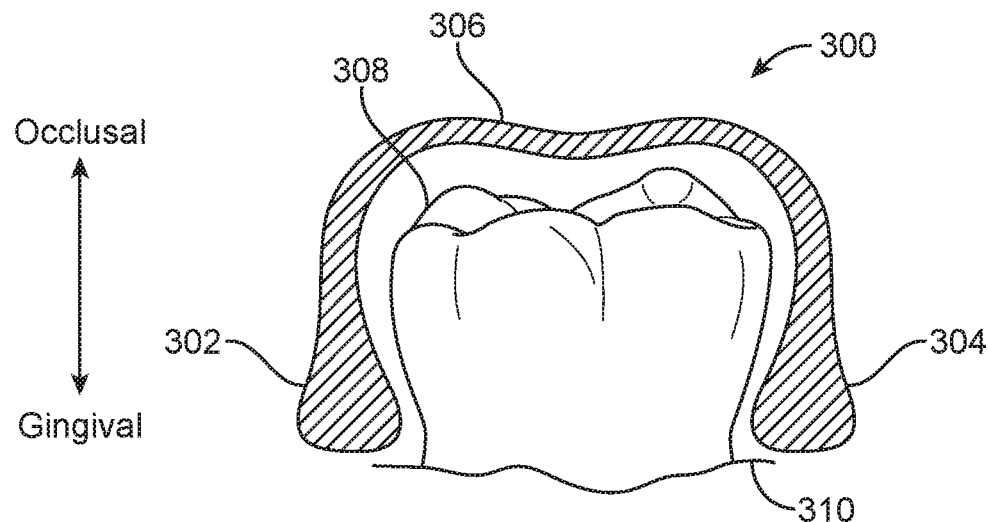
FIGS. 3A and 3B illustrate orthodontic appliances with varying thicknesses along a vertical direction, in accordance with embodiments.
Figure 3B:
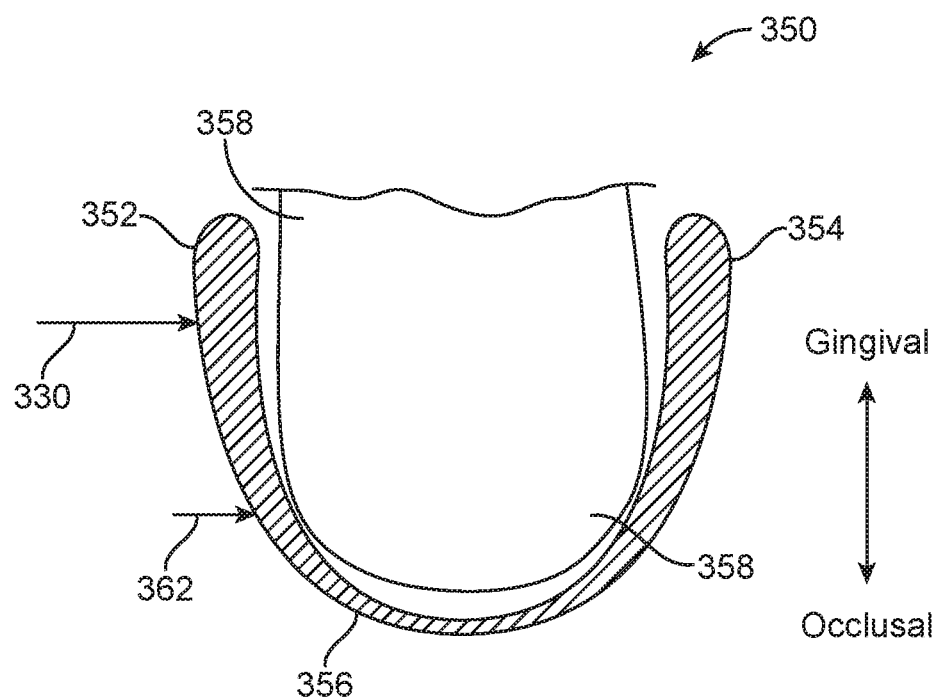

FIGS. 3A and 3B illustrate orthodontic appliances with varying thicknesses along a vertical direction, in accordance with embodiments. "Vertical" may be used herein to refer to the direction along the height of a tooth crown, such that the thickness of one or more occlusal portions of the appliance differs from the thickness of one or more gingival portions of the appliance. FIG. 3A shows a cross-sectional view of an appliance shell 300 having thicker gingival portions 302, 304 and a thinner occlusal surface 306. The shell 300 can be shaped to receive a tooth crown 308, with the edges of the gingival portions 302, 304 terminating above the gingiva. The thickened gingival portions 302, 304 can be shaped to engage the undercuts of the tooth crown 308 in order to facilitate extrusion of the tooth.

In some embodiments, an orthodontic appliance with varying thicknesses along a vertical direction can be used to control movements of tooth roots. FIG. 3B shows a cross-ssectional view of an appliance shell 350 having thicker gingival portions 352, 354 and a thinner occlusal surface 356. The varying thickness of the shell 350 can result in larger forces being delivered near the bottom of the tooth crown 358 closer to the center of resistance (e.g., arrow 360) and smaller forces being delivered near the top of the tooth crown away from the center of resistance (e.g., arrow 362), thus resulting in a programmed motion of the tooth, e.g., along arrow 358. This approach can be advantageous for producing tooth translation with reduced tipping, for example.

In some embodiments, force application structures such as protrusions, ridges, dimples, and the like can be integrally formed in the appliance by selectively increasing the thickness of the appliance shell at one or more locations. A force application structure can extend inward from the interior surface of the shell towards the received tooth in order to define a contact point for application of force to the tooth. An appliance can include one or more force application structures formed on a buccal surface, lingual surface, or occlusal surface of the shell, or combinations thereof. With direct fabrication techniques, such force application structures can be positioned and shaped with greater accuracy, thus providing precise control over the magnitude and direction of the resultant forces exerted on the teeth. Additionally, direct fabrication also permits more precise control over surrounding tooth contact points compared to other fabrication methods (e.g., thermofoming).

Figure 4A:
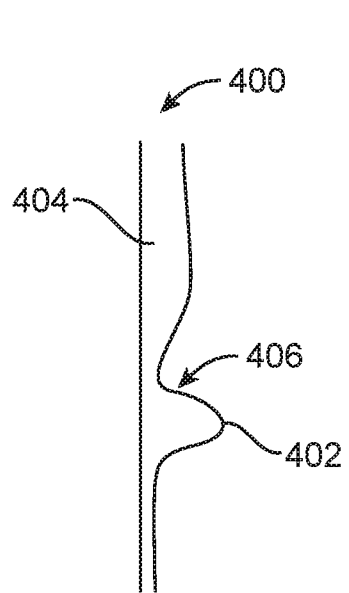
FIG. 4A shows a cross-sectional view of an exemplary force application structure, in accordance with embodiments.

FIG. 4A shows a cross-sectional view of an exemplary force application structure 400, in accordance with embodiments. The structure 400 is formed as a thickened protrusion 402 within an appliance wall 404. In some embodiments, the thickness of the portions of the wall 404 near the protrusion 402 can be varied (e.g., increased or decreased) in order to control the stiffness of the appliance near the protrusion 402. For example, the wall 404 can include a thinner portion 406 adjacent the protrusion 402 to decrease the local stiffness in order to extend the working range of the protrusion 402.

Figure 4B:
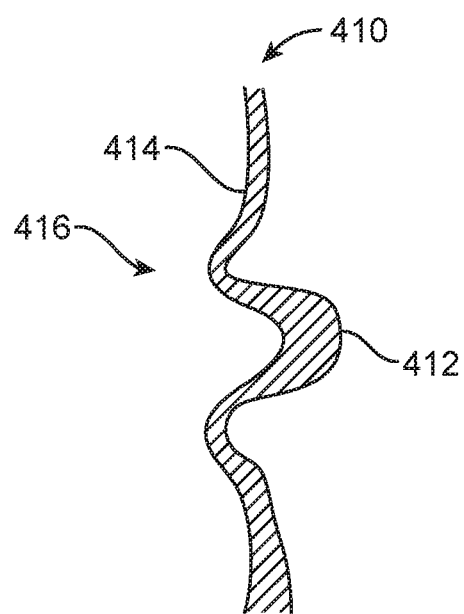
FIG. 4B shows a cross-sectional view of another exemplary force application structure, in accordance with embodiments.

FIG. 4B shows a cross-sectional view of another exemplary force application structure 410, in accordance with embodiments. The structure 410 is formed as a corrugated portion 412 within an appliance wall 414. Similar to the structure 400, the portions of the wall 414 near the corrugated portion 412 can be varied (e.g., increased or decreased) in order to control the stiffness of the appliance near the corrugated portion 412. For example, the wall 424 can include a thinner portion 416 adjacent the corrugated portion 412 to decrease the local stiffness in order to extend the working range of the corrugated portion 412.

Figure 4C:
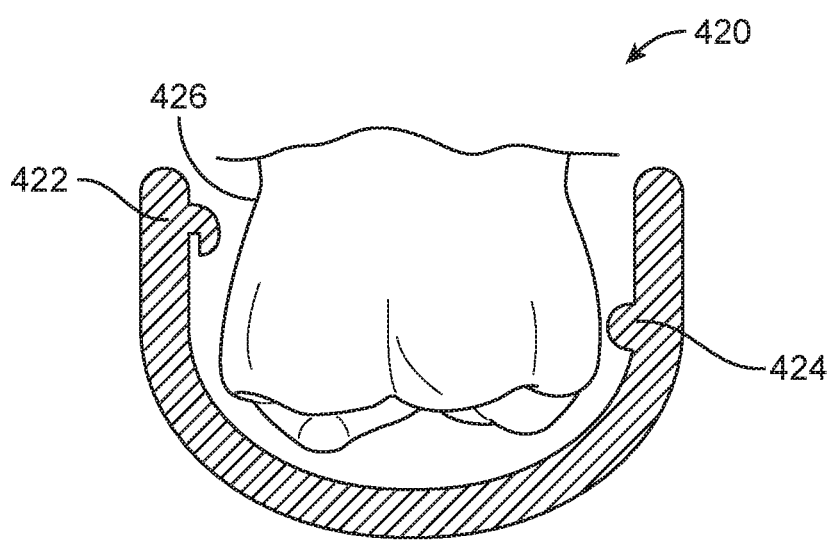
FIG. 4C shows a cross-sectional view of an appliance shell with force application structures for controlling tooth tipping and/or torque, in accordance with embodiments.

FIG. 4C shows a cross-sectional view of an appliance shell 420 with force application structures for controlling tooth tipping and/or torque, in accordance with embodiments. The shell 420 includes a buccal force application structure 422 and a lingual force application structure 424. Although the force application structures 422, 424 are depicted in FIG. 4C as protrusions or ridges, other types of structures can be used in alternative embodiments. The buccal and lingual structures 422, 424 can engage and apply forces to a received tooth 426. In some embodiments, the buccal structure 422 is positioned near the bottom of the tooth crown while the lingual structure 424 is positioned near the top of the tooth crown in order to control tipping of the tooth 426. It shall be appreciated that alternative configurations of the buccal and lingual structures 422, 424 can also be used to control tipping, e.g., a configuration with the buccal structure 422 located near the top of the crown and the lingual structure 424 located near the bottom of the crown.

Figure 4D:
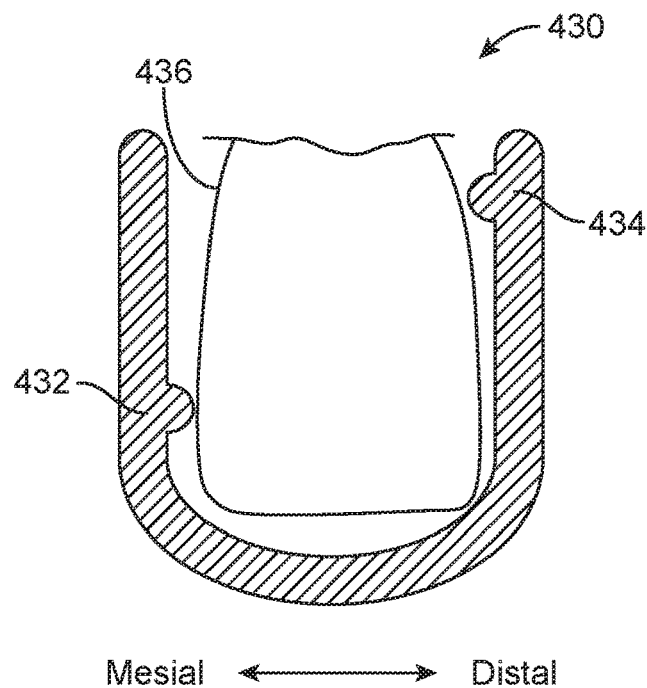
FIG. 4D shows a cross-sectional view of an appliance shell with force application structures for controlling tooth root movements, in accordance with embodiments.

FIG. 4D shows a cross-sectional view of an appliance shell 430 with force application structures for controlling tooth root movements, in accordance with embodiments. The shell 430 includes a mesial force application structure 432 and a distal force application structure 434, depicted herein as protrusions. The mesial structure 432 is positioned near the top of the tooth crown 436 and the distal structure 434 is positioned near the bottom of the tooth crown 436 in order to control movements of the tooth root. It shall be appreciated that the configuration can be reversed, e.g., with the mesial structure 432 near the bottom and the distal structure 434 near the top. In some embodiments, this configuration permits bodily translation of the entire tooth along the mesial-distal direction with reduced tipping.

Figure 4E:
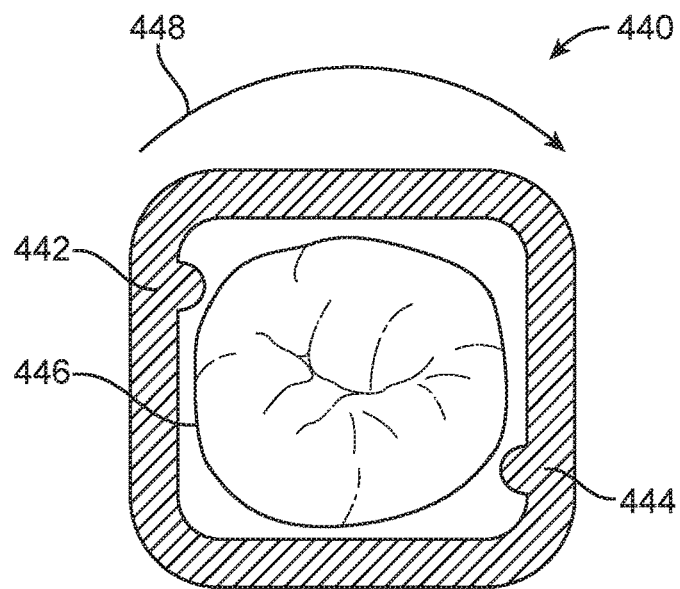
FIG. 4E shows a cross-sectional occlusal view of an appliance shell with force application structures for controlling tooth rotation, in accordance with embodiments.

FIG. 4E shows a cross-sectional occlusal view of an appliance shell 440 with force application structures for controlling tooth rotation, in accordance with embodiments. The shell 440 includes a pair of force application structures 442, 444 positioned to engage opposing sides of the tooth 446 (e.g., buccal and lingual sides) in order to create a force couple that produces rotation of the tooth 446 (e.g., along arrow 448).

Variations in the thickness of an appliance shell can also be used to form other types of functional structures in the appliances herein, and such structures may be configured to perform functions in addition to or other than application of forces to the teeth, such as improving ease of use and patient comfort. The direct fabrication methods presented herein provide improved flexibility and control over the geometry and positioning of such structure on an orthodontic appliance.

Figure 5A:
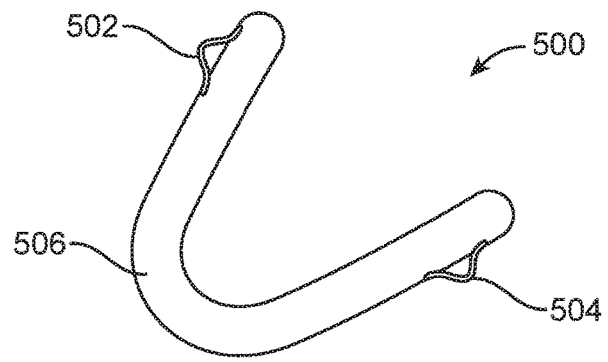
FIG. 5A illustrates an appliance with built-in handle structures in the appliance shell, in accordance with embodiments.

FIG. 5A illustrates an appliance 500 with built-in handle structures 502, 504 in the appliance shell 506, in accordance with embodiments. The handle structures 502, 504 can be used to facilitate removal of the appliance 500 from the patient's teeth. The number and positioning of the handle structures can be varied as desired. In the depicted embodiment, the handle structures 502, 504 are respectively positioned on the right and left buccal surfaces of the shell 506 near the distal portions.

Figure 5B:
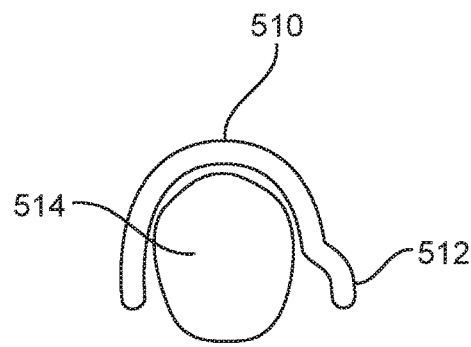
FIGS. 5B through 5D illustrate exemplary geometries for handle structures, in accordance with embodiments.
Figure 5C:
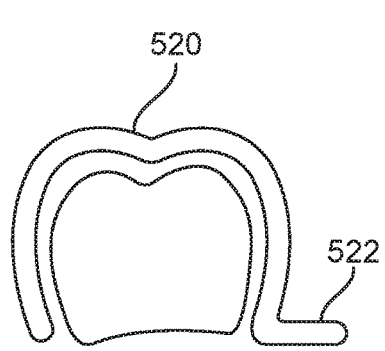
Figure 5D:
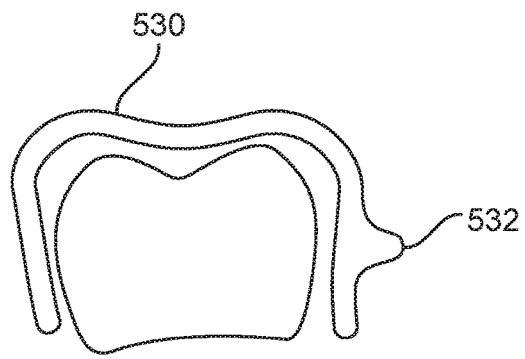

FIGS. 5B through 5D illustrate exemplary geometries for handle structures, in accordance with embodiments. FIG. 5B illustrates a shell 510 in which a gingival edge 512 is flared outwards away from the received tooth 514 in order to form a handle structure. FIG. 5C illustrates a shell 520 having a handle structure 522 positioned flush with the gingival edge of the shell 520. FIG. 5D illustrates a shell 530 having a handle structure 522 that is offset from the gingival edge of the shell 530.

Figure 6:
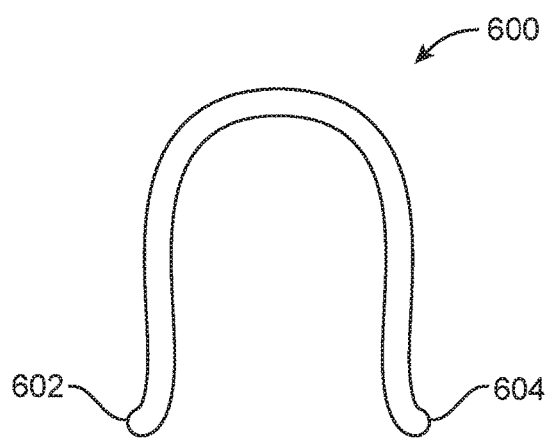
FIG. 6 illustrates a cross-sectional view of an appliance shell with gingival edges shaped to improve patient comfort, in accordance with embodiments.

FIG. 6 illustrates a cross-sectional view of an appliance shell 600 with gingival edges 602, 604 shaped to improve patient comfort, in accordance with embodiments. The edges 602, 604 can be formed into a smooth shape, such as a beveled or rounded shape, in order to reduce irritation of gingival tissues when the appliance is worn.

In some embodiments, the appliances discussed herein have variable localized stiffnesses. As discussed above and herein, variations in stiffness can influence the forces that are applied to the teeth, with stiffer portions applying more force and elastic portions applying less force. The stiffness of an appliance can be within a range from about 0.1 N/mm to about 1000 N/mm. The stiffness of an appliance can be related to its elastic modulus, and the elastic modulus of an appliance can be within a range from about 10,000 psi to about 700,000 psi. These values are provided as examples only and not intended to be limiting. It shall be appreciated that the elastic modulus, stiffness, and other properties of the appliances herein can be varied as desired. In some embodiments, the minimum stiffness of the appliance can be about 0.001%, 0.01%, 0.1%, 1%, 10%, 20%, 30%, 40%, 50%, 60%, 70%, 80%, or 90% of the maximum stiffness of the appliance.

The stiffness of an appliance portion can depend on both the geometry of the portion and the elastic modulus of the material used to form that portion. For example, the thickness of an appliance can influence the stiffness of the appliance, with thicker portions being more stiff and thinner portions being more compliant. Accordingly, in some embodiments, appliance thickness is locally varied in order to selectively modulate the stiffness of the appliance. This approach allows for variations in stiffness to be achieved based only on the appliance geometry, without using multiple material types or different curing parameters. However, it shall be appreciated that although certain embodiments herein describe control of appliance stiffness using variable thicknesses, other approaches disclosed herein such as variable photopolymerization and/or variable material compositions can also be used to achieve similar results, and that such approaches can be combined with or substituted for any of the thickness-based approaches described herein. For example, variations in stiffness can also be achieved by using materials with different elastic moduli.

Figure 7:
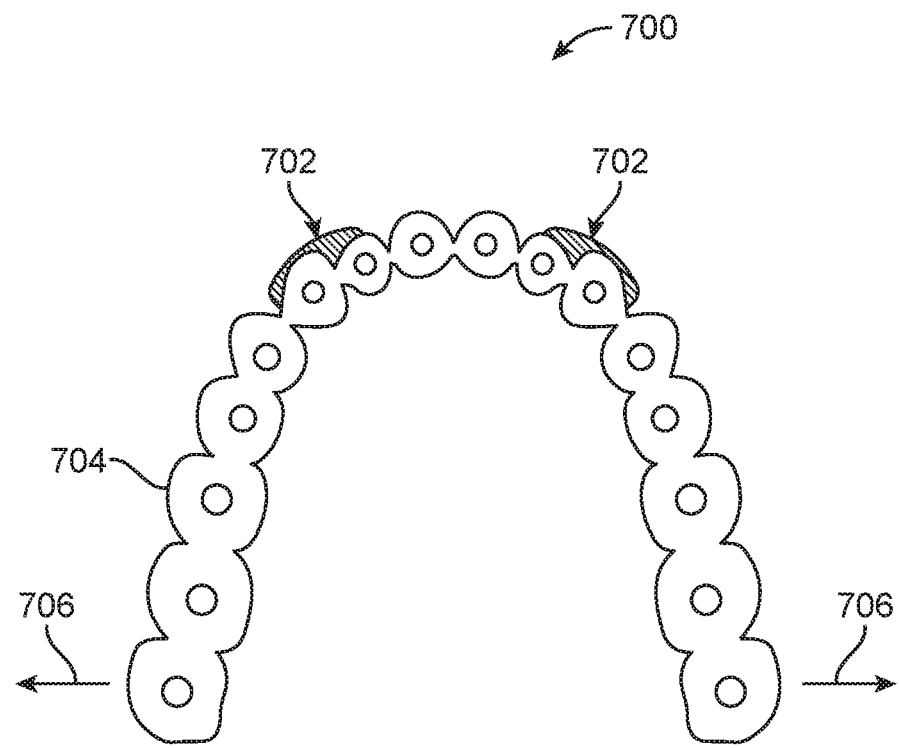
FIG. 7 illustrates an appliance with one or more thickened ribs for increased stiffness, in accordance with embodiments.

FIG. 7 illustrates an appliance 700 with one or more thickened ribs 702 for increased stiffness, in accordance with embodiments. The ribs 702 can be built integrally into the appliance shell 704 using the direct fabrication methods described herein. The number, geometry, and configuration of the ribs 702 can be configured to increase the stiffness of the appliance at certain locations. For example, in the depicted embodiment, the ribs 702 are positioned on the buccal surface of the shell 704 near the canines and extend longitudinally along the mesial-distal axis. This can be beneficial for reducing flexing of the shell 704 near the canines when modifying the width of the arch, e.g., by moving the molars and/or biscuspids buccally or lingually (see, e.g., arrows 706). It shall be appreciated that in alternative embodiments, the ribs 702 can be positioned at other locations on the shell 704, e.g., on a lingual surface, occlusal surface, near the anterior teeth, near the posterior teeth, etc., in order to increase the stiffness of the appliance at those locations.

Figure 8:
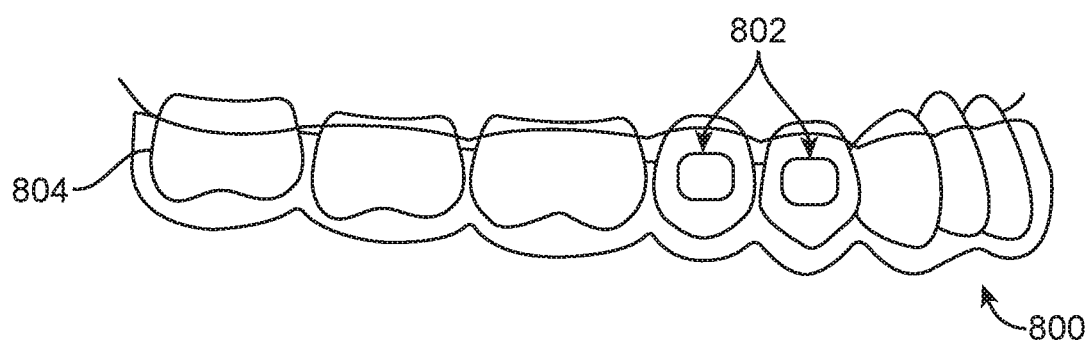
FIG. 8 illustrates an appliance with a plurality of thinner regions for reduced stiffness, in accordance with embodiments.

FIG. 8 illustrates an appliance 800 with a plurality of thinner regions 802 for reduced stiffness, in accordance with embodiments. The thinner regions 802 can be formed integrally in the shell 804 using the direct fabrication methods described herein. In some embodiments, the thinner regions 802 are formed in the buccal surface of the shell 804 as recesses that extend only partially through the thickness of the shell 804. In alternative embodiments, the regions 802 form openings in the shell 804 that extend through the entire thickness of the shell 804. The number, geometry, and configuration of the regions 802 can be configured to selectively reduce the stiffness of the appliance at certain locations. For instance, one or more thinner regions 802 can be formed on a buccal surface, on a lingual surface, occlusal surface, near the anterior teeth, near the posterior teeth, or combinations thereof.

In some embodiments, variations in stiffness and/or other material properties of the appliance can be achieved independently from the appliance geometry. For example, it may be desirable in some instances to produce a variable stiffness appliance while maintaining a substantially uniform appliance thickness. In such embodiments, this can be achieved by varying the degree of photopolymerization of different portions of the appliance during the direct fabrication process. As discussed further herein, some embodiments of the direct fabrication methods herein involve curing a photopolymer by irradiation with light in order to selectively polymerize the photopolymer and thereby build up the appliance geometry. The extent to which each appliance portion is polymerized can be controlled by modifying the curing parameters, which include but are not limited to curing time, power, spacing, and/or depth. In some embodiments, portions of the appliance exhibiting a greater degree of photopolymerization have increased stiffness and modulus compared to portions exhibiting a lesser degree of photopolymerization. Control of photopolymerization allows for the production of variable stiffness appliances without varying the appliance geometry (e.g., thickness) or material composition. However, it shall be appreciated that although certain embodiments herein describe control of appliance stiffness using variable photopolymerization, other approaches disclosed herein such as variable thicknesses and/or variable material compositions can also be used to achieve similar results, and that such approaches can be combined with or substituted for any of the photopolymerization-based approaches described herein.

Figure 9:
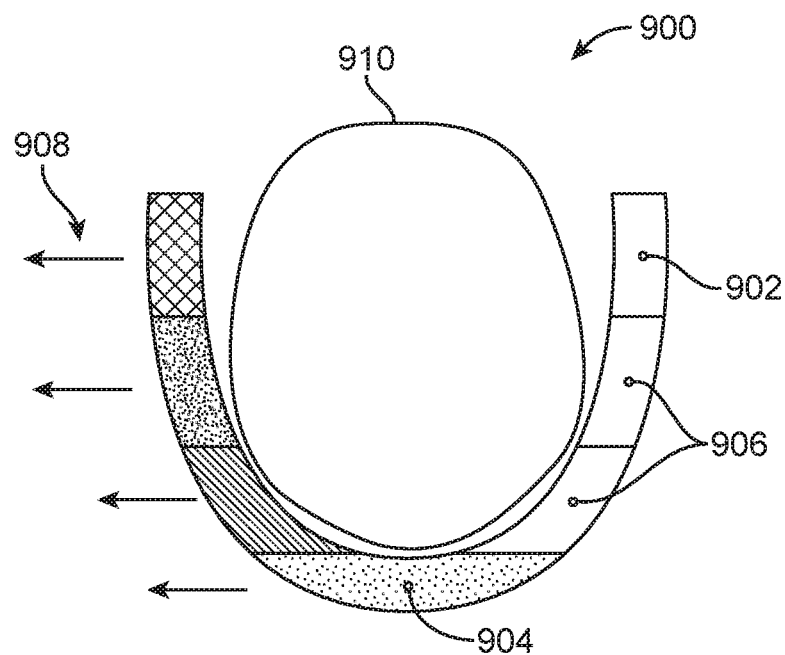
FIG. 9 shows a cross-sectional view of an appliance shell with varying degrees of photopolymerization, in accordance with embodiments.

FIG. 9 shows a cross-sectional view of an appliance shell 900 with varying degrees of photopolymerization, in accordance with embodiments. The shell 900 includes a stiff portion 902 having a relatively high stiffness, an intermediate portion 904 having an intermediate stiffness, and an elastic portion 906 having a relative low stiffness. In some embodiments, the differing stiffnesses of the portions 902, 904, and 906 is achieved by varying the degree of photopolymerization in each of the portions. The portions 902, 904, and 906 can be arranged such that the shell 900 is stiffer towards the gingival portion and softer towards the occlusal surface. For example, in the depicted embodiment, the stiff portion 902 is located near the gingival portion of the shell 900, the elastic portion 906 is located near the occlusal portion of the shell 900, and the intermediate portion 904 is positioned between the stiff portion 902 and the elastic portion 906. The configuration of the shell 900 can result in a variable force profile 908 applied to the received tooth 910 in which the magnitude of the force vectors decreases moving from the gingival portion of the tooth 910 to the occlusal portion of the tooth 910. The force profile 908 can be advantageous for eliciting root translation of the tooth 910 without using attachments.

Figure 10:
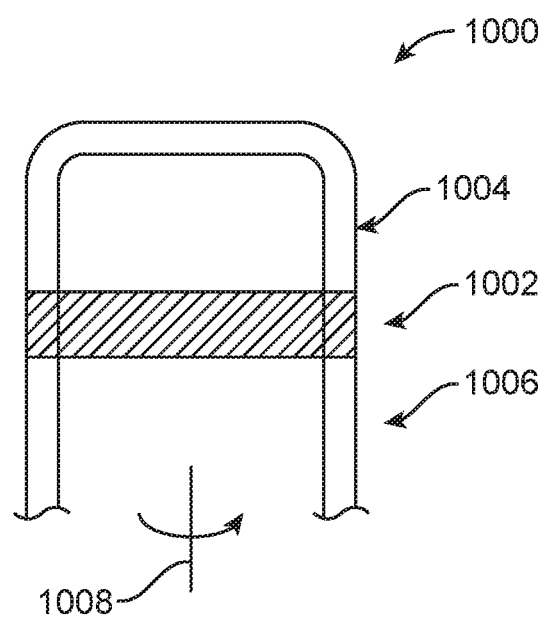
FIG. 10 shows a cross-sectional view of an appliance shell configured for tooth rotation, in accordance with embodiments.

FIG. 10 shows a cross-sectional view of an appliance shell 1000 configured for tooth rotation, in accordance with embodiments. The shell 1000 can include a stiff band 1002 positioned between an occlusal elastic section 1004 and a gingival elastic section 1006 and extending along the buccal and/or lingual surfaces of a received tooth. In some embodiments, the stiff band 1002 is configured with a programmed rotation when the shell 1000 is worn on a tooth, while the surrounding elastic sections 1004, 1006 have a lower stiffness and are not configured with programmed rotation. Accordingly, during use, displacement occurs primarily at the elastic sections 1004, 1006 rather than at the stiff band 1002. The combination of such features within a single shell 1000 can be used to apply moment or torque onto the tooth in order to produce a rotation of the tooth, e.g., about the axis 1008, with a greater working range than if the shell 1000 were made of a single material with homogeneous properties.

Figure 11A:
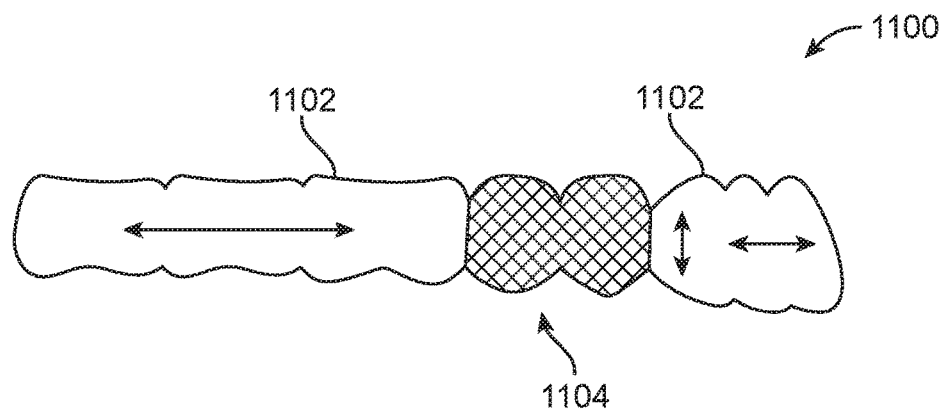
FIG. 11A illustrates an appliance with a plurality of force isolated segments, in accordance with embodiments.

FIG. 11A illustrates an appliance 1100 with a plurality of force isolated segments 1102, in accordance with embodiments. The segments 1102 are joined to each other by an elastic portion 1104. In some embodiments, the segments 1102 are stiffer than the elastic portion 1104, and the varying stiffnesses can be produced by direct fabrication photopolymerization control, variations in thickness, and/or variations in material composition, as discussed herein. By separating the segments 1102 with the elastic portion 1104, the forces exerted by the respective segments can be isolated from each other, thus permitting independent force application on different groups of teeth. Although the depicted embodiment shows two segments 1102 joined by a single elastic portion 1104, it shall be appreciated that the number of segments and elastic portions can be varied as desired. Furthermore, although the depicted embodiment shows segments that are separated horizontally along an anterior-posterior direction, it shall be appreciated that the approaches herein are equally applicable to segments separated along other directions, such as segments separated vertically along an occlusal-gingival direction.

Figure 11B:
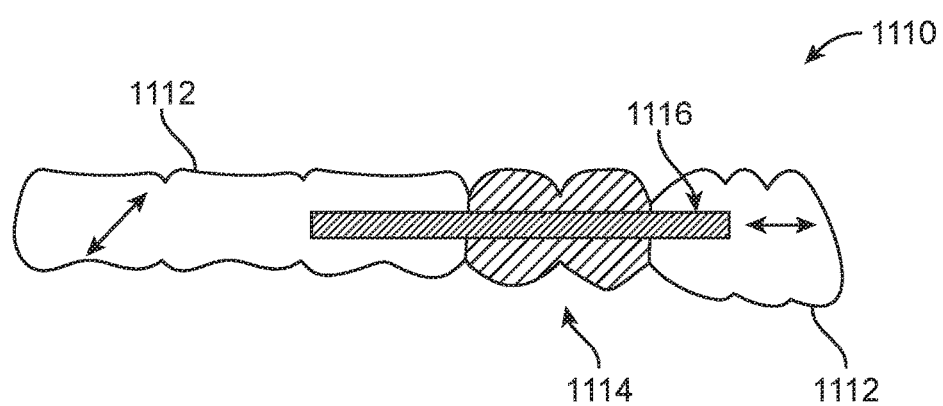
FIG. 11B illustrates an appliance configured for force transfer between a plurality of force isolated segments, in accordance with embodiments.

FIG. 11B illustrates an appliance 1110 configured for force transfer between a plurality of force isolated segments 1112, in accordance with embodiments. Similar to the appliance 1100, the segments 1112 are joined to each other by a relatively elastic portion 1114, and this configuration isolates the forces generated by the respective segments. In some embodiments, it may be desirable to provide some amount of force transfer between the segments 1112. This can be achieved by coupling the segments 1112 to each other by a connector 1116, depicted herein as a bar or band. The connector 1116 can have a stiffness greater than that of the elastic portion 1114. The stiffness of the connector 1116 can be greater than or less than the stiffness of the segments 1112, as desired. The connector 1116 can be used to isolate forces from the teeth received in the elastic portion 1114 while permitting the transfer of selected forces between the teeth received by segments 1112.

Figure 11C:
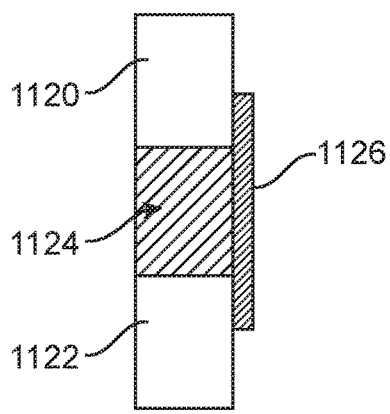
FIG. 11C illustrates an exemplary force transfer configuration, in accordance with embodiments.

FIG. 11C illustrates an exemplary force transfer configuration, in accordance with embodiments. Similar to the other embodiments herein, the configuration includes a first segment 1120 and second segment 1122 separated by an elastic portion 1124. A connector 1126 is used to couple the first and second segments 1120, 1122 to each other. The connector 1126 can also be coupled along its length to the elastic portion 1124 in order to permit some transfer of force to the elastic portion 1124.

Figure 11D:
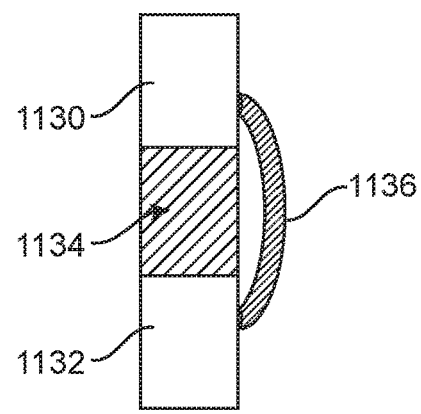
FIG. 11D illustrates another exemplary force transfer configuration, in accordance with embodiments.

FIG. 11D illustrates another exemplary force transfer configuration, in accordance with embodiments. Similar to the other embodiments herein, the configuration includes a first segment 1130 and second segment 1132 separated by an elastic portion 1134. A connector 1136 is used to couple the first and second segments 1130, 1132 to each other. The connector 1136 can be separated from the elastic portion 1134 so as to isolate the elastic portion 1134 from the forces produced by the first and second segments 1130, 1132.

Figure 11E:
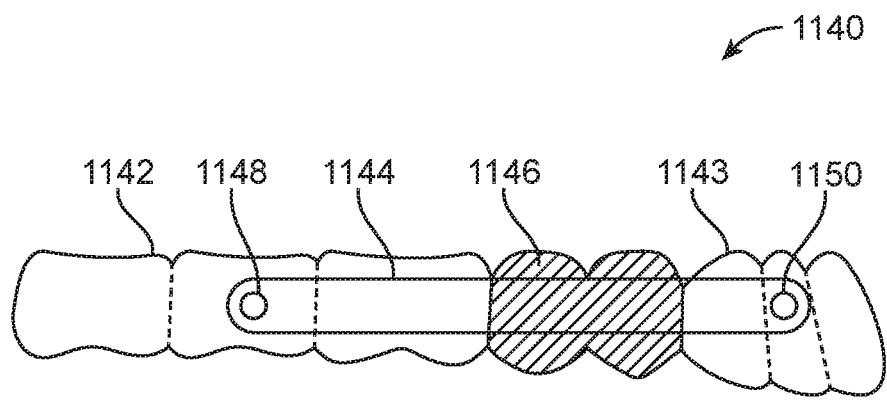
FIG. 11E illustrates an appliance with a plurality of segments used in combination with an elastic, in accordance with embodiments.

FIG. 11E illustrates an appliance 1140 with a plurality of segments 1142, 1143 used in combination with an elastic 1144, in accordance with embodiments. Similar to the other embodiments discussed herein, the segments 1142, 1143 can be joined to each other by an elastic portion 1146 in order to isolate groups of teeth from each other. The elastic 1144 is respectively coupled to a first segment 1142 at a first coupling point 1148 and to a second segment 1143 at a second coupling point 1150, such that the length of the elastic 1144 spans the elastic portion 1146 and is aligned with the anterior-posterior axis of the appliance 1140. The elastic 1144 can be permanently or removably coupled to the segments 1142, 1143 in a variety of ways, e.g., using fasteners, hooks, adhesives, and the like. In alternative embodiments, the appliance 1140 can be formed with a built-in elastic 1144 such that no separate coupling step is needed, as discussed further herein.

In some embodiments, the appliance 1140 is configured such that the elastic 1144 is placed in tension when it is coupled to the segments 1142, 1143 via the coupling points 1148, 1150. Accordingly, the elastic 1144 exerts tensile forces on the segments 1142, 1143 that pull them towards each other. These forces can be transmitted to the teeth received by the segments 1142, 1143 in order to move them towards each other, e.g., to close a space between the teeth, retract a group of teeth, and so on. The use of an elastic portion 1146 to isolate groups of teeth to be moved can provide an increased working range for the elastic 1144.

Figure 11F:
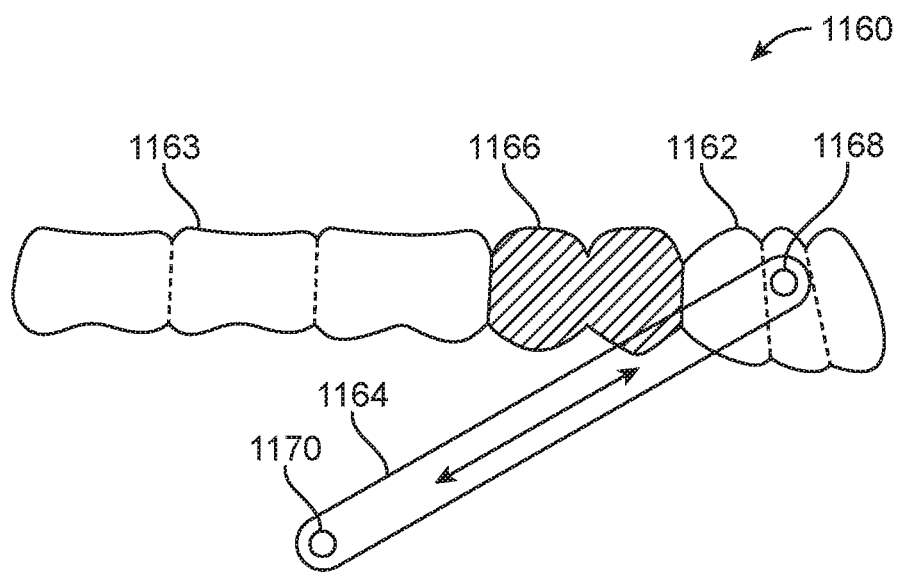
FIG. 11F illustrates an appliance with a plurality of segments used in combination with an elastic, in accordance with embodiments.

FIG. 11F illustrates an appliance 1160 with a plurality of segments 1162, 1163 used in combination with an elastic 1164, in accordance with embodiments. Similar to the other embodiments herein, the segments 1162, 1163 are joined to each other by an elastic portion 1166. The elastic 1164 is coupled to one of the segments 1162 at a first coupling point 1168 and to a location on the patient's opposing jaw at a second coupling point 1170. For example, the second coupling point 1170 of the elastic 1164 can be attached to another appliance worn on the opposing jaw, a tooth-mounted attachment on a tooth on the opposing jaw, an anchoring device positioned in bone of the opposing jaw, or combinations thereof. The elastic 1164 may be placed in tension when coupled to the segment 1162 and the opposing jaw, and the tensile forces can be applied onto the teeth received by the segment 1162 in order to elicit movements of the teeth (e.g., retraction). The elastic portion 1166 can isolate the forces applied onto the teeth received by the segment 1163 from the forces applied to the teeth received by the segment 1162, such that the tensile forces exerted by the elastic 1164 act primarily on the teeth received by the segment 1162 and have little or no effect on the teeth received by the segment 1163. This approach can be used, for example, to isolate one or more anterior teeth from one or more posterior teeth, or vice-versa.

In some embodiments, appliances with heterogeneous properties as discussed herein can be produced by forming the appliance from a plurality of different materials. In some embodiments, different types of material are used to form different portions of the appliance, and the different properties of the different material types can each contribute to the properties of the resultant appliance. The materials used to fabricate an appliance can vary from each other with respect to one or more of color, translucency, elastic modulus, surface strength, biocompatibility, and/or curing properties, to name a few. For instance, a relatively stiff or rigid material can be deposited at locations where increased stiffness is desired, and a relatively elastic material can be deposited at locations where increased elasticity is desired. Alternatively, rather than forming each appliance portion from a single material type, multiple materials can be combined and used to form an appliance portion. The amounts and/or types of materials used can determine the properties of the corresponding appliance portion. In some embodiments, multiple materials can be mixed or otherwise combined with each other in order to form a composite that exhibits superior properties compared to the individual materials. The amounts and/or types of materials used in the composite can control the resultant properties (e.g., stiffness) of the composite. Accordingly, appliances with heterogeneous properties as discussed herein can be produced by using different composites to form different portions of the appliance.

The arrangement (or topology) of multiple materials in an appliance can be varied as desired. For example, multiple materials can be formed on an appliance in discrete sections, compartments, or layers. Alternatively, the multiple materials can be formed as a continuous mixture such that individual material types are not compartmentalized. The locations where different material types are formed can be varied as desired. For instance, portions of the appliance adjacent the gingiva may be formed from a softer or more elastic material than portions adjacent the teeth, or vice-versa. As another example, portions of the appliance adjacent the interproximal regions of the teeth may be formed from a softer or more elastic material than portions away from the interproximal regions, or vice-versa. In another example, interior portions of the appliance near the teeth may be formed from a softer or more elastic material than exterior portions away from the teeth, or vice-versa. In yet another example, portions of the appliance used to engage and apply forces to teeth (e.g., directly or indirectly via an attachment) may be formed from a softer or more elastic material than portions that do not engage the teeth, or vice-versa. In yet another example, portions of the appliance used to engage other appliances or devices (e.g., elastics, springs, wires, etc.) may be formed from a softer or more elastic material than portions that do not engage other appliances or devices, or vice-versa.

The multi-material approaches described herein permit the fabrication of heterogeneous appliances without varying the geometry (e.g., thickness) and/or photopolymerization parameters of the appliance. However, it shall be appreciated that although certain embodiments herein describe control of appliance stiffness using variable material compositions, other approaches disclosed herein such as variable photopolymerization and/or variable thicknesses can also be used to achieve similar results, and that such approaches can be combined with or substituted for any of the multi-material approaches described herein.

Figure 12A:
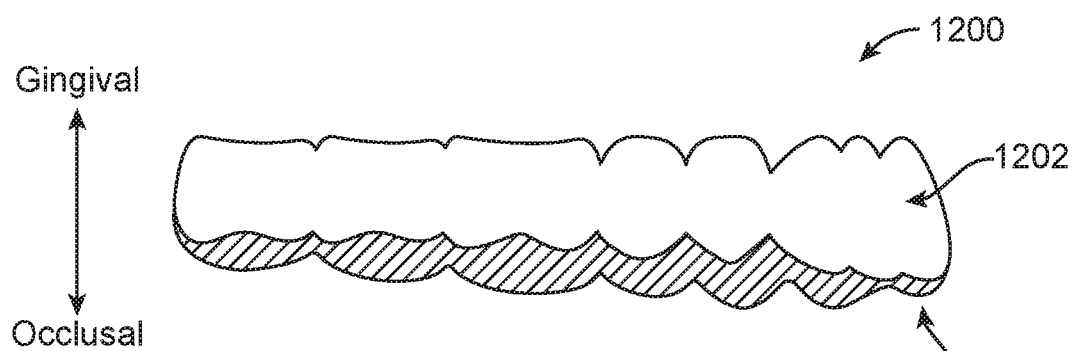
FIG. 12A illustrates an appliance with different materials used for the occlusal portion and gingival portion, in accordance with embodiments.

FIG. 12A illustrates an appliance 1200 with different materials used for the occlusal portion 1202 and gingival portion 1204, in accordance with embodiments. Based on the properties of the respective materials used, the occlusal portion 1202 can have a greater stiffness than the gingival portion 1204, or vice-versa. The material properties for each of the portions can be determined based on the desired functionalities for the occlusal and gingival portions. For example, in some embodiments, the occlusal portion 1202 can be formed from a relatively soft or elastic material, while the gingival portion 1204 can be formed from a relatively hard or stiff material. In such embodiments, the relatively elastic occlusal portion 1202 can act as a "chewy" that the patient can bite down on in order to facilitate proper seating of the appliance 1200 on the patient's teeth. Moreover, the use of a relatively elastic occlusal portion 1202 can potentially reduce the extent of posterior open bite caused by wearing the appliance 1200, as well as provide improved engagement of the appliance 1200 with the patient's teeth with less interference from the occlusal surfaces. Alternatively, the occlusal portion 1202 can be formed from a relatively hard or stiff material and the gingival portion 1204 can be formed from a relatively soft or elastic material. This configuration can be advantageous for improving durability of the occlusal surfaces, e.g., in order to resist wear due to bruxism, allow the patient to consume certain foods while wearing the appliance 1200, etc.

Figure 12B:
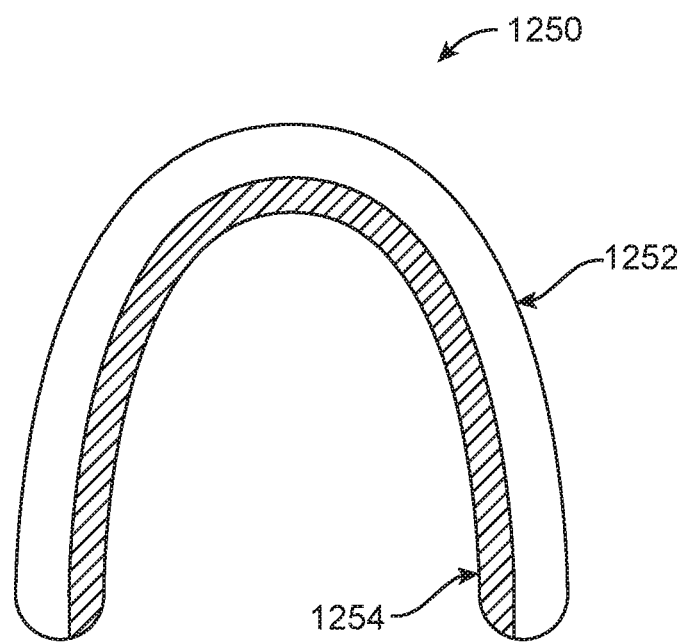
FIG. 12B illustrates an appliance with different materials used for the buccal portion and lingual portion, in accordance with embodiments.

FIG. 12B illustrates an appliance 1250 with different materials used for the buccal portion 1252 and lingual portion 1254, in accordance with embodiments. Based on the properties of the respective materials used, the buccal portion 1252 can have a greater stiffness than the lingual portion 1254, or vice-versa. The material properties for each of the portions can be determined based on the desired functionalities for the buccal and lingual portions. For example, in some embodiments, the buccal portion 1252 can be formed from a relatively soft or elastic material, while the lingual portion 1254 can be formed from a relatively hard or stiff material. Optionally, the buccal portion 1252 can be formed from a clear material for improved aesthetics, while the lingual portion 1254 is not readily visible and therefore does not need to be formed from a clear material. In some embodiments, the relative stiffness of the buccal portion 1252 is advantageous for improving engagement of the appliance 1250 with tooth-mounted attachments, as such attachments are frequently positioned on the buccal surfaces of teeth. The relative stiffness of the lingual surface can exert forces for producing tooth movements in a buccal direction, e.g., for arch expansion.

In some embodiments, it can be advantageous to design an appliance exhibiting variable stiffness along different directions. The stiffness of an appliance portion along a vertical direction, horizontal direction, lateral direction, mesial-distal direction, anterior-posterior direction, occlusal-gingival direction, and/or buccal-lingual direction may differ from the stiffness of the appliance portion along a vertical direction, horizontal direction, lateral direction, mesial-distal direction, anterior-posterior direction, occlusal-gingival direction, and/or buccal-lingual direction. The variable directional stiffness can allow for different forces to be preferentially applied along certain directions. For instance, it may be desirable to apply more force along an anterior-posterior direction and less force along an intrusion or extrusion direction, or vice-versa. As another example, it may be desirable to apply one force on the left side of an appliance and a different force on the right side of the appliance. In another example, it may be desirable to apply a larger rotation force on one tooth (e.g., a molar) and a smaller rotation force on an adjacent tooth (e.g., a bicuspid). Variable force application along different directions can be achieved using any of the methods presented herein, including varying the thickness, degree of photopolymerization, and/or material composition.

Figure 13:
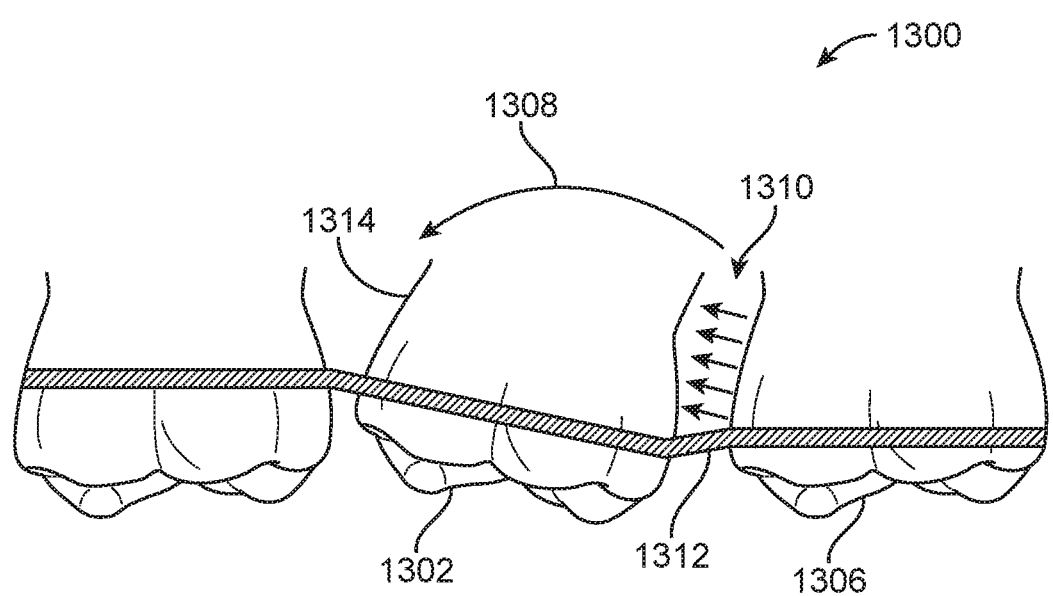
FIG. 13 illustrates an appliance with variable stiffness along different directions for uprighting a tooth, in accordance with embodiments.

FIG. 13 illustrates an appliance 1300 with variable stiffness along different directions for uprighting a tooth 1302, in accordance with embodiments. The appliance 1300 can be configured to create a "root first tipping chain" in which adjacent teeth 1304, 1306 flanking the tooth 1302 provide anchorage for exerting tipping forces onto the tooth 1302 in order to move the tooth 1302 into a more upright position, e.g., along the movement path indicated by arrow 1308. In some embodiments, the appliance 1300 includes an appliance shell (not shown) with cavities to receive the tooth 1302 and the adjacent anchor teeth 1304, 1306. The shell can be formed with clearance space around the target tooth 1302 in order to accommodate the uprighting movement of the tooth 1302. The shell can be shaped to engage the tooth 1302 in order to exert transverse forces 1310 to upright the tooth 1302. Additionally, the appliance 1300 can include a stiff band of material 1312 that spans the tooth 1302 and the adjacent anchor teeth 1304, 1306. The geometry and location of the stiff band 1312 can be configured to alter the center of rotation 1314 of the tooth 1302 in order to produce the uprighting movement. For example, the stiff band 1312 can be shaped according to the geometry of the tooth 1302 in order to move the center of rotation 1314 for a given translational movement towards the occlusal surface of the tooth. This approach can fix the occlusal surface of the tooth crown at a specified location, and the translational force applied to the tooth 1302 thus rotates the entire tooth 1302 about the specified location. In some embodiments, by changing the center of rotation 1314, the tooth 1302 can be moved in a "root first" fashion in which repositioning of the tooth root precedes repositioning of the tooth crown. In some embodiments, a root first movement involves a translational movement of the tooth root greater than translational movement of the tooth crown.

In some embodiments, the use of variable stiffness appliances as described herein can be used to reduce or eliminate unwanted pairings of movements and/or forces that may occur. For example, tooth movements such as root control movements, tipping, and the like may cause unwanted intrusion or extrusion of the target tooth and/or surrounding teeth. In some embodiments, unwanted movements and/or forces can be reduced or eliminated by varying the directional stiffness of the appliance using the methods provided herein (e.g., variable stiffness, variable material properties, variable material compositions, etc.). An appliance with varying directional stiffnesses may exhibit anisotropic properties, such that the stiffness along one direction may differ from the stiffness along at least one other direction, for example. In some embodiments, the appliance is configured with an increased stiffness in one or more directions along a desired tooth movement and a reduced stiffness in one or more directions along an undesired tooth movement (e.g., away from the desired tooth movement) in order to preferentially elicit the desired movement while reducing or eliminating the undesired movement.

FIGS. 14A through 14C schematically illustrate reductions in unwanted pairing of movements using varying directional stiffnesses, in accordance with embodiments. FIG. 14A illustrates an appliance portion 1400 that is relatively stiff along a transverse direction 1402 and relatively elastic along a vertical direction 1404 in order to elicit transverse tooth movements (e.g., translation) while reducing or eliminating unwanted vertical movements (e.g., extrusion or intrusion). Alternatively, if vertical movements are desired while transverse movements are unwanted, the relative stiffnesses can be reversed so that the portion 1400 exhibits increased stiffness along the vertical direction 1404 and reduced stiffness along the transverse direction 1402. FIGS. 14B and 14C illustrate top and side views, respectively, of an appliance portion 1410 that is relatively stiff in a rotational direction 1412 and relatively elastic along a vertical direction 1414 in order to produce tooth rotation or torsion while reducing or eliminating unwanted vertical movements (e.g., extrusion or intrusion). The configuration can be reversed if vertical movements are desired while rotational movements are undesired, such that the portion 1410 is relatively elastic along the rotational direction 1412 and relatively stiff along the vertical direction 1414.

Although the orthodontic appliances with variable properties herein have been described primarily in the context of variable stiffness, thickness, and/or material composition, it shall be appreciated that an orthodontic appliance may exhibit variations in other properties as well, such as one or more of hardness, strength, compressibility, stress relaxation, hydrophobicity/hydrophilicity, Poisson ratio, strain rate, viscoelasticity, or polarity, to name a few. For example, an appliance can be fabricated with heterogeneous hydrophobicity/hydrophilicity, e.g., with hydrophilic inner surfaces (e.g., surfaces near the received teeth) in order to improve appliance wetting and grip on the teeth, and with hydrophobic outer surfaces (e.g., away from the received teeth) in order to reduce saliva diffusion and stress relaxation. The direct fabrication methods herein can be used to produce appliances exhibiting complex and heterogeneous combinations of many different material properties.

Orthodontic Appliances with Integrally Formed Components

Orthodontic treatment with fixed repositioning devices, such as braces, may be used in conjunction with auxiliary components, devices, or accessories to achieve desired end results. Such auxiliary components may take a variety of forms ranging from readily available traditional accessories to specially created devices. Auxiliary components may be mounted on fixed, non-removable devices or they may be part of a removable appliance typically worn prior to the application of the fixed devices. Similarly, it may be desired to utilize auxiliary components when repositioning teeth with removable tooth repositioning appliances, such as the shell appliances described herein. In some embodiments, such auxiliary components are affixed to a shell appliance after the shell appliance has been initially fabricated (e.g., by thermoforming).

The direct fabrication approaches presented herein can be used to produce orthodontic appliances with various types of built-in components, also referred to herein as an "integrally formed component" or an "integrally formed feature." Examples of integrally formed components include, but are not limited to: a hook, button, groove, slit, slide block, slide column, slide cylinder, corrugation, undercut, internal structure, hole, connection, snap, bevel, mating, guide, channel, block, recess, cavity, chamber, scaffold, layer, a coating, or any other structure or feature as described in U.S. Patent Publication No. 2007/0231765, U.S. Pat. No. 8,641,414, and U.S. Patent Publication No. 2011/0269092, the disclosures of which are incorporated herein by reference in their entirety. An integrally formed component can include or be designed to substitute for one or more of the following auxiliary components: elastics, wires, springs, bars, arch expanders, palatal expanders, twin blocks, occlusal blocks, bite ramps, mandibular advancement splints, bite plates, pontics, hooks, brackets, headgear tubes, bumper tubes, palatal bars, frameworks, pin-and-tube apparatuses, buccal shields, buccinator bows, wire shields, lingual flanges and pads, lip pads or bumpers, protrusions, divots, or any other structure or feature suitable for use in conjunction with the appliances herein to treat a patient. The direct fabrication methods provided herein allow such auxiliary components to be integrally formed with an appliance shell, as discussed further below.

As used herein, an "integrally formed component" or "integrally formed feature" may refer to a component formed as a single unitary or monolithic piece with the appliance shell, such that the component cannot be separated from the appliance without damaging or destroying the appliance. An integrally formed component may be differentiated from a component that is formed and/or provided separately from the shell and is subsequently coupled to the shell (e.g., by adhesives, fasteners, etc.). In some embodiments, an integrally formed component is concurrently formed with the shell in a single manufacturing or fabrication step, such that the same fabrication machine and/or fabrication process is used to produce both the component and the shell. Accordingly, an integrally formed component may be differentiated from a component that is formed prior to or after the shell is formed, and may be differentiated from a component that is formed using a different fabrication process than the process used to form the shell. For example, the various direct fabrication methods discussed herein can be used to produce both the appliance shell and the integrally formed component concurrently in a single fabrication step.

In some embodiments, an integrally formed component of an orthodontic appliance may be an orthodontic component or accessory. Orthodontic components or accessories can include but are not limited to accessories typically used with fixed, non-removable orthodontic devices. For example, headgear tubes are accessories typically mounted on traditional braces for inserting a headgear device and applying extraoral force to the teeth and jaws. Tubes for receiving headgear may be integrally formed in the shell of an appliance for a similar effect. Similarly, orthodontic hooks may be mounted on traditional braces to support elastic bands which may also apply distinct forces to the teeth and jaws. As with headgear tubes, such hooks may also be integrally formed in the shell of a shell appliance for a similar effect. Likewise, a number of other accessories, such as brackets, springs, bumper tubes, palatal bars, frameworks, pin-and-tube apparatuses and the like, may be integrally formed into shell appliances. In some embodiments, such as with brackets, the accessory may be used to join a removable shell appliance with a portion of teeth supporting fixed conventional devices, such as braces. An orthodontic component or accessory coupled to an appliance via integrally formed mounting features can be configured to interact with any other orthodontic appliances present in the patient's mouth.

In some embodiments, an integrally formed component may be an orthodontic component or accessory that is primarily exclusive to removable appliances. These components may not be suited for use with fixed appliances and devices, e.g., due to their bulk and size. In some embodiments, such components are used prior to the use of fixed devices to create a favorable environment for later tooth repositioning. For example, when a patient's teeth are still erupting, a number of features may be used to foster improved eruption and development of the tooth arrangement and bite configuration. These may include buccal shields, buccinator bows or wire shields, bite plates, palatal expanders and bars, lingual flanges and pads, lip pads or bumpers, and the like. Since these components are currently used with removable appliances, they are ideally suited for use with the appliances described herein. Accordingly, the features may be integrally formed in the polymeric shell of an appliance. Similarly, supporting structures for such components may also be integrally formed in the shell for the removable application of a component. For example, a bumper tube may be embedded in the polymeric shell for later insertion and removal of a bumper.

In some embodiments, an appliance may be directly fabricated with an integrally formed component such that use of the appliance comprising the integral component provides orthodontic therapy in conjunction with other types of dental and periodontal therapies (e.g., to improve oral health, for cosmetic purposes, etc.) which may be desired or required by the patient. In addition, producing the orthodontic appliance comprising the integrally formed component in a single fabrication step can eliminate additional steps that were previously required in order to attach an auxiliary component to an appliance, and can therefore streamline manufacturing. Benefits of streamlined manufacturing include reduced cost, reduced number of steps, fewer materials, faster production, and reduced rates of error, among others. Additionally, available geometries, types of materials that could be used, types of components that could be formed, location of the components within the appliance, and the like are broader with an integrally formed component compared to those previously considered for an externally attached component. Often, the resolution by which an integrally formed component can be designed and fabricated is more precise compared to externally attached components.

An added advantage of the use of appliances comprising integrally formed components is the ability to provide the conventional benefit of the auxiliary component while simultaneously repositioning the teeth. In fixed appliance treatment, for example, the fixed appliance may preclude the ability to simultaneously use auxiliary components provided as removable appliances since removable appliances may not be readily applied with fixed appliances in place. For example, situations in which it is desired to control eruption of specific teeth concomitant with repositioning of the same or other teeth may be difficult to achieve with fixed appliances.

Accordingly, systems, methods, and devices for orthodontic appliances with an integrally formed component are provided herein. The component can be any structure or feature formed into an appliance shell of the apparatus for facilitating attachment of the appliance shell to an additional device. Often the integrally formed component is shaped to engage with, receive, couple to, connect with, and/or mate with a complementary shape of a patient's tooth or an additional appliance or a portion thereof. As described further herein, such components can include, but are not limited to a hook, button, groove, slit, slide block, slide column, slide cylinder corrugation, undercut, internal structure, hole, connection, snap, bevel, mating, guide, channel, block, recess, cavity, chamber, scaffold, layer, coating, and the like. As used herein, "integrally formed feature" may refer to a feature formed as a single unitary or monolithic piece with another appliance component (e.g., an appliance shell with teeth receiving cavities), such that the feature cannot be separated from the appliance without damaging or destroying the appliance component.

During a course of orthodontic treatment, it may be desired or necessary to apply a force to a patient's teeth to generate movement of one or more teeth to bring the patient's teeth into a better occlusion. Tooth movements that may be generated by the appliances herein include but are not limited to tipping, torquing, rotating, translating, extruding, or intruding. In many instances, it may not be possible to generate desired levels of such a force solely through the use of a shell appliance without any additional auxiliary component, feature, component, characteristic or the like. Thus, in some embodiments, the forces generated by such a shell are supplemented by the forces produced by an integrally formed component. In some embodiments, integrally formed components are used to increase an amount of force applied to the teeth, decrease an amount of force applied to the teeth, and/or change the distribution of force applied to the teeth, relative to the force(s) exerted by the appliance in the absence of such components.

In one aspect, a method for fabricating an orthodontic appliance comprising an integrally formed component is provided. The method can comprise: determining a movement path to move one or more teeth from an initial arrangement to a target arrangement; determining an appliance geometry for an orthodontic appliance comprising a shell and one or more integrally formed components, wherein the shell comprises a plurality of teeth receiving cavities shaped to move the one or more teeth from the initial arrangement to the target arrangement; and generating instructions for direct fabrication of the orthodontic appliance, wherein the instructions are configured to cause direct fabrication of the shell using a first material and direct fabrication of the one or more integrally formed components using a second, different material.

In some embodiments, the first material differs from the second material with respect to one or more of the following: stiffness, elastic modulus, hardness, thickness, strength, compressibility, stress relaxation, hydrophobicity, hydrophilicity, Poisson ratio, strain rate, viscoelasticity, or polarity.

In some embodiments, the method further comprises: determining a first material composition for the shell, the first material composition comprising the first material; and determining a second material composition for the integrally formed component, the second material composition comprising the second material.

In some embodiments, the direct fabrication technique is an additive manufacturing technique or a subtractive manufacturing technique. The additive manufacturing technique can comprise one or more of: vat photopolymerization, material jetting, binder jetting, material extrusion, powder bed fusion, sheet lamination, or directed energy deposition.

In some embodiments, the one or more integrally formed components comprise or are designed to substitute for an elastic, a wire, or a spring.

In some embodiments, the one or more integrally formed components comprise or are designed to substitute for an arch expander, a palatal expander, or a palatal bar.

In some embodiments, the one or more integrally formed components comprise or are designed to substitute for a twin block, an occlusal block, a bite ramp, an advancement structure, or a bite plate.

In some embodiments, the one or more integrally formed components are shaped to couple between a first portion and a second portion of the shell.

In some embodiments, the shell is shaped to be worn on a jaw of the patient and the one or more integrally formed components are shaped to couple to an appliance worn on an opposing jaw of the patient.

In some embodiments, the one or more integrally formed components comprise one or more mounting features shaped to couple to an auxiliary component.

In another aspect, a system for fabricating an orthodontic appliance comprising an integrally formed component is provided. The system can comprise one or more processors configured with instructions to: determine a movement path to move one or more teeth from an initial arrangement to a target arrangement; determine an appliance geometry for an orthodontic appliance comprising a shell and one or more integrally formed components, wherein the shell comprises a plurality of teeth receiving cavities shaped to move the one or more teeth from the initial arrangement to the target arrangement; and generate instructions for direct fabrication of the orthodontic appliance, wherein the instructions are configured to cause direct fabrication of the shell using a first material and direct fabrication of the one or more integrally formed components using a second, different material.

In some embodiments, the first material differs from the second material with respect to one or more of the following: stiffness, elastic modulus, hardness, thickness, strength, compressibility, stress relaxation, hydrophobicity, hydrophilicity, Poisson ratio, strain rate, viscoelasticity, or polarity.

In some embodiments, the one or more processors are further configured with instructions to: determine a first material composition for the shell, the first material composition comprising the first material; and determine a second material composition for the integrally formed component, the second material composition comprising the second material.

In some embodiments, the direct fabrication technique is an additive manufacturing technique or a subtractive manufacturing technique. The additive manufacturing technique can comprise one or more of: vat photopolymerization, material jetting, binder jetting, material extrusion, powder bed fusion, sheet lamination, or directed energy deposition.

In some embodiments, the one or more integrally formed components comprise or are designed to substitute for an elastic, a wire, or a spring.

In some embodiments, the one or more integrally formed components comprise or are designed to substitute for an arch expander, a palatal expander, or a palatal bar.

In some embodiments, the one or more integrally formed components comprise or are designed to substitute for a twin block, an occlusal block, a bite ramp, an advancement structure, or a bite plate.

In some embodiments, the one or more integrally formed components are shaped to couple between a first portion and a second portion of the shell.

In some embodiments, the shell is shaped to be worn on a jaw of the patient and the integrally formed component is shaped to couple to an appliance worn on an opposing jaw of the patient.

In some embodiments, the one or more integrally formed components comprise one or more mounting features shaped to couple to an auxiliary component.

In another aspect, an appliance for repositioning teeth of a patient is provided. The appliance can comprise: a shell forming a plurality of cavities shaped to receive teeth of a mouth of the patient; and a component, wherein the component is integrally formed within the shell.

In some embodiments, the integrally formed component is configured to interact with the same portion of the shell where the component is integrally formed, or with another portion of the shell that is different from the portion of the shell where the component is integrally formed.

In some embodiments, the integrally formed component is configured to interact with a shell, a tooth, a plurality of the patient's teeth, a dental device, or an orthodontic device that is different from the shell where the component is integrally formed.

In some embodiments, the integrally formed component is directly connected to an orthodontic appliance.

In some embodiments, the integrally formed component is indirectly connected to an orthodontic appliance.

In some embodiments, the integrally formed component is directly or indirectly connected to another portion of the shell or directly connected to a portion of a different shell.

In some embodiments, the integrally formed component is a hook, a button, an advancement structure, a guide path, or a protrusion.

In some embodiments, the integrally formed component is a window, a channel, a hole, or a recession.

In some embodiments, the integrally formed component is a mandibular advancement structure, e.g., for treating sleep apnea.

In some embodiments, the integrally formed component is useful for rotating, tipping, translating, intruding, extruding, or torquing the patient's tooth.

In some embodiments, the integrally formed feature is useful for expanding a patient's arch width, reducing open bite, or reducing grinding of the patient's teeth.

In some embodiments, the integrally formed component comprises a mounting feature shaped to engage an auxiliary component.

In some embodiments, the appliance is generated by a fabrication machine according to a set of fabrication instructions, the fabrication instructions comprising the steps of: generating a digital model of the shell, the digital model including the feature integrally formed into the shell, and; fabricating the shell having the feature integrally formed into the shell.

In another aspect, a method for fabricating an appliance comprising an integrally formed component is provided. The method can comprise: generating a digital model of the appliance, the digital model comprising a digital representation of a shell comprising a plurality of teeth receiving cavities and a digital representation of a component integrally formed within the shell; and generating instructions for fabricating the appliance with the shell and integrally formed component using a direct fabrication technique, based on the digital model.

In some embodiments, the direct fabrication technique is an additive manufacturing technique or a subtractive manufacturing technique. The additive manufacturing technique can comprise one or more of: vat photopolymerization, material jetting, binder jetting, material extrusion, powder bed fusion, sheet lamination, or directed energy deposition.

In some embodiments, the instructions are configured to control a fabrication machine to form the component concurrently with the shell.

In another aspect, a method for fabricating an appliance comprising an integrally formed component is provided. The method can comprise: determining a movement path to move one or more teeth from an initial arrangement to a target arrangement; determining an appliance geometry comprising an integrally formed component for an orthodontic appliance configured to move the one or more teeth from the initial arrangement to the target arrangement; and generating instructions for fabrication of the orthodontic appliance having the appliance geometry comprising the integrally formed component.

In some embodiments, the method further comprises: determining a force system to produce movement of the one or more teeth along the movement path; and determining an appliance geometry comprising an integrally formed component for an orthodontic appliance configured to produce the force system.

Figure 15:
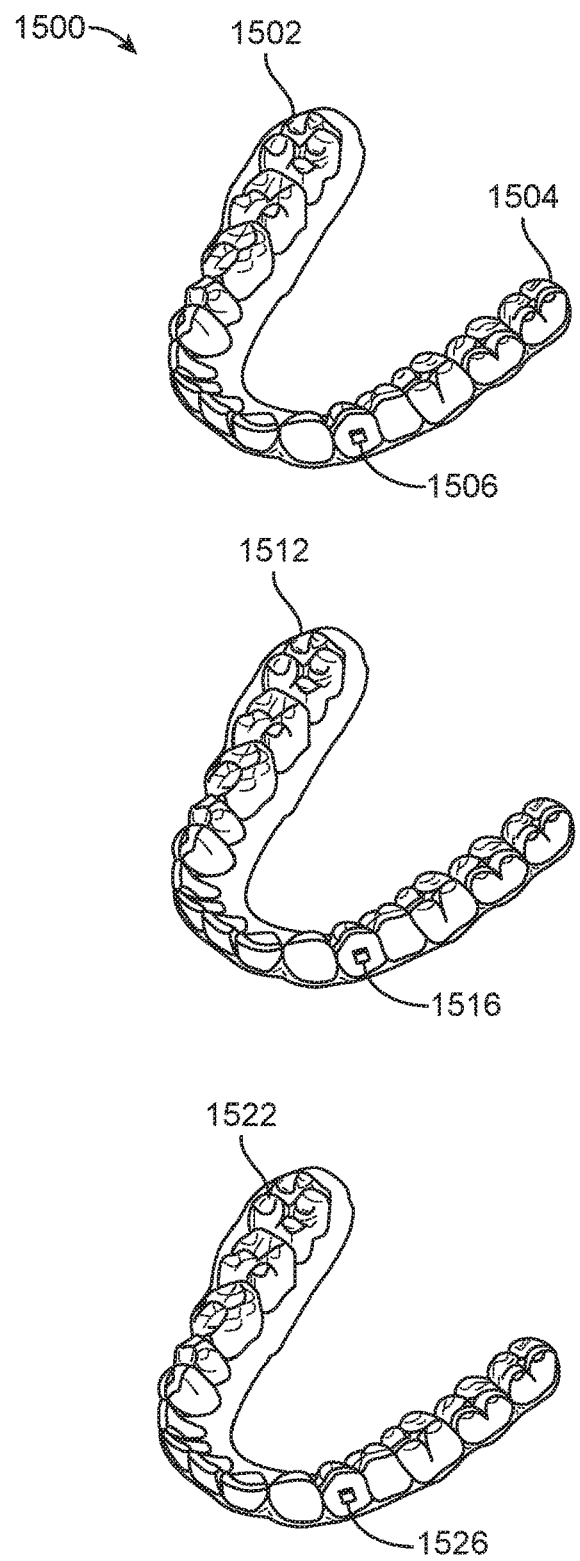
FIG. 15 illustrates a tooth repositioning system, in accordance with embodiments.

FIG. 15 illustrates a tooth repositioning system 1500, in accordance with embodiments. The tooth repositioning system 1500 includes an orthodontic appliance 1502 comprising a shell 1504 with an integrally formed component 1506. The orthodontic appliance 1502 can be provided as part of an orthodontic tooth repositioning system 1500. Any of the appliances described herein can be designed and/or provided as part of a set of a plurality of appliances used in a tooth repositioning system 1500. The component 1506 may be integrally formed in any position within the shell 1504 of the appliance 1502 such the component 1506 is configured to enhance the patient's treatment plan. Placement of the component 1506 within the shell 1504 may be designed as a part of the patient's treatment plan so as to achieve the intermediate or final tooth arrangement intended for the appliance 1502. For example, the tooth receiving system 1500 can include a first appliance 1502 corresponding to an initial tooth arrangement with a first integrally formed component 1506 within the shell 1504 of the appliance at a first location, one or more intermediate appliances 1512 corresponding to one or more intermediate arrangements having an intermediate integrally formed component 1516 within the shell of the appliance, and a final appliance 1522 with a final integrally formed component 1526 within the shell of the appliance corresponding to a target arrangement. Each of the appliances (the first appliance, any of the intermediate appliances, the final appliance) can comprise a corresponding integrally formed component (e.g., first, intermediate, final), a plurality of integrally formed components, or no integrally formed components. The integrally formed component can be integrally formed within the shell of the appliance at a different location or at the same location as the preceding appliance or as the subsequent appliance. While the components depicted in FIG. 15 are of the same location, shape, and size, integrally formed components of the appliances of the system 1500 may be at any location of any appliance and can have any shape or any size, as described herein and in accordance with the patient's treatment plan. An exemplary, but not limiting, location of an integrally formed component 1506, 1516 and 1526 is depicted in the appliances 1502, 1512 and 1522. A target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Any appliance for use at one or more of the incremental repositioning stages of the tooth repositioning system may include an integrally formed component. A method for designing a tooth repositioning system includes, but is not limited to, planning a placement of the integrally formed component within any of the appliances of the tooth repositioning system used during one or more of the incremental repositioning stages, planning the number of appliances to comprise an integrally formed component for use during one or more of the incremental repositioning stages, planning the order of use of appliances comprising an integrally formed components, and the like.

Various types of integrally formed components are suitable for incorporation with the appliances described herein. An integrally formed component may have any of a plurality of geometries, including shapes, dimensions, angles, and the like. Shapes of an integrally formed component can include, but are not limited to, a circle, an oval, an ellipse, a curved structure with a complex shape, a triangle, a square, a rectangle, a triangle, a polygon, a pentagon, a hexagon, a heptagon, and the like. The integrally formed component may have walls which are straight or curved. The walls of the integrally formed component may form angles with each other, or may smoothly transition into each other (e.g., via a curved join surface).

The position and/or orientation of an integrally formed component can be varied as desired. For example, a position of the component can include, but is not limited to, a lingual surface of the appliance, an occlusal surface of the appliance, a buccal surface of the appliance, a gingival portion of the appliance, an interior surface of the appliance (e.g., near the received teeth), an exterior surface of the appliance (e.g., away from the received teeth), an anterior portion of the appliance, a posterior portion of the appliance, a distal portion of the appliance, a mesial portion of the appliance, or the like, or combinations thereof. The component can be oriented away from or towards one or more of the following: a lingual surface of the appliance, an occlusal surface of the appliance, a buccal surface of the appliance, a gingival portion of the appliance, an interior surface of the appliance (e.g., near the received teeth), an exterior surface of the appliance (e.g., away from the received teeth), an anterior portion of the appliance, a posterior portion of the appliance, a distal portion of the appliance, a mesial portion of the appliance, or the like, or combinations thereof.

An integrally formed component may be located in a single plane (e.g., x-plane, y-plane, z-plane) of the appliance, or may be located in a plurality of planes in the appliance. Optionally, the integrally formed component may project from one or more planes in the appliance and/or recess through one or more planes in the appliance. In some embodiments, the component can be contained wholly within the interior of the appliance such that no portion is directly exposed to the intraoral environment (e.g., a slit, a channel, a recess, a hole or the like or as described herein). In some embodiments, the component can be partially or not contained within the interior of the appliance such that one or more portions are directly exposed to the intraoral environment (e.g., a hook, a button, a bevel, a ridge, an edge, a flap, a block or the like or as described herein). The location of the integrally formed component may be determined during treatment planning, during fabrication, or as part of any other method described herein. In some embodiments, the placement of the integrally formed component depends upon the material from which the component is formed, such materials as discussed herein or known to one of ordinary skill in the art.

In some embodiments, the integrally formed component is located at one or more of a plurality of positions within an appliance shell. The plurality of positions may include one or more of: a lingual surface, an occlusal surface, a buccal surface, a gingival portion, an interior surface (e.g., near the received teeth), an exterior surface (e.g., away from the received teeth), an anterior portion, a posterior portion, a distal portion, a mesial portion, or the like, or combinations thereof. In some embodiments, an appliance shell includes one or more walls defining teeth-receiving cavities (occlusal, buccal, and/or lingual walls) and the component can be formed partially or wholly within the wall(s) and/or lie on a single shared plane as the wall(s). The integrally formed component may be positioned such that the longest axis of the integrally formed component aligns with or does not align with the mesial-distal axis, posterior-anterior axis, and/or vertical axis of the shell. Alternatively, the integrally formed feature may be positioned such that the longest axis of the integrally formed feature does not align with the mesial-distal axis, posterior-anterior axis, and/or vertical axis of the shell. In some embodiments, an integrally formed component in an appliance shell can be positioned to engage a target (e.g., a tooth, another intraoral appliance) in order to affect force applied by the appliance to the target.

The dimensions (e.g., length, width, height, surface area, volume, etc.) of an integrally formed component can be configured as desired. In some embodiments, the dimensions are selected based on one or more of the following: the shape of the integrally formed component, the use of the integrally formed component in the patient's treatment plan, the dimensions of the patient's mouth, and/or the dimensions of other appliances or intraoral devices located in the patient's mouth.

The material composition of an integrally formed component may be the same as the rest of the appliance (e.g., the appliance shell), or may be different from the rest of the appliance. For example, in some embodiments, an appliance shell is directly fabricated from a first material, and an integrally formed component is fabricated from a second, different material. The first material can differ from the second material with respect to any of the properties described herein, including but not limited to stiffness, elastic modulus, hardness, thickness, strength, compressibility, stress relaxation, hydrophobicity, hydrophilicity, Poisson ratio, strain rate, viscoelasticity, and/or polarity. Direct fabrication of an orthodontic appliance including a shell produced from a first material and an integrally formed component produced from a second, different material can be performed according to the methods described further herein.

In some embodiments, an integrally formed component is used to add strength and/or additional force to an appliance. The integrally formed component can be a reinforcement structure (e.g., a corrugation) arranged to stiffen the appliance against deflection. For example, a corrugation can be used to stiffen the gingival edge of an orthodontic appliance against lateral deflection induced, for example, by the force from a coupled elastic. In some embodiments, the integrally formed reinforcement structure is positioned to apply additional force to one or more teeth received by the appliance. The integrally formed reinforcement structure can be located such that the force is applied along a desired direction. An orthodontic appliance can have a reinforcing structure formed in one or more of a gingival edge, buccal surface, lingual surface, occlusal surface, interior surface, or exterior surface of the appliance. The reinforcing structure can be integrally formed with the shell by direct fabrication of the appliance, as described herein.

Figure 16:
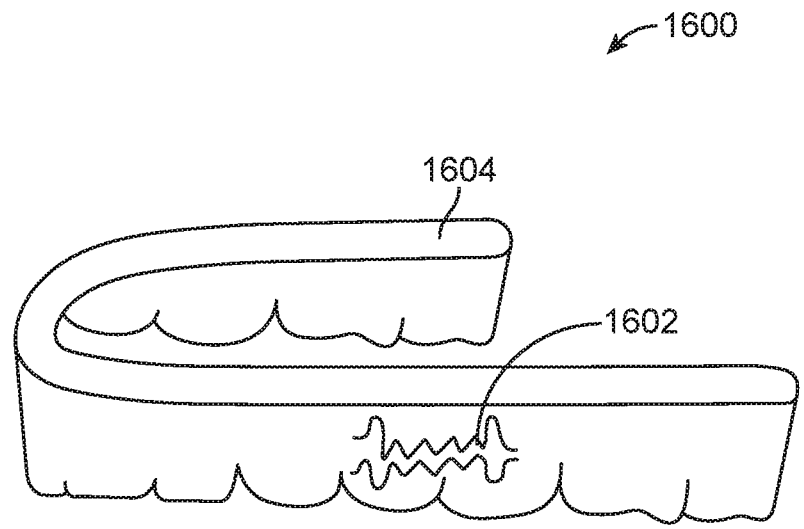
FIG. 16 illustrates an orthodontic appliance with an integrally formed reinforcing structure, in accordance with embodiments.

FIG. 16 illustrates an orthodontic appliance 1600 with an integrally formed reinforcing structure, in accordance with embodiments. As illustrated in FIG. 16, a corrugation 1602 is integrally formed into an appliance shell 1604 to provide additional strength, tensile force, or the like to a portion of the teeth positioned within the tooth receiving cavities of the shell 1604. The integrally formed corrugation can be located so as to apply force to the teeth in the desired direction. The location, length, thickness, and amount of corrugation used may be varied throughout the embodiments described herein.

Although components formed by addition of material to tooth repositioning appliances may perform useful functions in orthodontic treatment, in some embodiments, it may also be beneficial to form components by removing material in an appliance, e.g., in order to form hollow portions or windows. For example, hollow portions may be formed in one or more walls of an appliance shell in order to reduce weight of the appliance (e.g., may be beneficial for patients with sensitivities to the appliances) and to reduce the cost of the appliance. The size and geometry of the hollow portion can be varied as desired in order to achieve weight reduction while maintaining strength. Optionally, internal support structures may be added to the hollow areas to add strength such as struts or the like which provide additional support to the surrounding portions of the shell wall around the hollow portion. Support structures can be of any size, geometry, angle or location as described herein. The support structures can increase the strength and/or stiffness of the appliance. An appliance with integrally formed hollow portions and/or support structure can be produced by direct fabrication, as described herein.

Figure 17:
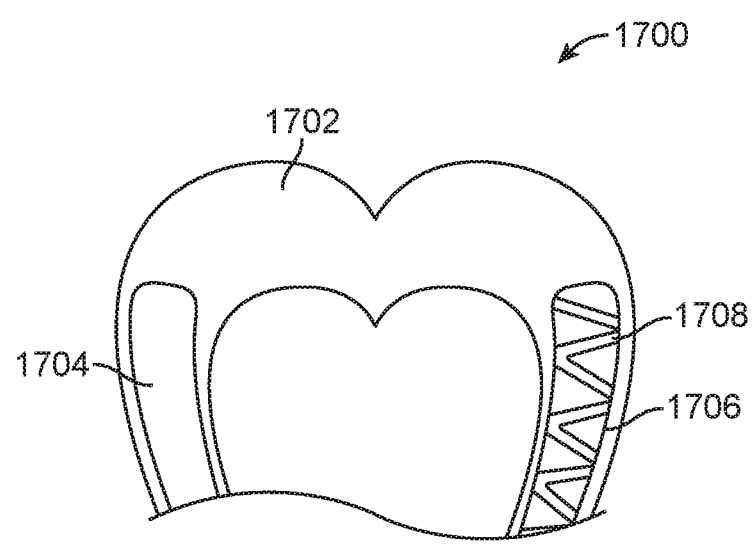
FIG. 17 illustrates an orthodontic appliance with integrally formed hollow portions, in accordance with embodiments.

FIG. 17 illustrates an orthodontic appliance 1700 with integrally formed hollow portions, in accordance with embodiments. The appliance 1700 may have a shell 1702 defining one or more tooth receiving cavities, and one or more hollow portions 1704, 1706 can be formed in the shell wall, e.g., to reduce weight of the appliance 1700. Optionally, internal support structures 1708 such as struts or the like may be integrally formed within the hollow portions (e.g., hollow portion 1706) to add strength and provide additional support to the surrounding portions of the shell wall around the hollow portion.

In some embodiments, an appliance can be integrally formed with one or more apertures (e.g., windows) to expose at least a portion of a received tooth or teeth. Such apertures may be formed by omitting or removing portions of the wall of the appliance shell. In such embodiments, when the shell is positioned over the patient's teeth, portions of the teeth beneath the apertures may be exposed, such as occlusal surfaces, buccal surfaces and/or lingual surfaces. Exposing such tooth surfaces may allow brackets, buttons or other orthodontic components to be utilized in conjunction with the appliance, for example. Advantageously, exposure of the occlusal surfaces in an appropriate size and location may allow for the natural interdigitation of the upper and lower teeth to be maintained during treatment, for example. This may also be achieved with the presence of one or more larger apertures over portions of the occlusal surfaces of the teeth. In such embodiments, segments of the shell may or may not be present across the interproximal regions or spaces between the teeth. In such embodiments, interdigitation of at least portions of the upper and lower teeth may benefit tooth and jaw orientations, leading to improved treatment, appearance, comfort, and consequently patient compliance. Similarly, use of apertures on occlusal surfaces may prevent open bite and may reduce wear and/or abrasion of portions of the appliance and/or portions of the patient's tooth and/or teeth. Likewise, similarly placed apertures may provide the benefits offered by a lower elastic modulus, such that the reduced stiffness may be provided by the absence of the material.

In some embodiments, an integrally formed component is designed to include or substitute for an auxiliary component that would otherwise be coupled to the orthodontic appliance. As discussed above and herein, an integrally formed component can include or be designed to substitute for one or more of the following auxiliary components: elastics, wires, springs, bars, arch expanders, palatal expanders, twin blocks, occlusal blocks, bite ramps, mandibular advancement splints, bite plates, pontics, hooks, brackets headgear tubes, springs, bumper tubes, palatal bars, frameworks, pin-and-tube apparatuses, buccal shields, buccinator bows, wire shields, lingual flanges and pads, lip pads or bumpers, protrusions, divots, or any other structure or feature suitable for use in conjunction with the appliances herein to treat a patient.

For example, the appliances herein can include integrally formed components configured for treating sleep apnea (e.g., obstructive sleep apnea (OSA)) in a patient by displacing the lower jaw (mandible) of the patient anteriorly relative to the upper jaw (maxilla), also known as "mandibular advancement." For example, an appliance can comprise integrally formed occlusal structures (e.g., advancement structures, twin blocks, etc.), which can be configured such that the anterior-posterior force exerted on the teeth by the appliance during mandibular advancement does not cause tooth repositioning or does not exceed a predetermined amount of force, e.g., an amount that would cause tooth repositioning and/or patient discomfort.

Often, appliances for treating sleep apnea are designed to be worn on the upper and lower jaws. In some embodiments, the appliance for treating sleep apnea in a patient comprises an appliance shell comprising a plurality of cavities shaped to receive teeth of a jaw of the patient and an integrally formed advancement structure arranged to interact with an opposing jaw of the patient so as to displace the lower jaw anteriorly relative to the upper jaw. The appliances described herein can further comprise a second appliance shell comprising a second plurality of cavities shaped to receive teeth of the opposing jaw. The advancement structure can interact with the opposing jaw via engagement with a second advancement structure of the second appliance shell. For example, the advancement structure comprises a first protrusion extending from the appliance shell and having a first engagement surface, and the second advancement structure comprises a second protrusion extending from the second appliance shell and having a second engagement surface configured to engage the first engagement surface. The first protrusion can be shaped to mate with the second protrusion. An inclination angle of the first and second engagement surfaces can be determined based on one or more of anatomy of the patient's jaw, kinematic data of the patient's jaw, or a targeted distance for the displacement. In some embodiments, the advancement structure comprises a first coupling element and the second advancement structure comprises a second coupling element, the first and second coupling elements configured to interact with each other so as to reversibly bias the advancement structure and second advancement structure toward predetermined relative positions. The first and second coupling elements can comprise magnetic elements, elastic tethers, mating features, or combinations thereof, for instance.

Figure 18:
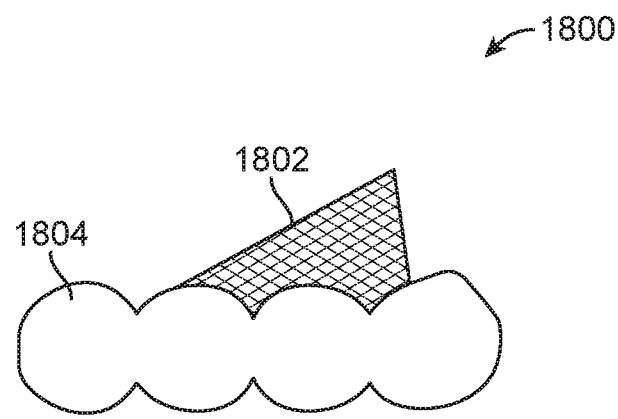
FIG. 18 illustrates an orthodontic appliance with an integrally formed occlusal block, in accordance with embodiments.

FIG. 18 illustrates an appliance 1800 with an integrally formed occlusal structure 1802 on the occlusal surface of the appliance shell 1804, in accordance with embodiments. The geometry and positioning of the occlusal structure 1802 can be configured according to the particular functionality of the appliance 1800. For example, the occlusal structure 1802 can be shaped and positioned to serve as a twin block, occlusal block, bite ramp, or advancement structure. In some embodiments, the occlusal structure 1802 is shaped to engage a complementary structure on an appliance worn on the patient's opposing jaw in order to adjust the patient's bite, e.g., along an anterior-posterior direction and/or left-right direction. Optionally, the occlusal structure 1802 can includes features matching the features of the patient's occlusal surfaces, e.g., occlusal features of the opposing arch. In some embodiments, the built-in occlusal structure 1802 is formed from a different material than the shell 1804 using the direct fabrication approaches herein. For example, the occlusal structure 1802 can be formed from a stiffer material than the shell 1804 in order to provide improved durability against bruxing.

Figure 19:
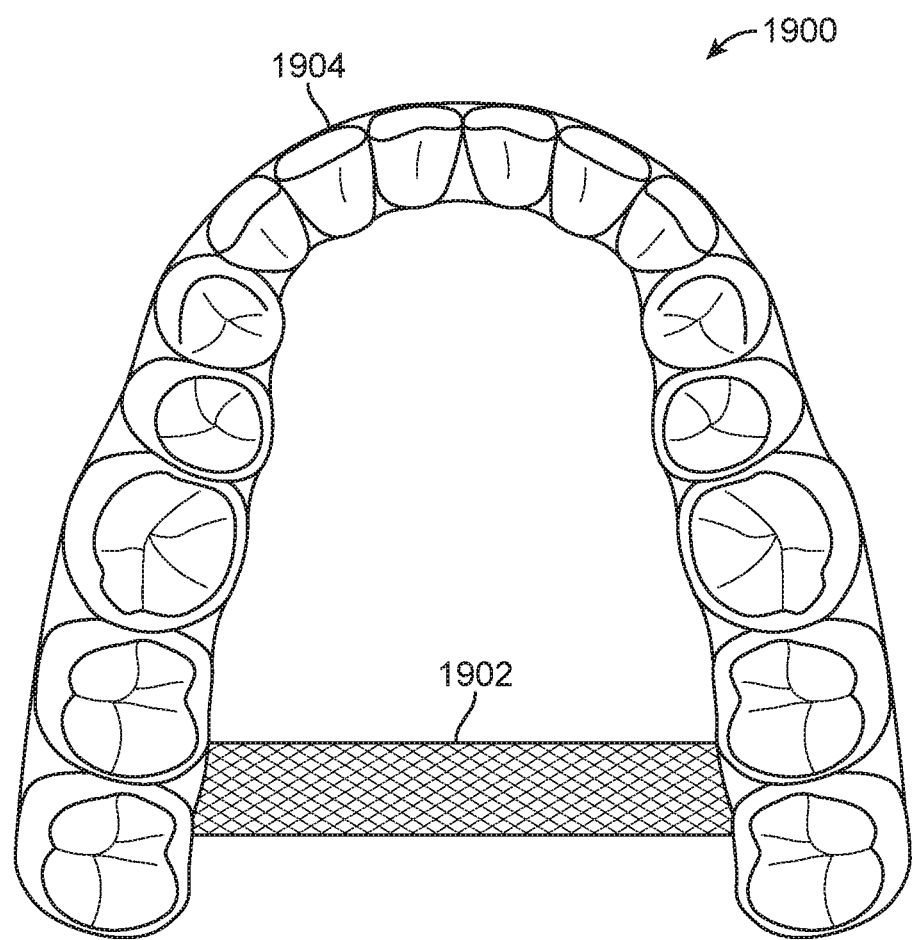
FIG. 19 illustrates an orthodontic appliance with an integrally formed arch expander, in accordance with embodiments.

FIG. 19 illustrates an appliance 1900 with an integrally formed arch expander 1902 on the lingual surface of the appliance shell 1904, in accordance with embodiments. The arch expander 1902 can be coupled to the posterior portions of the shell 1904 in a position spanning the patient's palate in order to exert forces along a buccal direction to expand the patient's arch. The arch expander 1902 may be placed into a compressed configuration when the appliance 1900 is worn by the patient in order to produce the arch expansion forces. In some embodiments, the built-in arch expander 1902 is formed from a different material than the shell 1904 using the direct fabrication approaches herein. For example, the arch expander 1902 can be fabricated from a relatively stiff and/or expandable material in order to produce buccally-directed forces for expanding the width of the patient's arch.

Figure 20:
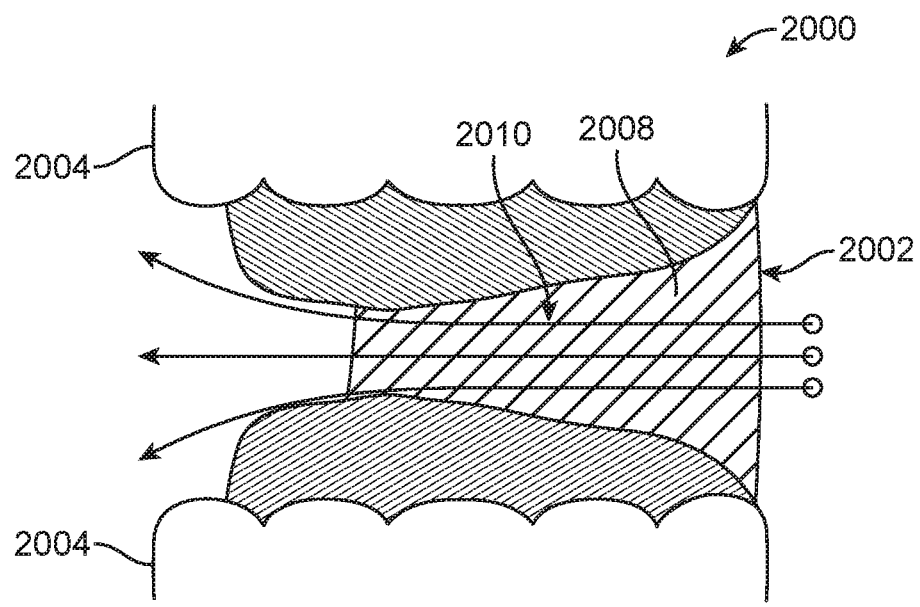
FIG. 20 illustrates an orthodontic appliance with an integrally formed air flow structure, in accordance with embodiments.

FIG. 20 illustrates an appliance 2000 with an integrally formed flow structure 2002 on an upper shell 2004 and a lower shell 2006, in accordance with embodiments. The air flow structure 2002 can be coupled to the occlusal surfaces of the upper shell 2004 and lower shell 2006 such that the structure 2002 is positioned between the patient's upper and lower arches when the appliance 2000 is worn. The air flow structure 2002 includes a passage 2008 extending through the interior of the structure 2002 along an anterior-posterior direction in order to provide an unobstructed conduit for air flow through the appliance 2000 (see, e.g., arrows 2010). The passage 2008 can be shaped to promote easier breathing when the appliance is worn, e.g., using computational fluid dynamics to model air flow. The direct fabrication approaches provided herein enable precise control over the geometry of the built-in air flow structure 2002, thus improving the extent to which fluid dynamics characteristics of the appliance 2000 can be customized and optimized. In some embodiments, the appliance 2000 can be used as a mouth guard to protect the received teeth from trauma while permitting mouth breathing through the air flow structure 2002. In such embodiments, the upper shell 2004, lower shell 2006, and/or air flow structure 2002 can be formed from relatively soft or elastic materials that serve as padding to protect the patient's teeth.

Figure 21:
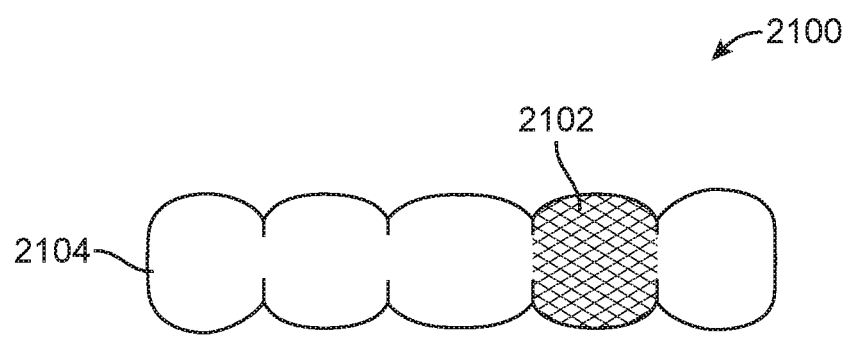
FIG. 21 illustrates an orthodontic appliance with an integrally formed pontic, in accordance with embodiments.

FIG. 21 illustrates an appliance 2100 with an integrally formed pontic 2102 in the appliance shell 2104, in accordance with embodiments. The pontic 2102 can be provided to replace one or more missing teeth, e.g., in order to improve the aesthetic appearance of the patient's dentition, as well as to maintain spaces between teeth during treatment. Using the direct fabrication techniques disclosed herein, the pontic 2102 can be integrally formed as a single piece with the shell 2104 using a suitably colored material. The pontic 2102 can be produced by filling a cavity of the shell 2104 with a pontic material, for example. Alternatively, the pontic 2102 can be produced by applying a material to an interior and/or exterior surface of the appliance 2104 in order to create the appearance of a natural tooth. This approach eliminates additional processing steps to fill the shell 2104 with a pontic material or couple a discrete pontic structure, thus simplifying the manufacturing process.

Optionally, an integrally formed component can be an ornamental feature, such as coloring or patterning of an appliance. For example, the direct fabrication approaches can be used to produce appliances with integrally formed ornamental features such as colors, decorative geometries, patterning, embossing, etc., rather than requiring that such ornamental features be added to the appliance in a separate post-processing step. The approaches herein are can be used to produce appliances with patient-customized ornamental features, for example. In some embodiments, software is provided to allow patients to create customized ornamental features.

In some embodiments, an appliance includes an integrally formed inflatable structure such as a bladder or balloon in the appliance shell. The inflatable structure can be formed from a relatively elastic material so as to permit expansion of the inflatable structure when filled with a fluid (e.g., a gas or liquid). The inflatable structure can be positioned at a location on the appliance shell where increased strength and/or stiffness is desired, e.g., to increase an amount of force applied to the teeth at or near the location. The inflatable structure can be inflated with fluid prior to placement or after placement of the appliance on the patient's teeth, as desired. The fluid pressure within the inflatable structure can be varied in order to achieve a targeted amount of strength and/or stiffness. Optionally, the fluid pressure can be adjusted during treatment in order to provide varying amounts of force application onto teeth.

In some embodiments, an appliance includes a built-in layer or coating integrally formed with the appliance shell by direct fabrication. The layer or coating can be located on one or more of a buccal surface, lingual surface, occlusal surface, exterior surface, and/or interior surface of the shell. The layer or coating can be formed from one or more materials configured to provide additional functionality to the appliance. For example, the layer or coating can be formed from a moisture resistant material, e.g., in order to act as a sealant to reduce stress relaxation of the appliance associated with water absorption. As another example, the layer or coating can be formed from a material that resists or reduces staining. In another example, the layer or coating can be used to reduce friction between the appliance, the patient's teeth and/or another device. In some embodiments, a protective layer or coating is integrally formed into the occlusal surfaces of an appliance to protect the appliance, the patient's teeth, and/or another device, e.g., from grinding, pressure, and interference. In yet another example, the layer or coating can incorporate therapeutic agents or functional agents for drug delivery, flavoring, etc. The direct fabrication methods herein allow such layers or coatings to be formed with the shell in a single processing step.

In some embodiments, an integrally formed component may form a spring in the shell of an appliance for use in transmitting repositioning force to one or more teeth, e.g., to reposition teeth from a first arrangement to a successive arrangement. A spring of this type may be of a traditional design or it may be specially designed for use with polymeric shell appliances. Further, it may be specially designed to engage an attachment device mounted on a tooth, which is a device primarily utilized in conjunction with removable shell appliances. In some embodiments, the spring can be comprised of a pre-formed strip or portion of the shell which engages an attachment device mounted on an underlying tooth. The attachment device can be accessible through a window in the appliance as described herein. A full description of exemplary attachment devices is described in PCT Publication No. WO 00/32132, which corresponds to application Ser. No. 09/454,278, assigned to the assignee of the present invention. Both documents are incorporated herein by reference in their entirety for all purposes.

In some embodiments, the integrally formed component can be a larger protrusion useful to provide additional support for the appliance and/or to provide orthodontic functions. Such a protrusion may form a palatal bar. A variety of palatal bars may be formed in the shell, such as a low hanging transpalatal bar for control of vertical dimension. These may provide orthodontic functions similar to conventional palatal bars, and may also provide support for the appliance. This may be particularly useful in highly flexible appliances. The protrusion may be a corrugated palatal bar, e.g., for increased strength and support.

In some embodiments, the integrally formed component may serve as a bite plate. A bite plate is a device which prevents the teeth from closing completely. The resulting open state, or disclusion, may be useful for a number of orthodontic treatments, including crossbite correction and controlled passive eruption. To provide anterior disclusion, an appliance may have an increase in thickness of material in the posterior occlusion regions of the shell, as previously discussed. The increase in thickness of material may be applied to the appliance or formed by the appliance to create a protrusion over the designated occluding surfaces. Similarly, posterior disclusions may be provided by forming a protrusion in the shell which extends at least a portion of an upper palatal region with added thickness, as previously discussed.

In some embodiments, an orthodontic appliance includes an integrally formed component shaped to engage (e.g., receive, couple to, connect with, mate with a complementary shape of, etc.) another portion of the same appliance. For example, an integrally formed component can be located at a first portion (e.g., a buccal portion, a lingual portion, an occlusal portion, a gingival portion, an anterior portion, and/or a posterior portion) of the appliance and can be configured to engage with a second portion (e.g., a buccal portion, a lingual portion, an occlusal portion, a gingival portion, an anterior portion, and/or a posterior portion) of the same appliance. In some embodiments, an integrally formed component used to couple between multiple portions of a single appliance is an elastic, spring, telescoping element, or the like.

Figure 22:
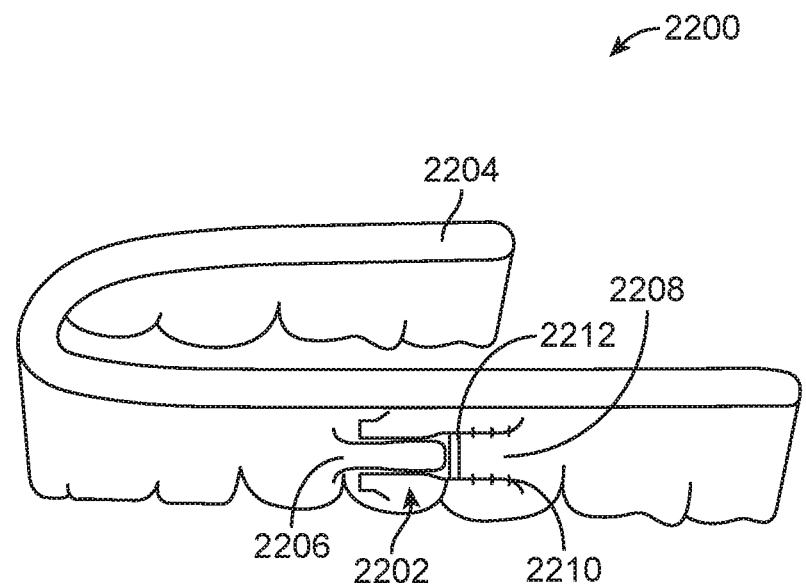
FIG. 22 illustrates an orthodontic appliance with an integrally formed component that couples to another portion of the appliance, in accordance with embodiments.

FIG. 22 illustrates an orthodontic appliance 2200 with an integrally formed component that couples to another portion of the appliance, in accordance with embodiments. In the depicted embodiment, telescoping element 2202 is integrally formed into the appliance shell 2204. The telescoping element 2202 includes a piston 2206 and a recess 2208 shaped to receive and coupled to the piston 2206. By adjusting the length of the piston 2206 received within the recess 2208, telescoping element 2202 can be used to generate variable, amounts of force applied to the teeth received by the appliance shell 2204. Optionally, the recess 2208 can include a plurality of holes 2210 formed in the walls of the recess 2208 and shaped to receive a stop bracket 2212. The stop bracket 2212 can be configured to be positioned and re-positioned throughout the course of treatment in order to adjust the amount of force applied to the patient's jaw by the telescoping element 2202.

In some embodiments, an orthodontic appliance includes an integrally formed component shaped to engage another device. The additional device can be a pin, a button, a screw, an elastic, or an orthodontic appliance, such as a second orthodontic appliance worn by the patient. The additional device can be connected to a tooth, the patient's jaw, a portion of the same appliance, a portion of another appliance, a portion of another integrally formed component of the same appliance, a portion of another integrally formed component of another appliance, and/or a portion of any other orthodontic device in the patient's mouth. For example, a first orthodontic appliance worn on the patient's upper or lower jaw can include an integrally formed component that engages (e.g., couples to) a second orthodontic appliance worn on the patient's opposing jaw. In some embodiments, an integrally formed component can engage with the patient's tooth and/or teeth or a portion thereof, with another appliance or a portion thereof, or the like. Such integrally formed components can be used to increase an amount of force applied to the teeth, decrease an amount of force applied to the teeth, or change the distribution of force applied to the teeth, relative to the appliance in the absence of such components.

As another example, an orthodontic appliance can include an integrally formed component (e.g., an aperture or receptacle) that engages a device attached to a patient's tooth or teeth (e.g., a tooth-mounted attachment device) or otherwise located in the patient's intraoral cavity (e.g., a temporary anchoring device (TAD)). For instance, the integrally formed component can be configured to couple to a TAD or other intraoral device provided in the patient's mouth. The intraoral device may or may not be coupled to a surface of the patient's teeth. In some embodiments, the intraoral device may be, but is not limited to, a retraction screw inserted through the gingival tissue and embedded into a bone of the patient's mouth. The intraoral device (e.g., a TAD) may be embedded into any suitable bone at any suitable location in the patient's mouth, including either buccal and/or lingual facing bone surfaces.

In some embodiments, an integrally formed component may further include structures (e.g., holes, slits, buttons, recesses, etc.) shaped to directly connect to another device, such as by snap fit and/or interference fit, for example. As used herein, "directly connect" may refer to the integrally formed component coupling to the other device without using an intermediary connecting or fastening element, such as an elastic, a wire, a pin, a screw, a spring, adhesive, or the like. Alternatively, the integrally formed component may indirectly connect with the other device. As used herein, "indirectly connect" may refer to the integrally formed component coupling to the other device using an intermediary connecting or fastening element, such as an elastic, a wire, a pin, a screw, a spring, adhesive, or the like.

Figure 23:
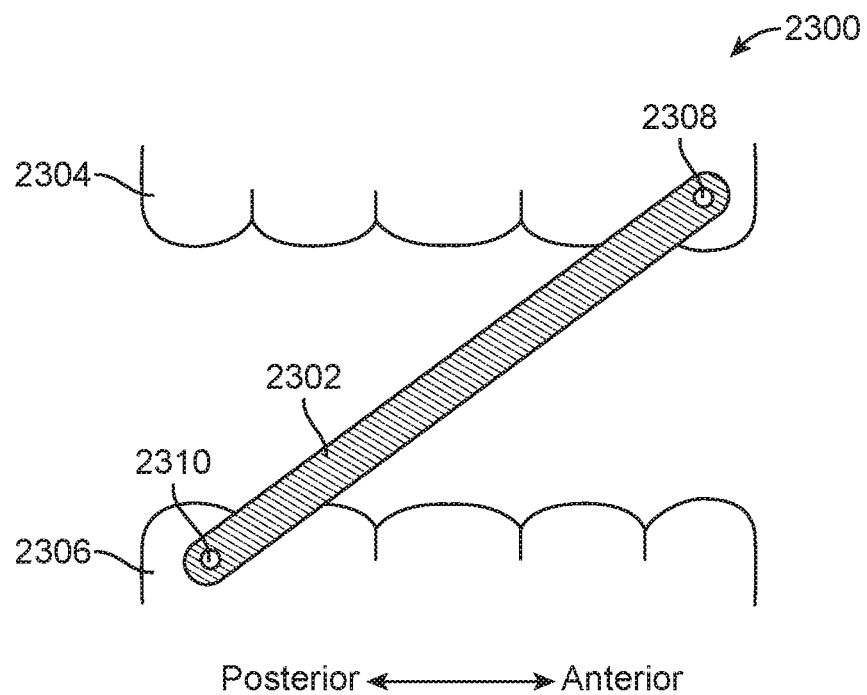
FIG. 23 illustrates an orthodontic appliance with an integrally formed component that couples to an appliance worn on the opposing jaw, in accordance with embodiments.

FIG. 23 illustrates an orthodontic system 2300 with an integrally formed component (e.g., elastic 2302) that couples an upper appliance 2304 worn on the upper jaw and a lower appliance 2306 worn on the lower jaw, in accordance with embodiments. The elastic 2302 can be to be integrally formed as a single piece with the appliance 2304, 2306 using the direct fabrication techniques described herein. In the depicted embodiment, the elastic 2302 is coupled to the upper appliance 2304 at a first coupling point 2308 and is coupled to the lower appliance 2306 at a second coupling point 2310. The first coupling point 2308 can be positioned anteriorly relative to the second coupling point 2310 in order to advance the lower jaw anteriorly relative to the upper jaw, e.g., for treating class II malocclusions, sleep apnea, etc. In alternative embodiments, the first coupling point 2308 can be positioned posteriorly relative to the second coupling point 2310 in order to retract the lower jaw relative to the upper jaw, e.g., for treating class III malocclusions. The use of built-in elastics can be advantageous for improving convenience and patient compliance, by allowing the patient to insert the appliances directly without having to install, remove, and/or change out elastics.

Figure 24:
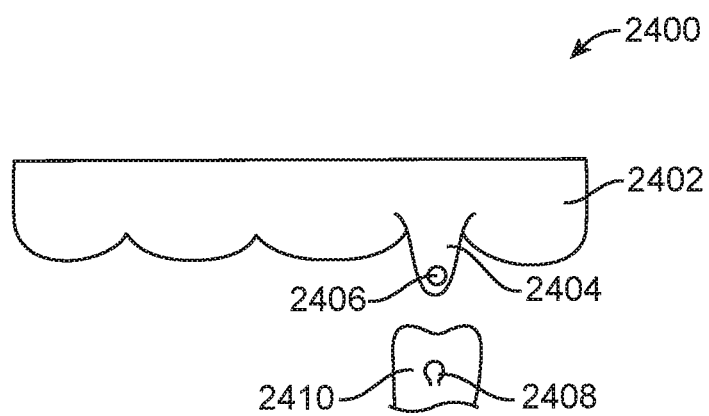
FIG. 24 illustrates an orthodontic appliance with an integrally formed component that couples to a device coupled to an intraoral structure, in accordance with embodiments.

FIG. 24 illustrates an orthodontic appliance 2400 with an integrally formed component that couples to a device coupled to an intraoral structure, in accordance with embodiments. The appliance 2400 includes a shell 2402 having cavities for receiving a patient's teeth and an integrally formed component, depicted herein as a protrusion 2404 having a hole 2406 shaped to receive and couple to a device 2408 (e.g., an attachment device, anchoring device such as a TAD, screw, etc.) coupled to an intraoral structure 2410 (e.g., a tooth). The protrusion 2404 can be rigid or elastic and may be used to extrude teeth or control over and/or under bite, for example. In alternatively embodiments, the integrally formed component can include other types of structures to mount onto the device 2408. For example, the integrally formed component can be a protrusion, a paddle, a flap, a tab, or the like that is directly or indirectly connected to the device 2408. Different types of integrally formed components can be used to allow for different ways of coupling to teeth, for example, to intrude teeth rather than to extrude teeth. Likewise, the device 2408 is depicted herein as an attachment device mounted to a tooth on the opposing jaw, but other types of devices and configurations can also be used. For example, the device 2408 can be integrally formed with a second orthodontic appliance or a portion of the appliance shell 2402, or can be attached to a different intraoral structure, such as the patient's jawbone or palate, for example.

In some embodiments, an orthodontic appliance includes an integrally formed component shaped to provide one or more mounting features for coupling an auxiliary component to the appliance. For example, the integrally formed component includes a mounting feature for coupling the appliance to an expander, archwires, or other like devices or elements of devices often useful for expanding the width of a patient's arch during the course of treatment for a condition, such as sleep apnea The auxiliary component can be any structure or device configured to be used in combination with an appliance in order to perform a function, such as one or more of force application and/or modification, structural reinforcement, actuation, sensing, providing power, and so on. The auxiliary component can be any device useful for orthodontic or dental treatment of a patient, such as elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, batteries, or sensors.

A mounting feature can be any structure or component that engages an auxiliary component or a portion thereof in order to couple the device to the orthodontic appliance. The mounting feature can be shaped so as to couple to, connect to, receive, engage and/or partially or wholly encapsulate the auxiliary component. For example, a mounting feature can include a hole, aperture, slit, groove, hook, button, ridge, flap, channel, etc. shaped to engage a portion of the auxiliary component so as to couple the appliance thereto. As another example, a mounting feature can include a cavity, chamber, receptacle, recess, opening, window, etc. shaped to receive a portion of the auxiliary component so as to partially or wholly encapsulate the auxiliary component within the appliance. The location of the mounting feature can correspond to the desired location of the auxiliary component relative to the appliance shell. An auxiliary component can be positioned at any location on the appliance shell, such as a lingual surface, occlusal surface, buccal surface, gingival portion, interior surface (e.g., near the received teeth), exterior surface (e.g., away from the received teeth), anterior portion, posterior portion, distal portion, mesial portion or the like, or combinations thereof. The location of the auxiliary component can be determined based on the function of the auxiliary component. For instance, a sensor configured to measure bite force can be located on an occlusal surface. A sensor configured to measure pressure, humidity, and/or temperature can be located on a buccal surface (e.g., near the posterior teeth for improved aesthetics) or on a lingual surface.

As discussed above and herein, the direct fabrication methods of the present disclosure allow for improved production of appliances with integrally formed mounting features for coupling to an auxiliary component. Using direct fabrication, mounting features can be integrally formed at any location on the appliance to accommodate coupling of an auxiliary component. In some embodiments, the auxiliary component can be formed and/or coupled to the appliance concurrently with formation of the appliance, e.g., using the same fabrication machine and/or process. For example, an auxiliary component can be automatically positioned and mounted to the mounting feature (e.g., using robotic mechanisms and the like) while the appliance is being formed using the direct fabrication methods herein, similar to insert molding techniques. Alternatively, the auxiliary component can be positioned and mounted to the mounting feature after the appliance has been formed.

In some embodiments, an integrally formed component includes a mounting feature configured to engage with (e.g., couple to) a connecting element, such as an elastic. Use of dental elastics can change the forces applied across a patient's tooth and/or teeth. The mounting feature can hold the elastic in place relative to the appliance when the elastic is properly inserted and positioned. The mounting feature may be a protrusion from or a recession of the appliance to engage with an elastic. Such protrusions or recessions may be but are not limited to hooks, buttons, knobs, pegs, flaps, protrusions, channels, grooves, ridges, slits, or divots.

For example, an appliance may have an integrally formed mounting feature in the wall of the appliance shell in the form of a hook for mounting elastics such as flexible bands, ligatures, or adjunct devices. Such a hook may resemble hooks found in dental care, or it may be specially designed for use with shell appliances. In some embodiments, an elastic can be coupled with the appliance via a hook formed by creating a u-shaped aperture located in the side of the appliance. The aperture can be formed into an existing appliance at a location selected for the transfer of the force from the elastic into the appliance. The aperture can have a slot width and a shape selected to accommodate the elastic.

A hook can also be positioned along a gingival margin of the appliance. For example, the tip of the hook may curve or angle away from soft tissue or back toward the tooth surface. The tip of the hook may also be curved, angled, or bent towards the gingival line such that the elastic may be placed into the appliance first before the appliance is worn, and the hook angle/curvature keeps the elastic from falling off of the appliance. An integrally formed hook may have any suitable shape for receiving an elastic, including any of those discussed in U.S. patent application Ser. No. 12/722,130, entitled "REINFORCED ALIGNER HOOKS," which is commonly assigned and incorporated by reference herein in its entirety for all purposes.

In some embodiments, the appliance can have more than one integrally formed mounting feature, such as a cutout and a hook. For example, the cutout and the hook may be provided for different teeth on different jaws so that coupling of an elastic may operate to apply tooth/jaw repositioning forces sufficient to treat tooth malocclusions such as distocclusion or mesiocclusion. A cutout may be provided for disposal over a posterior tooth in one jaw, while a hook may be provided for disposal over an anterior tooth in another jaw, for instance.

Figure 25:
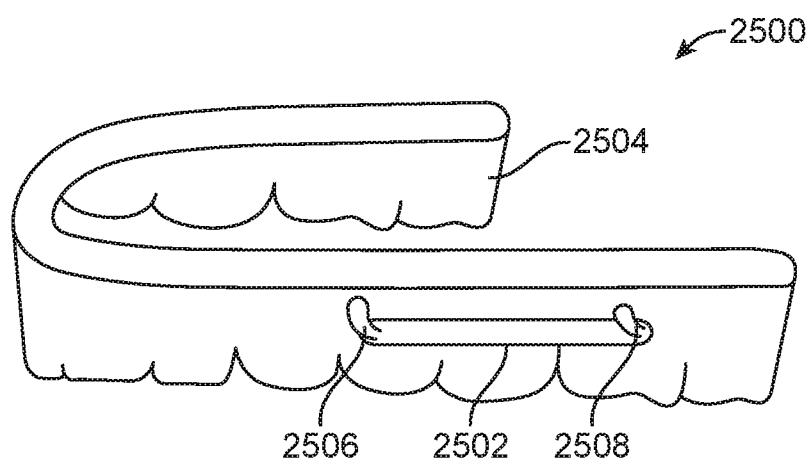
FIG. 25 illustrates an orthodontic appliance with integrally formed mounting features for coupling an elastic, in accordance with embodiments.

FIG. 25 illustrates an orthodontic appliance 2500 with integrally formed mounting features for coupling an elastic 2502, in accordance with embodiments. The appliance 2500 comprises a shell 2504 with a first (e.g., anterior) integrally formed mounting feature, such as a hook 2506, and a second (e.g., posterior) integrally formed mounting feature, such as a hook 2508, can be configured to be coupled to a dental elastic 2502. The elastic 2502 can exert a tensile force against different portions of the appliance 2500 (e.g., anterior and posterior portions) that are transmitted to the underlying teeth. It shall be appreciated that the placement and geometries of the integrally formed mounting features shown in FIG. 25 are exemplary and not intended to limit the plurality of placements and geometries possible in accordance with the aspects and embodiments described herein. Accordingly, the integrally formed mounted features can be integrally formed within the shell 2504 of the appliance 2500 at a different location or at the same location as the preceding appliance or as the subsequent appliance. The integrally formed mounting feature may be at any location of any appliance in accordance with the patient's treatment plan.

Figure 26:
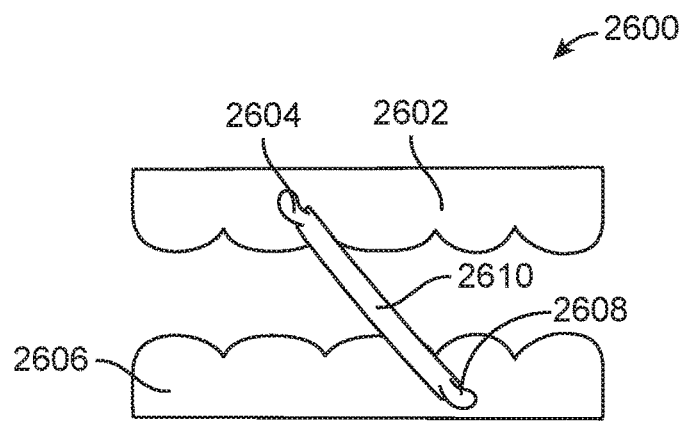
FIG. 26 illustrates an orthodontic system including an upper appliance with an integrally formed upper mounting feature and a lower appliance with an integrally formed lower mounting feature for coupling an elastic, in accordance with embodiments.

FIG. 26 illustrates an orthodontic system 2600 including an upper appliance 2602 with an integrally formed upper mounting feature 2604 and a lower appliance 2606 with an integrally formed lower mounting feature 2608 for coupling an elastic 2610, in accordance with embodiments. In the depicted embodiment, the upper mounting feature 2604 is a first hook integrally formed into the upper appliance 2602 worn on the upper jaw and the lower mounting feature 2608 is a second hook integrally formed into a lower appliance 2606 on the lower jaw. A dental elastic 2610 can be positioned over each hook to connect the upper appliance 2602 and lower appliance 2606, for example, to apply force to change the anterior-posterior alignment of the top jaw relative to the bottom jaw of the patient. The location and geometries of the upper and lower mounting features depicted herein are exemplary and not limiting. Rather, the upper and lower mounting feature can have any geometry and/or location as described herein.

Optionally, the appliance can be further modified to accommodate a portion of a coupled elastic or other connecting element coupled to an integrally formed mounting feature. For example, the appliance can include a cutout or recess shaped to avoid physical and/or functional interference with an elastic. The cutout can have any shape appropriate for preventing interference for use with a plurality of patient treatment plans including, for example, for treatment of distocclusion or mesiocclusion, or facilitating extrusion, intrusion, rotation, tipping and/or torquing. Accordingly, in some embodiments, coupling an elastic to a portion of the shell comprising a cutout or recess may operate to apply tooth and/or jaw repositioning forces sufficient to intrude or extrude a tooth. For example, a cutout may be provided for disposal over a tooth, while two hooks may be provided for disposal over both lateral sides of the same tooth. Accordingly, an elastic may operate to apply tooth/jaw repositioning forces that tend to move one or more teeth or the jaw in a vertical direction to intrude or extrude a tooth, for example.

Figure 27:
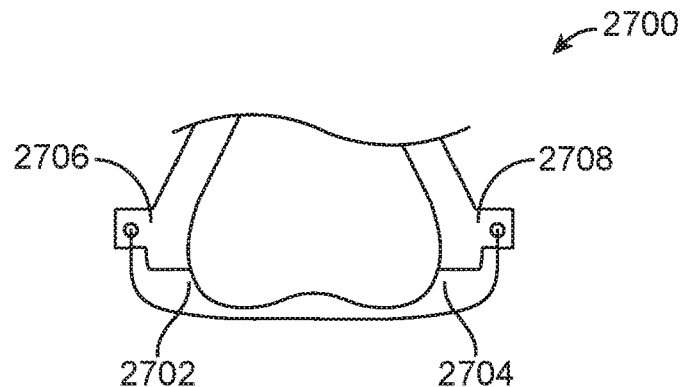
FIG. 27 illustrates an orthodontic appliance including a cutout accommodating a coupled elastic, in accordance with embodiments.

FIG. 27 illustrates an orthodontic appliance 2700 including a cutout 2702 for accommodating a coupled elastic 2704, in accordance with embodiments. The appliance 2700 includes a shell with a cutout 2702 over the occlusal surface of a received tooth, such that the occlusal surface of the tooth is exposed. The shell includes a first integrally formed mounting feature (e.g., a protrusion 2706) and a second integrally mounting feature (e.g., a protrusion 2708). Each of the protrusions 2706, 2708 can comprise a hole configured to receive and couple an elastic 2704. The mounting features can be located on opposite sides of the appliance 2700 (e.g., buccal and lingual surfaces), such that the coupled elastic 2704 is configured to push down on the occlusal surface of the tooth to intrude the tooth. Alternatively, the elastic 2704 can pull up on the occlusal surface (e.g., via attachment mounted on the tooth) to extrude the tooth (not shown).

Figure 28:
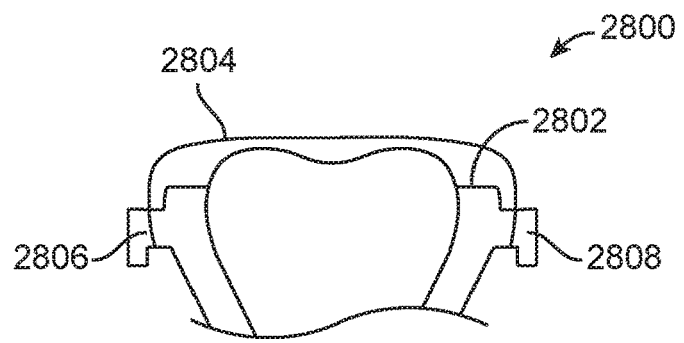
FIG. 28 illustrates an orthodontic appliance including a cutout for accommodating a coupled elastic, in accordance with embodiments.

FIG. 28 illustrates an orthodontic appliance 2800 including a cutout 2802 for accommodating a coupled elastic 2804, in accordance with embodiments. Similar to the appliance 2700, the appliance 2800 includes a shell with a cutout 2802 over the occlusal surface of a received tooth, such that the occlusal surface of the tooth is exposed. The shell includes a first integrally formed mounting feature a hook 2806) and a second integrally mounting feature (e.g., a hook 2808). Each of the hooks 2806, 2808 can be shaped to receive and couple an elastic 2804. The mounting features can be located on opposite sides of the appliance 2800 (e.g., buccal and lingual surfaces), such that the coupled elastic 2804 is configured to push down on the occlusal surface of the tooth to intrude the tooth. Alternatively, the elastic 2804 can pull up on the occlusal surface (e.g., via attachment mounted on the tooth) to extrude the tooth (not shown).

The illustrations in FIGS. 27 and 28 are not intended to be limiting, as integrally formed mounting features may have different geometries, locations and/or can be configured to treat a single tooth or a plurality of teeth. Additionally, an elastic can be coupled to a tooth, a different portion of the same appliance, or a different portion of a different device, as prescribed by the patient's treatment plan.

Figure 29:
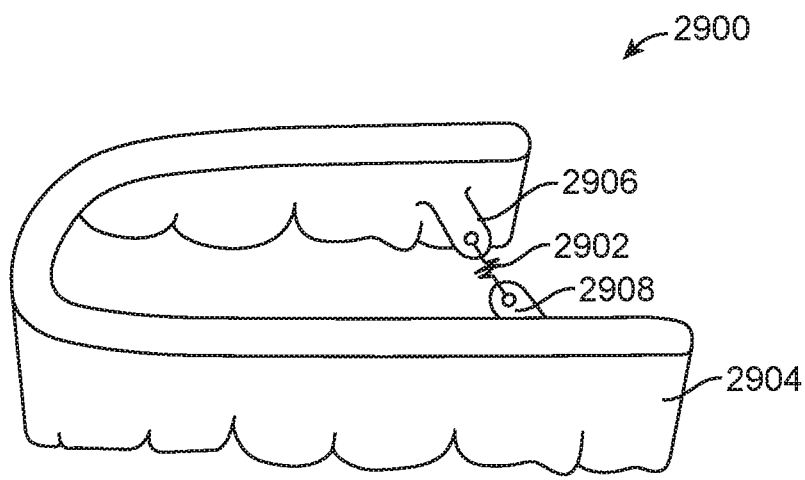
FIG. 29 illustrates an orthodontic appliance including integrally formed mounting features for coupling a spring, in accordance with embodiments.

FIG. 29 illustrates an orthodontic appliance 2900 including integrally formed mounting features for coupling a spring 2902, in accordance with embodiments. The appliance 2900 includes a shell 2904 comprising two integrally formed mounting features. A first mounting feature 2906 is positioned on a first distal portion of the shell 2904 and is shaped to couple a first portion of the spring 2902 (or a wire, or the like). A second mounting feature 2908 is positioned on a second distal portion opposite the first distal portion and is shaped to couple a second portion of the spring 2902 (or a wire, or the like). The first and second mounting features 2906, 2908 can be used to couple to a spring 2902 for use in spreading a patient's arch and/or palate, for example, as a stage of a patient's treatment plan to treat sleep apnea. Accordingly, the features may be configured to engage a plurality of different types of springs to allow arch and/or palate expansion forces to be adjusted during treatment. For example, different springs of different tensions can be used during the various stages during the course of treatment.

Figure 30:
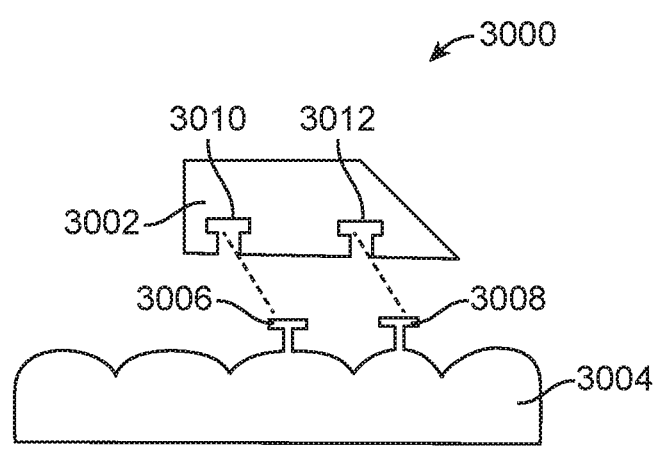
FIG. 30 illustrates an orthodontic appliance including integrally formed mounting features for coupling an advancement structure, in accordance with embodiments.

FIG. 30 illustrates an orthodontic appliance 3000 including integrally formed mounting features for coupling an advancement structure 3002, in accordance with embodiments. The appliance 3000 includes a shell 3004 with a plurality of integrally formed mounting features (e.g., protrusions 3006, 3008) shaped to mate with a corresponding mounting interface (e.g., holes 3010, 3012) in the advancement structure 3002. In alternative combinations, the mounting features can be located on the advancement structure 3002 and the mounting interface can be integrally formed with the shell 3004. The mounting features of the shell 3004 can be a pin, a peg or the like, and is typically a protrusion. In some embodiments, the plurality of holes in the advancement structure 3002 is greater than the number of corresponding protrusions of the shell 3004, such that the advancement structure 3002 can be positioned and re-positioned on the same appliance in accordance with the patient's treatment plan during the course of treatment in a plurality of different locations. Additionally, a plurality of advancement structures with different geometries can be used with the same shell by replacing an existing advancement structure with a different advancement structure. The illustrations are not intended to be limited as integrally formed features may have different geometries, locations and/or can be configured in accordance with a patient's treatment plan. A full description of an exemplary orthodontic appliance with advancement structures is described in U.S. application Ser. No. 14/992,325, the disclosure of which is incorporated herein by reference in its entirety.

Optionally, the appliance can include a reinforcement structure in the vicinity of the integrally formed mounting feature to reduce deflection induced by the device (e.g., elastic, spring, etc.) coupled to the integrally formed mounting feature. For example, the appliance can include a strengthened portion (e.g., via increased thickness in the area of the mounting feature). The appliance can also be locally stiffened by embedding a reinforcing structure (e.g., a stronger and stiffer material such as stainless steel or plastic resin filler) into the appliance to reinforce the appliance and/or mounting feature against deflection induced by the force from the coupled device.

The orthodontic appliances of the present disclosure can comprise any of the materials as disclosed herein or known to one of ordinary skill in the art. In some embodiments, an integrally formed component may be formed from the same material as the shell of the orthodontic appliance, or a different material from the shell of the orthodontic appliance. Materials for the shell and for the integrally formed component may be chosen during design of the patient's treatment plan to facilitate achieving a goal of the patient's treatment plan. For example, the shell may comprise a material that has a greater stiffness and/or tensile strength compared to an integrally formed component such as a corrugated feature. Alternatively, the shell may comprise a material that has a reduced stiffness and/or tensile strength compared to an integrally formed component such as a hook.

Orthodontic Appliances with Power Arms

In some embodiments, the orthodontic appliances herein include one or more power arms. As used herein, "power arm" may refer to an elongate structure having a first portion directly or indirectly coupled to a tooth or teeth, and a second portion extending along a gingival direction, such that force(s) and/or moment(s) applied to the second portion (e.g., via a coupled elastic) are transmitted to the coupled tooth or teeth. In some embodiments, an orthodontic appliance includes a pair of power arms connected to each other by a connecting structure (e.g., an elastic, spring, or the like). The connecting structure, which may also be referred to herein as a "spring structure" or an "elastic spring connector," can apply forces and/or torques to the power arms that are transmitted to the coupled teeth.

The power arms as disclosed herein can be directly fabricated and coupled to the teeth in many ways. For example, power arms can be directly fabricated with an appliance during the direct fabrication process, such that the resultant appliance includes integrally formed power arms. The power arms can be configured to couple to the teeth with the appliance placed on the teeth. The power arms directly fabricated with the appliance have the advantage of altering (e.g., increasing or decreasing) the force applied to the teeth at an intended location, relative to an appliance without power arms. The power arms can have a custom shape determined based on a three-dimensional scan data of the teeth and associated structures, such as the gums and clearance with the cheek. The directly fabricated appliance with power arms may comprise a similar modulus material for the power arms and the appliance. The stiffness of the appliance at various locations could be determined based on the thickness of the material. For example, where a locally stiffer structure is helpful, a thicker structure can be provided to add rigidity. As another example, the second moment of area of an appliance structure can be modified in order to increase the stiffness of the structure. Alternatively or in combination, the appliance may comprise different material properties, such as a more rigid material. The rigidity of the material can be varied by varying an amount of cross linking. The appliance and power arms may comprise different materials, such as different prepolymer and polymer materials.

The appliance with power arms can be one of a plurality of appliances with power arms to be placed on teeth in series in accordance with an orthodontic treatment plan. The structure of the power arms and the appliance can vary in accordance with the treatment plan to provide desired forces to the teeth.

In one aspect, an appliance for placement on teeth of a patient is provided. The appliance can comprise: a plurality of power arms; a connecting structure coupled to the plurality of power arms to apply a first force to the plurality of power arms; and a counter-force connector coupled to the plurality of power arms to apply a second force to the plurality of power arms opposing the first force.

In some embodiments, the connecting structure comprises a rest length and the counter-force connector comprises a length different than the rest length of the connecting structure. The length of the counter-force connector can be shorter than the rest length of the connecting structure such that the connecting structure is compressed when the counter-force connector is coupled to the plurality of power arms. The length of the counter-force connector can be longer than the rest length of the connecting structure such that the connecting structure is stretched when the counter-force connector is coupled to the plurality of power arms.

In some embodiments, the connecting structure is an elastic spring structure.

In some embodiments, the plurality of power arms each comprise an attachment shaped for bonding to a surface of a respective tooth.

In some embodiments, the appliance further comprises a shell comprising a plurality of tooth-receiving cavities, wherein the plurality of power arms is coupled to the shell. The plurality of power arms can be integrally formed with the shell by direct fabrication.

In some embodiments, the plurality of power arms is integrally formed with one or more of the connecting structure or the counter-force connector by direct fabrication.

In another aspect, a method for treating a patient's teeth is provided. The method can comprise: placing the appliance of any of the embodiments herein on the patient's teeth; and removing the counter-force connector from the appliance, such that the first force applied by the connecting structure to the plurality of power arms is transmitted to the patient's teeth.

In another aspect, a method of fabricating an orthodontic appliance is provided. The method can comprise: determining a movement path to move one or more teeth from an initial arrangement to a target arrangement; determining an appliance geometry for an orthodontic appliance configured to produce movement of the one or more teeth from the initial arrangement to the target arrangement, the orthodontic appliance comprising a plurality of power arms; and generating instructions for direct fabrication of the orthodontic appliance comprising the plurality of power arms.

In some embodiments, the orthodontic appliance further comprises a connecting structure coupled to the plurality of power arms to apply a first force to the plurality of power arms.

In some embodiments, the orthodontic appliance further comprises a counter-force connector coupled to the plurality of power arms to apply a second force to the plurality of power arms opposing the first force. The connecting structure can comprise a rest length and the counter-force connector can comprise a length different than the rest length of the connecting structure. The length of the counter-force connector can be shorter than the rest length of the connecting structure such that the connecting structure is compressed when the counter-force connector is coupled to the plurality of power arms. The length of the counter-force connector can be longer than the rest length of the connecting structure such that the connecting structure is stretched when the counter-force connector is coupled to the plurality of power arms.

In some embodiments, the instructions are configured to cause a fabrication machine to integrally form the plurality of power arms with the connecting structure and the counter-force connector.

In some embodiments, the plurality of power arms each comprise an attachment shaped for bonding to a surface of a respective tooth.

In some embodiments, the orthodontic appliance further comprises a shell comprising a plurality of tooth-receiving cavities, and the plurality of power arms is coupled to the shell. The instructions can be configured to cause a fabrication machine to integrally form the plurality of power arms with the shell.

In another aspect, an appliance for placement on teeth of a patient is provided. The appliance can comprise: a plurality of power arms; a connecting structure extending between the power arms to apply force to the power arms; and a counter-force connector extending between the power arms.

In some embodiments, the counter-force connector holds the power arms at a separation distance and/or angle to each other. The power arms can be configured to engage a pair of teeth to torque to the teeth with an amount of force from the connecting structure. The counter-force connector can be configured for removal to apply the torque to the teeth with the force from the connecting structure when the power arms have been coupled to the teeth.

In some embodiments, the appliance further comprises a tooth locating structure shaped to receive at least a portion of a tooth.

In some embodiments, the plurality of power arms each comprises an attachment.

In some embodiments, the connecting structure is a preloaded spring structure comprising a predetermined amount of force.

In some embodiments, the appliance has been directly fabricated.

In some embodiments, the power arms comprise a shape profile determined in response to three-dimensional scan data of the patient's oral cavity.

In another aspect, an appliance for placement on teeth of a patient is provided. The appliance can comprise: a polymeric shell comprising a plurality of teeth receiving cavities; and a plurality of power arms extending from the shell to engage the teeth with force transmitted through the shell.

In some embodiments, the polymeric shell and the plurality of power arms have been directly fabricated together.

In some embodiments, the appliance further comprises a connecting structure extending between the power arms to rotate one or more teeth. The connecting structure can have been directly fabricated with the polymeric shell and the power arms. The connecting structure can be configured to provide a predetermined amount of force to the power arms when placed on the teeth.

In some embodiments, the plurality of power arms comprises a shape profile determined in response to three-dimensional scan data of the patient's oral cavity.

In some embodiments, the polymeric shell and the plurality of power arms are part of a treatment plan comprising a plurality of appliances, the plurality of appliances each having a plurality of power arms to move teeth in accordance with a treatment plan.

In some embodiments, the appliance further comprises: a preloaded spring structure extending between the power arms; and a counter force connector extending between the power arms.

In another aspect, a method of fabricating an appliance is provided. The method can comprise: receiving scan profile data of a mouth of a patient; determining a shape profile of a plurality of power arms in response to the scan profile data of the mouth; and outputting direct fabrication instructions to manufacture the appliance with the plurality of power arms.

In some embodiments, the appliance and the plurality of power arms are directly fabricated.

In another aspect, a method comprising providing an appliance as in any one of the embodiments herein.

Figure 31:
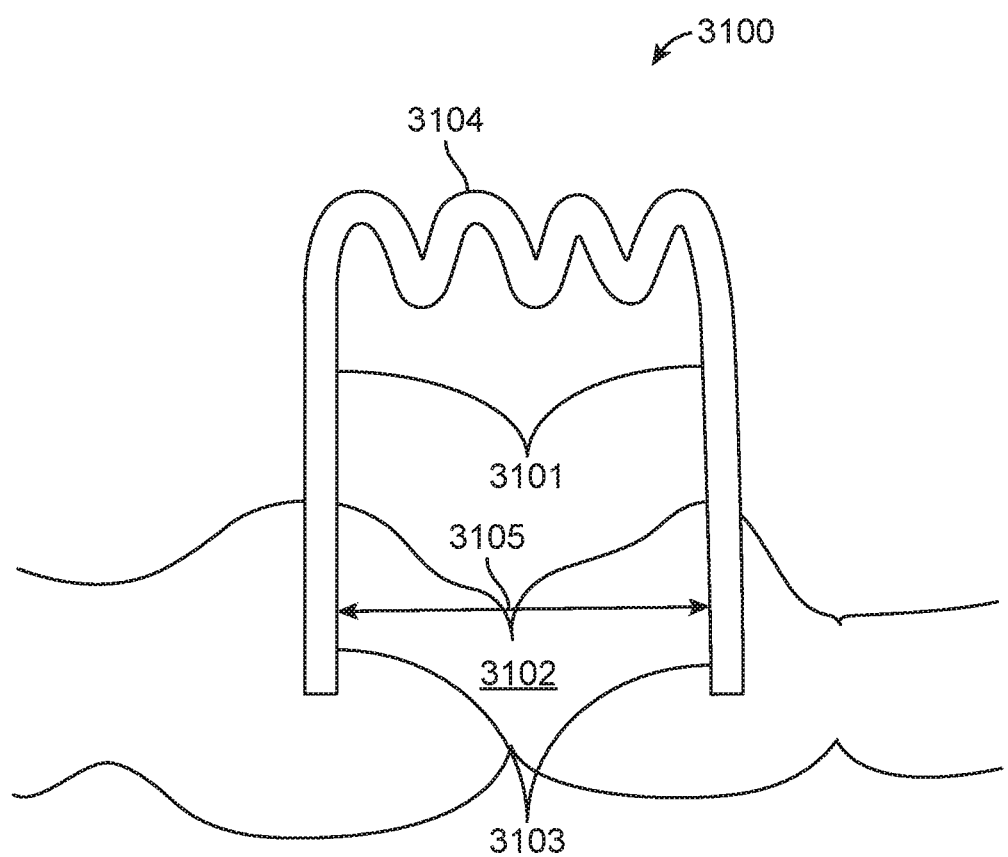
FIG. 31 illustrates an orthodontic appliance comprising a pair of directly fabricated power arms, in accordance with embodiments.

FIG. 31 illustrates an orthodontic appliance 3100 comprising a pair of directly fabricated power arms 3101, in accordance with embodiments. The power arms 3101 are coupled to an appliance shell 3102 at connection points 3103. The appliance shell 3102 comprises a plurality of tooth-receiving cavities, each of which may fit a patient's tooth in order to apply tooth-moving forces. In some embodiments, the connection points 3103 may comprise a direct material connection formed during fabrication of the appliance.

The power arms are connected via a connecting structure 3104 (e.g., an elastic, spring, or the like) which applies an elastic force on power arms 3101, which in turn allows power arms 3101 to apply a tooth-moving force on a patient's teeth. In particular, the power arms 3101 act as a lever, applying force and/or torque to connection points 3103, and thereby to the appliance shell 3102. The appliance shell, in turn, applies force on a patient's teeth through contact between the teeth and the tooth-receiving cavities of the shell. By choosing properties such as the length and connection points of power arms, it may be possible to apply force on teeth at or near their center of resistance, without inducing unwanted tipping. In order to act as an effective lever, power arms 3101 can be fabricated from a rigid material, which may differ from the material from which the shell 3102 or the connecting structure 3104 are fabricated, for example.

An orthodontic appliance with power arms can be fabricated in a variety of ways. In some embodiments, the power arms and connecting structure can be directly fabricated concurrently with the appliance shell, such that the power arms and connecting structure are both integrally formed with the shell. The power arms can be fabricated with or without the connecting structure. Although the connecting structure can be optional, such that the patient places elastic bands on the teeth, in some embodiments, the connecting structure 3104 is directly fabricated with the appliance and power arms with direct fabrication as described herein. The directly fabricated connecting structure has the advantage of applying force to the power arms without the patient placing an elastic band on the power arm. The connecting structure, appliance, and power arms can be directly fabricated in a free standing unloaded configuration such that when the aligner is placed on the teeth and deformed, the resulting strain and deformation to the connector spring structure results in force(s) and/or moment(s) applied from the connector to the power arms.

In alternative embodiments, the power arms can be directly fabricated concurrently with the appliance shell, while the connecting structure is fabricated separately. In such embodiments, the power arms are integrally formed with the shell, while the connecting structure is a separate component that is subsequently coupled to the power arms, e.g., before or while the appliance is worn by the patient. The connecting structure may or may not be produced by direct fabrication techniques.

In alternative embodiments, the power arms can be directly fabricated concurrently with the connecting structure, while the appliance shell is fabricated separately. In such embodiments, the power arms are integrally formed with the connecting structure, while the appliance shell is a separate component that is subsequently coupled to the power arms, e.g., before or while the appliance is worn by the patient. The appliance shell may or may not be produced by direct fabrication techniques.

In alternative embodiments, the appliance shell, power arms, and connecting structure can each be fabricated separately and subsequently assembled to produce an orthodontic appliance with power arms. The appliance shell, power arms, and/or connecting structure can be produced using direct fabrication techniques, or can be produced using other techniques (e.g., indirect fabrication), as desired.

Depending on the chosen design of the connecting structure 3104, an outward force or an inward force may be provided. The direction of the force may be determined by the rest length of the connecting structure 3104 relative to the distance 3105 between connection points, wherein a longer rest length causes an outward force and a shorter rest length shorter causes an inward force. The magnitude may be determined by both the spring constant of the connecting structure 3104 and the magnitude of difference between the rest length of the connecting structure 3104 and the distance 3105 between connection points, as may be approximated, for example, by Hooke's Law. In some embodiments, the connecting structure 3104 may be replaced with a separately-applied elastic material such as a band, and in some embodiments, a band may be combined with the connecting structure 3104 to provide increased elastic force. In some embodiments, an appliance may comprise a plurality of power arm pairs, each pair connected with an elastic spring structure.

In some embodiments, the connection points 3103 may comprise an adhesive connection between power arms 3101 and shell 3102, for example.

In some embodiments, the connection points may comprise an interlock mechanism whereby the power arms 3101 may be removably connected to shell 3102, for example.

In some embodiments, power arms may attach to caps comprising tooth-receiving cavities configured to receive teeth. In some embodiments, power arms may be bonded directly to teeth without need for attachments. In some embodiments, an orthodontic appliance may be configured to be placed onto teeth to which power arms are bonded, for example comprising spaces through which power arms may extend. In some embodiments, an orthodontic appliance may be configured to fit over caps comprising power arms.

In some embodiments, power arms may apply force to adjacent teeth, and in some embodiments, power arms may apply force to non-adjacent teeth.

Figure 32:
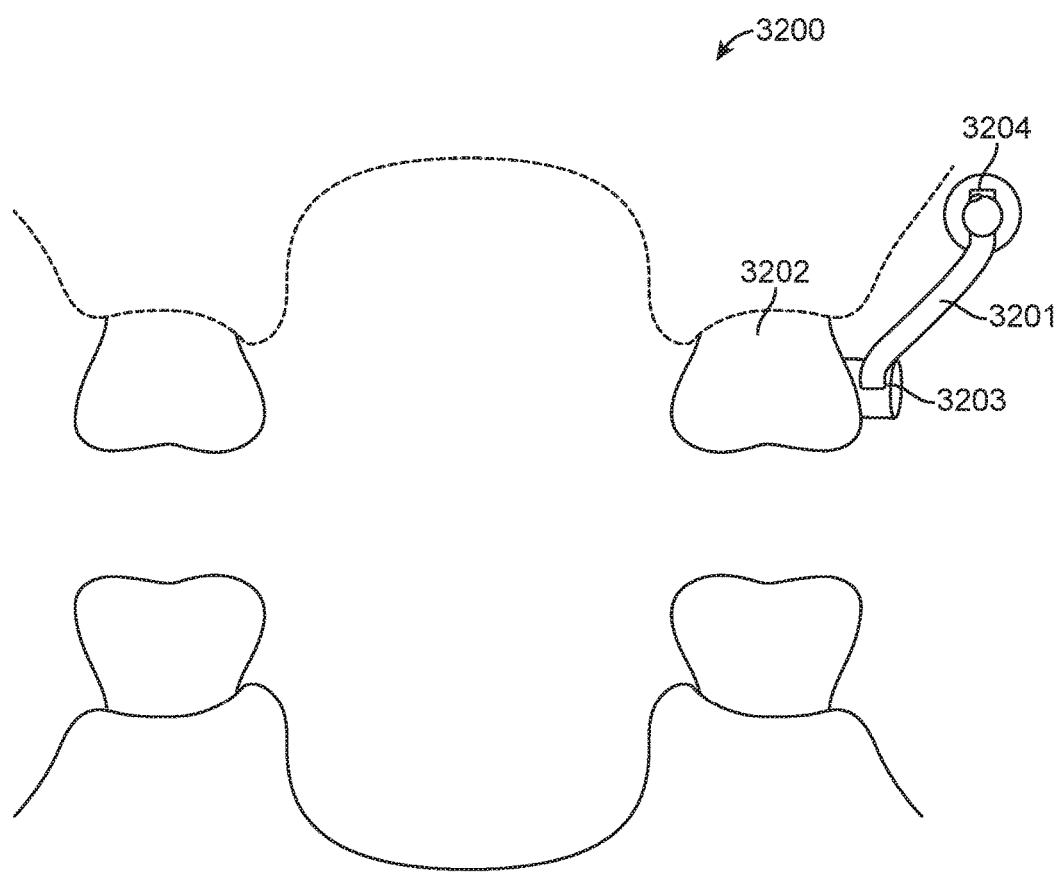
FIG. 32 illustrates a patient's mouth, in which a directly fabricated power arm is coupled to a tooth to apply a tooth-moving force, in accordance with embodiments.

FIG. 32 illustrates a patient's mouth, in which a directly fabricated power arm 3201 comprising attachment 3203 is coupled to a tooth 3202 to apply a tooth-moving force, in accordance with embodiments. The coupling is accomplished with attachment 3203 comprising power arm 3201 bonded to the tooth 3202. The bonding of the attachment to the tooth may comprise an adhesive connecting the attachment to the tooth. The power arm is coupled to another power arm as described herein by a connecting structure 3204, to provide a tooth-moving force on the tooth 3202 as described herein. The three-dimensional shape of the power arm can be determined in response to a scan of the patient's oral cavity as described herein. A similar directly fabricated attachment and power arm can be provided on another tooth and coupled to power arm 3201, attachment 3203 and connecting structure 3203 as described herein, and each of these components can be directly fabricated together to provide improved attachment with power arms on the teeth. The power arm 3201 may be bonded to the attachment 3203, the two may be directly fabricated as a single object, or the two may connect using an interlock mechanism.

Figure 33:
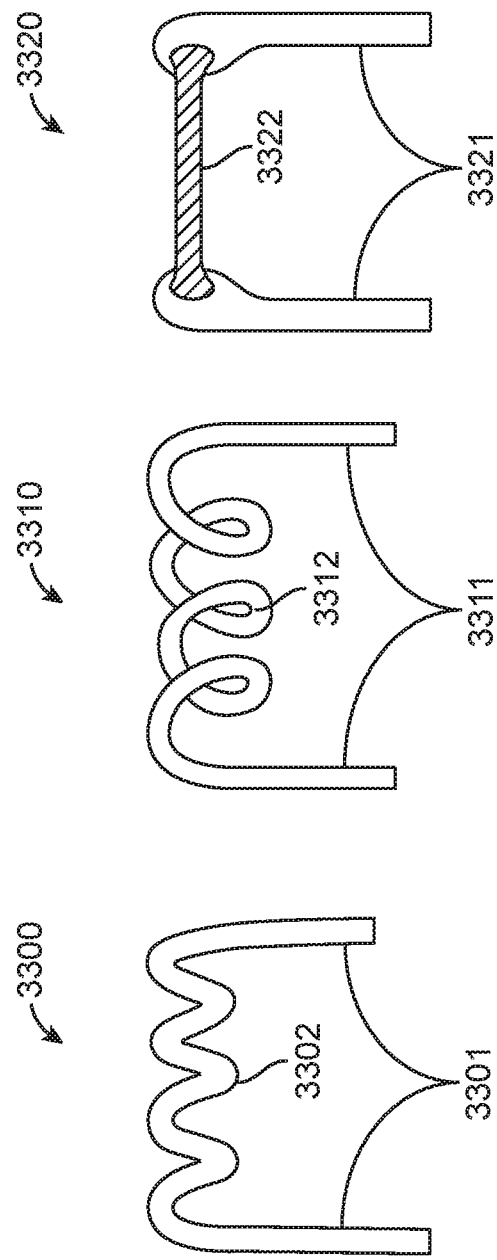
FIGS. 33A through 33C illustrates various spring structures that may be fabricated as part of a power arm structure, in accordance with embodiments.

FIGS. 33A through 33C illustrate various spring structures that may be directly fabricated as part of a power arm structure, in accordance with embodiments. The structures illustrated may be readily manufactured by the direct fabrication methods disclosed herein, and may be interchangeably used in any of the appliance and power arm structures disclosed herein. In power arm structure 3300, power arms 3301 are connected by an accordion-shaped elastic spring structure 3302, which provides an elastic force on power arms 3301, as determined by its spring constant and rest length. In power arm structure 3310, power arms 3311 are connected by a helical-coil elastic spring structure 3312, which provides an elastic force on power arms 3311, as determined by its spring constant and rest length. In power arm structure 3320, power arms 3321 are connected by a spring structure 3322 comprising an elastic material, which provides an elastic force on power arms 3321, as determined by its spring constant and rest length. The elastic material may be chosen on the basis of the spring constant desired, as determined by its elasticity. In some cases, the elastic material may comprise a relatively rigid material that expands when in contact with a patient's saliva; for example, a hydrophilic polymer. As the polymer swells, it pushes the power arms apart, allowing them to provide a tooth moving force. The use of such swelling materials may allow the fabrication of power arms that only apply force on their attachment points when actually worn by the patient. In some embodiments, the material may include shape memory material that has a first shape outside the mouth, for example, at room temperature, and has a shape inside the mouth, for example, at body temperature. Shape memory material may change shape based on temperature, for example, by contracting or expanding.

The directly fabricated attachments and power arms can be preloaded in a spaced apart configuration to provide a desired amount of torque to the patient's teeth. When placing preloaded power arms and an attachment into the mouth of a patient, it may be desirable to avoid applying force until the installation of the power arms is complete to facilitate handling and placement. For example, a preloading structure can be provided such that the person placing the directly fabricated power arms with the attachment does not have to urge the two attachments together to load the spring when the attachments are placed on the teeth, thereby facilitating placement.

Figure 34:
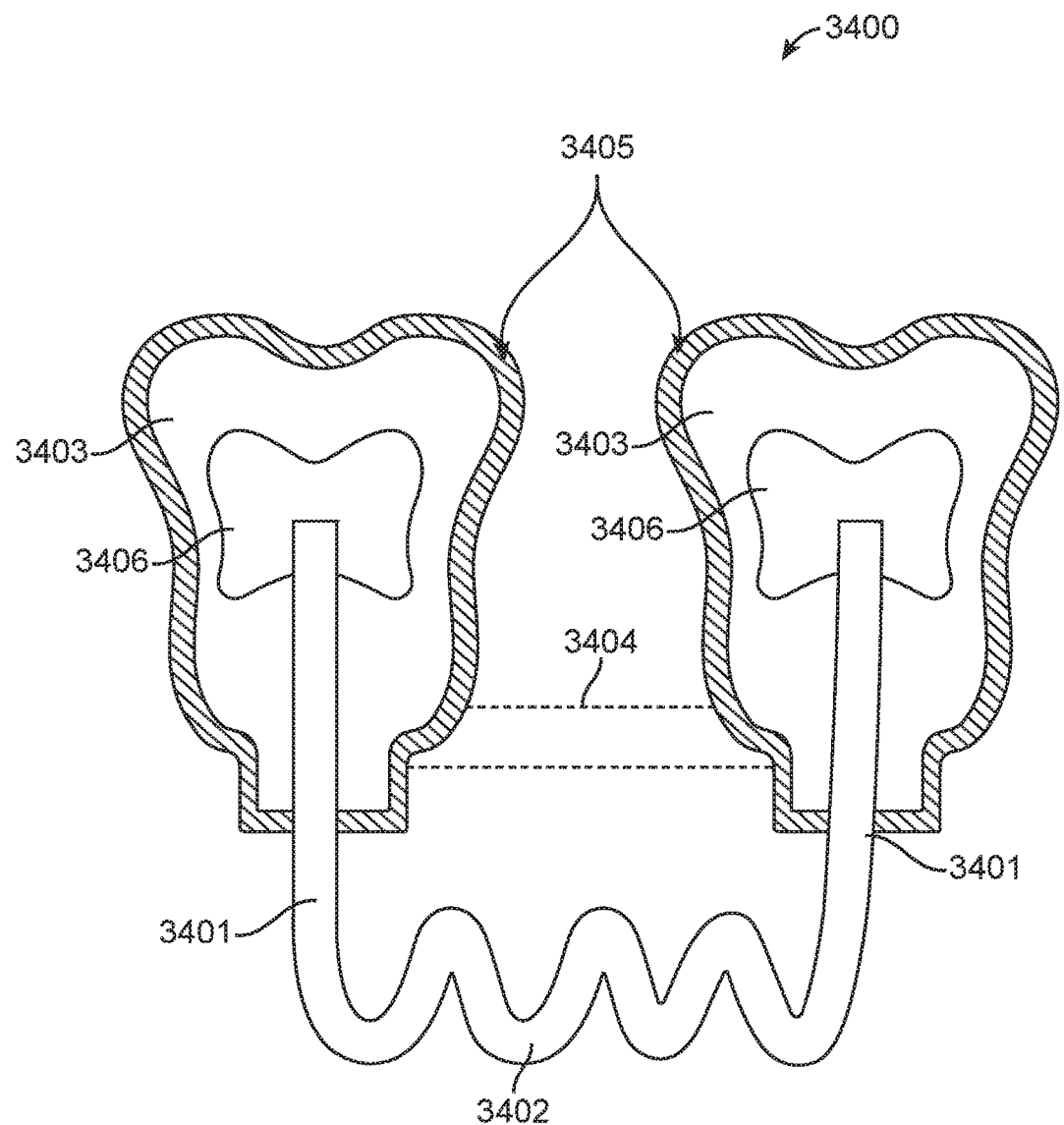
FIG. 34 illustrates a "pre-loading" mechanism whereby the power arm's tooth-moving force is balanced for easier placement on a patient's teeth, in accordance with embodiments.

FIG. 34 illustrates a pre-loaded assembly 3400 of directly fabricated components comprising power arms 3401 having attachments 3406, a preloaded spring structure 3402, optionally a counter-force connector 3404, and a locating structure 3403, in accordance with embodiments. The counter-force connector 3404 balances the power arm's tooth-moving force with an opposing force for easier placement on a patient's teeth. The locating structures 3403 are configured to receive structures of the patient's teeth in order to place the attachments at a predetermined location on the teeth. The locating structures 3403 may comprise a plurality of tooth receiving cavities, or engagement structures to couple to a portion of a received tooth such as an occlusal surface or an interproximal surface, for example.

As the power arms are placed with the locating structure 3403, they will typically place connecting structure 3402 under strain, which may make placement difficult. To compensate for this problem, a counter-force connecter 3404 may be included to balance out the force of connecting structure 3402. Counter-force connector 3404 may be connected to locating structure 3403, and may be fabricated as a part of power arms 3401. Counter-force connector 3404 may be fabricated from a rigid material, and configured to relieve the strain from connecting structure 3402 by pulling or pushing in the opposite direction as needed. In the case where counter-force connecter 3404 is fabricated as part of power arms 3401, counter-force connecter 3404 may be cut by the orthodontist after installation of power arms is finished, in order to allow connecting structure 3402 to apply an unimpeded force on the patient's teeth. In some cases, it may be desirable to smooth the surfaces of power arms 3401 after cutting counter-force connecter 3404, so as to avoid uncomfortable surfaces or sharp edges within the patient's mouth.

The pre-loading structure 3400 comprises a pair of power arms connected by a connecting structure 3402. The power arms are disposed within a locating structure 3403, which may comprise at least a portion an appliance worn by the patient, for example. The locating structure 3403 can be directly fabricated with the power arms and attachments, and can be sized and shaped for placement on the patient's teeth in order to position the attachments at desired locations 3405 on the teeth. The locating structure 3403 can be removed subsequent to placement and bonding of the attachments to the patient's teeth.

FIGS. 35A through 35C illustrate the operation of the counter-force connecter to pre-load a pair of power arms for installation, in accordance with embodiments. The power arms may be initially fabricated in a relaxed state 3500, comprising a plurality of power arms 3501, connected by a connecting structure 3502 that is uncompressed. A first power arm of the plurality of the power arms 3501 further comprises a counter-force connector 3504, connected to the first power arm. The counter-force connector 3504 comprises a mechanism, such as hook 3505, that lets it attach to a second power arm of the plurality of power arms. Because the length of the counter-force connector 3504 is shorter than the rest length of the connecting structure 3502, the connecting structure 3502 is compressed when counter-force connector 3504 is connected to the second power arm, as shown in pre-loaded state 3510. After then installing the power arms into a dental appliance or attaching them to the tooth, the counter-force connector may be removed, for example by cutting or breaking it at junction 3503 and/or unhooking hook 3505, allowing the power arms to apply outwardly-directed force(s) to the teeth of a patient (e.g., to increase a space between teeth), as illustrated in installed state 3520. In some cases, counter-force connector may comprise hooks or other attachment mechanisms at each end, so that it may be more easily removed after use.

FIGS. 36A through 36C illustrate the operation of the counter-force connecter to pre-load a pair of power arms for installation, in accordance with embodiments. The power arms may be initially fabricated in a relaxed state 3600, comprising a plurality of power arms 3601, connected by a connecting structure 3602 that is uncompressed. A first power arm of the plurality of the power arms 3601 further comprises a counter-force connector 3604, connected to the first power arm. The counter-force connector 3604 comprises a mechanism, such as hook 3605, that lets it attach to a second power arm of the plurality of power arms. Because the length of counter-force connector 3604 is longer than the rest length of the connecting structure 3602, the connecting structure 3602 is stretched when counter-force connector 3604 is connected to the second power arm, as shown in pre-loaded state 3610. After then installing the power arms into a dental appliance or attaching them to the tooth, the counter-force connector may be removed, for example by cutting or breaking it at junction 3603 and/or unhooking hook 3605, allowing the power arms to apply inward-directed force(s) to the teeth of a patient (e.g., for space closure), as illustrated in installed state 3620. In some cases, counter-force connector may comprise hooks or other attachment mechanisms at each end, so that it may be more easily removed after use.

Figure 37B:
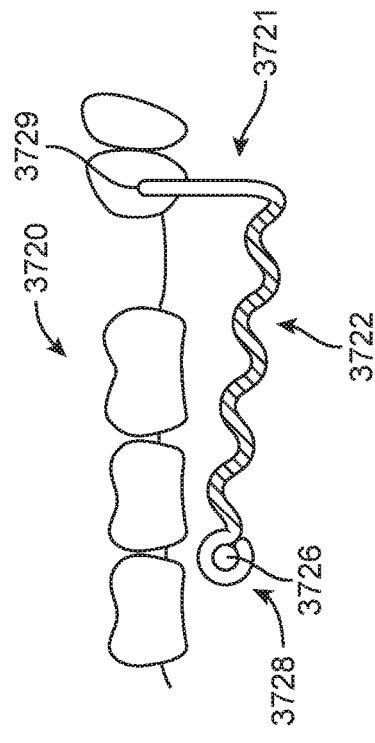
FIGS. 37A through 37D illustrate single power arm appliances, in accordance with embodiments.
Figure 37D:
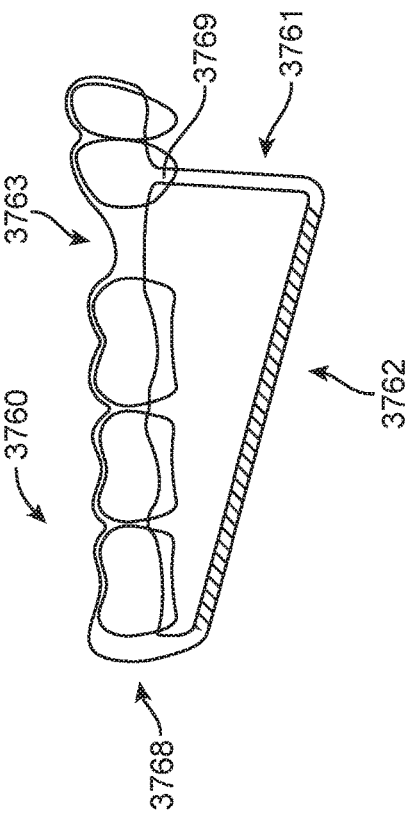
Figure 37A:
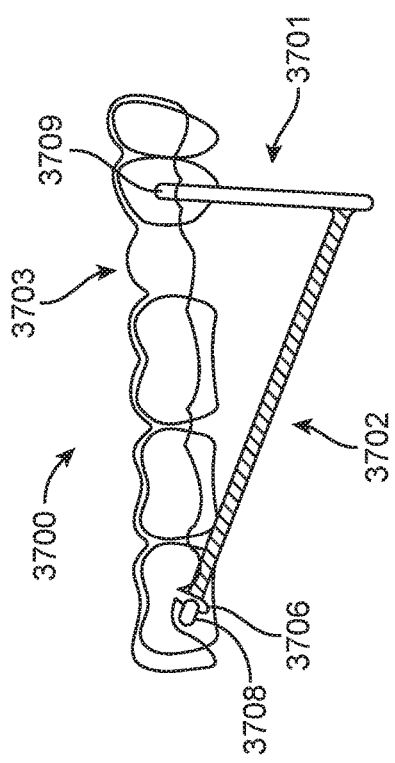

FIGS. 37A through 37D illustrate embodiments of single power arm appliances. In some embodiments, a single power arm can be used to move teeth. Force on the power arm can be reacted against an aligner, against a button mounted on a tooth, or against a TAD or other structure. FIG. 37A shows a single power arm appliance 3700 including a single power arm 3701 and an aligner 3703. A first end 3709 of the power arm 3701 is attached to the aligner 3703. In some embodiments, the first end 3709 is bonded directly to a tooth. A second end of the power arm 3701 is connected to a connecting structure 3702, which may also be an elastic element. The terminal end of the connecting structure 3702 includes a coupling 3708, such as a hook, that engages with a corresponding coupling 3706, such as a hook, loop, or other coupling, that is integrated with the aligner 3703. Force is transmitted between the power arm 3701 and the aligner hook 3706 via the connecting structure 3702 to move a patient's teeth.

FIG. 37B shows a single power arm appliance 3720 including a single power arm 3721. A first end 3729 of the power arm 3721 is attached directly to one of a patient's teeth while a second end of the power arm 3721 is connected to a connecting structure 3722. The terminal end of the connecting structure 3722 includes a coupling 3728, for example an eye hook, that engages with a corresponding coupling 3726, such as a TAD that is implanted in the patient. Force is transmitted between the power arm 3721 and the TAD via the connecting structure 3722 to move a patient's teeth.

Figure 37C:
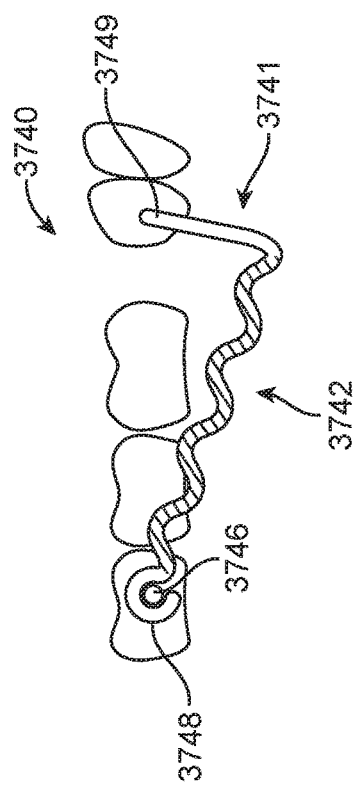

FIG. 37C shows a single power arm appliance 3740 including a single power arm 3741. A first end 3749 of the power arm 3741 is attached directly to one of a patient's teeth while a second end of the power arm 3741 is connected to a connecting structure 3742. The terminal end of the connecting structure 3742 includes a hook 3748 that engages with a corresponding button 3746 that is attached to one of the patient's teeth. Force is transmitted between the power arm 3741 and the button 3746 via the connecting structure 3742 to move a patient's teeth.

FIG. 37D shows a single power arm appliance 3760 including a single power arm 3761 and an aligner 3763. A first end 3769 of the power arm 3761 is attached to or integrated with the aligner 3763 at a first location on the aligner while a second end of the power arm 3761 is connected to a connecting structure 3762. The terminal end 3768 of the connecting structure 3762 is also attached to or integrated with the aligner 3703 at a second location on the aligner. Force is transmitted between the power arm 3761 and the second location on the aligner via the connecting structure 3762 to move a patient's teeth.

In some embodiments, a single power arm can have a first end bonded to a first tooth and a second end bonded, via a connecting structure, to a second tooth.

Direct Fabrication of Orthodontic Appliances

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

In some embodiments, the direct fabrication methods provided herein build up the object geometry in a layer-by-layer fashion, with successive layers being formed in discrete build steps. Alternatively or in combination, direct fabrication methods that allow for continuous build-up of an object geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials, including but not limited to one or more of the following: polymer matrix reinforced with ceramic or metallic polymers, a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step using the same fabrication machine and method. For instance, a multi-tip extrusion apparatus can be used to selectively dispense multiple types of materials (e.g., resins, liquids, solids, or combinations thereof) from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed. The relative arrangement of the first and second portions can be varied as desired, e.g., the first portion can be partially or wholly encapsulated by the second portion of the object. The sequential manufacturing steps can be performed using the same fabrication machine or different fabrication machines, and can be performed using the same fabrication method or different fabrication methods. For example, a sequential multi-manufacturing procedure can involve forming a first portion of the object using stereolithography and a second portion of the object using fused deposition modeling.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 μm, or within a range from about 5 μm to about 50 μm, or within a range from about 20 μm to about 50 μm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

Although various embodiments herein are described with respect to direct fabrication techniques, it shall be appreciated that other techniques can also be used, such as indirect fabrication techniques. In some embodiments, the appliances herein (or portions thereof) can be produced using indirect fabrication techniques, such as by thermoforming over a positive or negative mold. Indirect fabrication of an orthodontic appliance can involve one or more of the following steps: producing a positive or negative mold of the patient's dentition in a target arrangement (e.g., by additive manufacturing, milling, etc.), thermoforming one or more sheets of material over the mold in order to generate an appliance shell, forming one or more structures in the shell (e.g., by cutting, etching, etc.), and/or coupling one or more components to the shell (e.g., by extrusion, additive manufacturing, spraying, thermoforming, adhesives, bonding, fasteners, etc.). Optionally, one or more auxiliary appliance components as described herein (e.g., elastics, wires, springs, bars, arch expanders, palatal expanders, twin blocks, occlusal blocks, bite ramps, mandibular advancement splints, bite plates, pontics, hooks, brackets, headgear tubes, bumper tubes, palatal bars, frameworks, pin-and-tube apparatuses, buccal shields, buccinator bows, wire shields, lingual flanges and pads, lip pads or bumpers, protrusions, divots, etc.) are formed separately from and coupled to the appliance shell (e.g., via adhesives, bonding, fasteners, mounting features, etc.) after the shell has been fabricated.

In some embodiments, the orthodontic appliances herein can be fabricated using a combination of direct and indirect fabrication techniques, such that different portions of an appliance can be fabricated using different fabrication techniques and assembled in order to form the final appliance. For example, an appliance shell can be formed by indirect fabrication (e.g., thermoforming), and one or more structures or components as described herein (e.g., auxiliary components, power arms, etc.) can be added to the shell by direct fabrication (e.g., printing onto the shell).

Digital Design of Orthodontic Appliances

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled additive manufacturing such as 3D printing, etc.). The computer-based methods presented herein can improve the accuracy, flexibility, and convenience of appliance fabrication.

In some embodiments, computer-based 3-dimensional planning/design tools, such as Treat™ software from Align Technology. Inc., may be used to design and fabricate the orthodontic appliances described herein.

Figure 38:
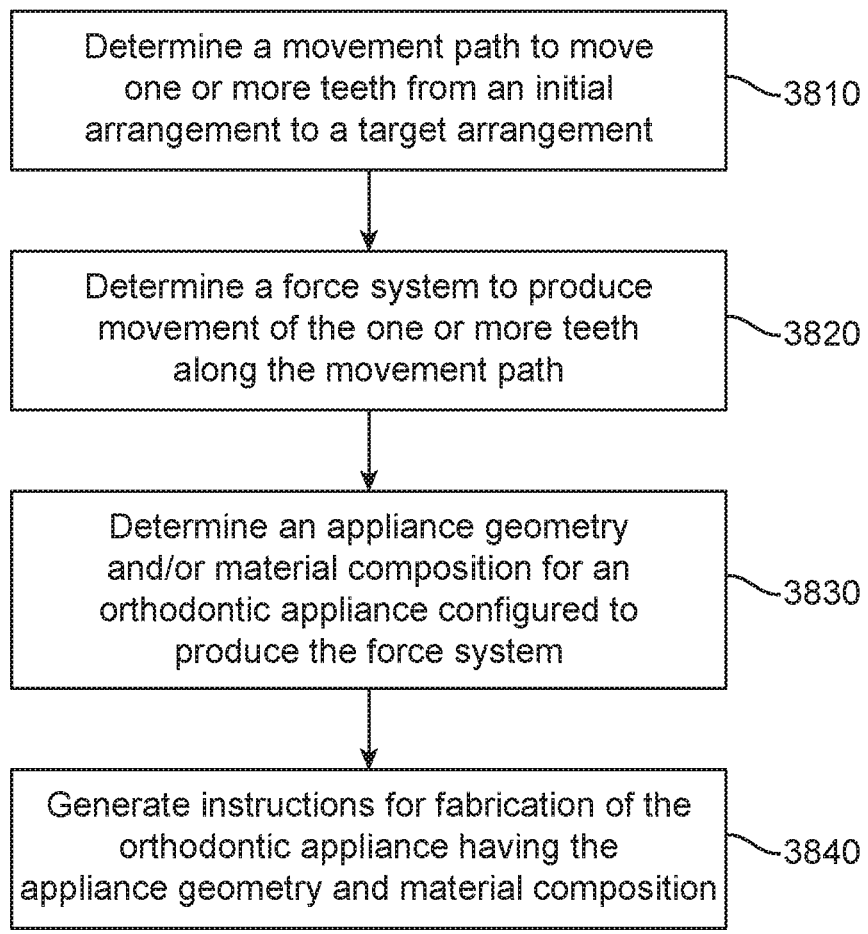
FIG. 38 illustrates a method for designing an orthodontic appliance, in accordance with embodiments.

FIG. 38 illustrates a method 3800 for designing an orthodontic appliance to be produced by direct fabrication, in accordance with embodiments. The method 3800 can be applied to any embodiment of the orthodontic appliances described herein. Some or all of the steps of the method 3800 can be performed by any suitable data processing system or device, e.g., one or more processors configured with suitable instructions.

In step 3810, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In step 3820, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

Determination of the force system can be performed in a variety of ways. For example, in some embodiments, the force system is determined on a patient-by-patient basis, e.g., using patient-specific data. Alternatively or in combination, the force system can be determined based on a generalized model of tooth movement (e.g., based on experimentation, modeling, clinical data, etc.), such that patient-specific data is not necessarily used. In some embodiments, determination of a force system involves calculating specific force values to be applied to one or more teeth to produce a particular movement. Alternatively, determination of a force system can be performed at a high level without calculating specific force values for the teeth. For instance, step 3820 can involve determining a particular type of force to be applied (e.g., extrusive force, intrusive force, translational force, rotational force, tipping force, torquing force, etc.) without calculating the specific magnitude and/or direction of the force.

In step 3830, an appliance geometry and/or material composition for an orthodontic appliance configured to produce the force system is determined. The appliance can be any embodiment of the appliances discussed herein, such as an appliance having variable localized properties, integrally formed components, and/or power arms.

For example, in some embodiments, the appliance comprises a heterogeneous thickness, a heterogeneous stiffness, or a heterogeneous material composition. In some embodiments, the appliance comprises two or more of a heterogeneous thickness, a heterogeneous stiffness, or a heterogeneous material composition. In some embodiments, the appliance comprises a heterogeneous thickness, a heterogeneous stiffness, and a heterogeneous material composition. The heterogeneous thickness, stiffness, and/or material composition can be configured to produce the force system for moving the teeth, e.g., by preferentially applying forces at certain locations on the teeth. For example, an appliance with heterogeneous thickness can include thicker portions that apply more force on the teeth than thinner portions. As another example, an appliance with heterogeneous stiffness can include stiffer portions that apply more force on the teeth than more elastic portions. Variations in stiffness can be achieved by varying the appliance thickness, material composition, and/or degree of photopolymerization, as described herein.

In some embodiments, determining the appliance geometry and/or material composition comprises determining the geometry and/or material composition of one or more integrally formed components to be directly fabricated with an appliance shell. The integrally formed component can be any of the embodiments described herein. The geometry and/or material composition of the integrally formed component(s) can be selected to facilitate application of the force system onto the patient's teeth. The material composition of the integrally formed component can be the same as or different from the material composition of the shell.

In some embodiments, determining the appliance geometry and/or material composition comprises determining the geometry and/or material composition for a power arm design for the orthodontic appliance. The power arm design can utilize any of the power arm embodiments described herein. The power arm design can be configured to produce the force system is determined. Determination of the power arm design, appliance geometry, material composition, and/or properties can be performed using a treatment or force application simulation environment.

The step 3830 can involve analyzing the desired force system in order to determine an appliance geometry and material composition that would produce the force system. In some embodiments, the analysis involves determining appliance properties (e.g., stiffness) at one or more locations that would produce a desired force at the one or more locations. The analysis can then involve determining an appliance geometry and material composition at the one or more locations to achieve the specified properties. Determination of the appliance geometry and material composition can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including finite element analysis packages from ANSYS, Inc., of Canonsburg, Pa., and SIMULIA (Abaqus) software products from Dassault Systèmes of Waltham, Mass.

Optionally, one or more appliance geometries and material compositions can be selected for testing or force modeling. As noted above, a desired tooth movement, as well as a force system required or desired for eliciting the desired tooth movement, can be identified. Using the simulation environment, a candidate appliance geometry and composition can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

Optionally, step 3830 can further involve determining the geometry of one or more auxiliary components to be used in combination with the orthodontic appliance in order to exert the force system on the one or more teeth. Such auxiliaries can include one or more of tooth-mounted attachments, elastics, wires, springs, bite blocks, arch expanders, wire-and-bracket appliances, shell appliances, headgear, or any other orthodontic device or system that can be used in conjunction with the orthodontic appliances herein. The use of such auxiliary components may be advantageous in situations where it is difficult for the appliance alone to produce the force system. Additionally, auxiliary components can be added to the orthodontic appliance in order to provide other desired functionalities besides producing the force system, such as mandibular advancement splints to treat sleep apnea, pontics to improve aesthetic appearance, and so on. In some embodiments, the auxiliary components are fabricated and provided separately from the orthodontic appliance. Alternatively, the geometry of the orthodontic appliance can be modified to include one or more auxiliary components as integrally formed components (see, e.g., FIGS. 16-36).

In step 3840, instructions for fabrication of the orthodontic appliance having the appliance geometry and material composition are generated. The instructions can be configured to control a fabrication system or device in order to produce the orthodontic appliance with the specified appliance geometry and material composition. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. Optionally, the instructions can be configured to cause a fabrication machine to directly fabricate the orthodontic appliance with variable properties, integrally formed components and/or power arms, as discussed above and herein. In alternative embodiments, the instructions can be configured for indirect fabrication of the appliance, e.g., by thermoforming.

Although the above steps show a method 3800 of designing an orthodontic appliance in accordance with some embodiments, a person of ordinary skill in the art will recognize some variations based on the teaching described herein. Some of the steps may comprise sub-steps. Some of the steps may be repeated as often as desired. One or more steps of the method 200 may be performed with any suitable fabrication system or device, such as the embodiments described herein. Some of the steps may be optional, and the order of the steps can be varied as desired. For instance, in some embodiments, step 3820 is optional, such that step 3830 involves determining the appliance geometry and/or material composition based directly on the tooth movement path rather than based on the force system.

Figure 39:
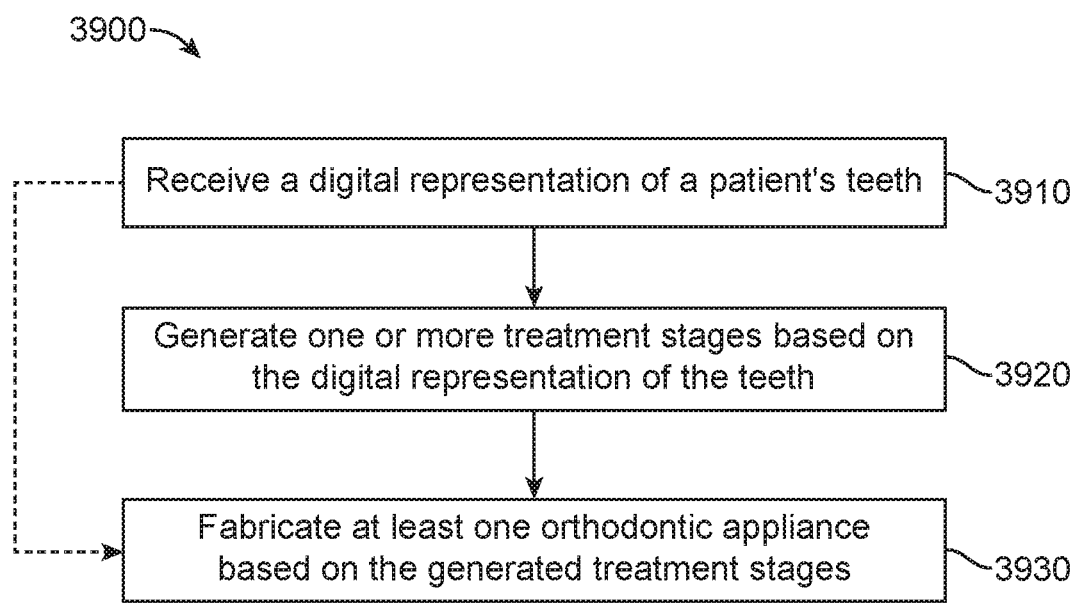
FIG. 39 illustrates a method for digitally planning an orthodontic treatment, in accordance with embodiments.

FIG. 39 illustrates a method 3900 for digitally planning an orthodontic treatment and/or design or fabrication of an appliance, in accordance with embodiments. The method 3900 can be applied to any of the treatment procedures described herein and can be performed by any suitable data processing system.

In step 3910, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step 3920, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step 3930, at least one orthodontic appliance is fabricated based on the generated treatment stages. For example, a set of appliances can be fabricated, each shaped according to a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 39, design and/or fabrication of an orthodontic appliance, and perhaps a particular orthodontic treatment, may include use of a representation of the patient's teeth (e.g., receive a digital representation of the patient's teeth 3910), followed by design and/or fabrication of an orthodontic appliance based on a representation of the patient's teeth in the arrangement represented by the received representation.

Optionally, some or all of the steps of the method 3900 are performed locally at the site where the patient is being treated and during a single patient visit, referred to herein as "chair side manufacturing." Chair side manufacturing can involve, for example, scanning the patient's teeth, automatically generating a treatment plan with treatment stages, and immediately fabricating one or more orthodontic appliance(s) to treat the patient using a chair side direct fabrication machine, all at the treating professional's office during a single appointment. In embodiments where a series of appliances are used to treat the patient, the first appliance may be produced chair side for immediate delivery to the patient, with the remaining appliances produced separately (e.g., off site at a lab or central manufacturing facility) and delivered at a later time (e.g., at a follow up appointment, mailed to the patient). Alternatively, the methods herein can accommodate production and immediate delivery of the entire series of appliances on site during a single visit. Chair side manufacturing can thus improve the convenience and speed of the treatment procedure by allowing the patient to immediately begin treatment at the practitioner's office, rather than having to wait for fabrication and delivery of the appliances at a later date. Additionally, chair side manufacturing can provide improved flexibility and efficiency of orthodontic treatment. For instance, in some embodiments, the patient is re-scanned at each appointment to determine the actual positions of the teeth, and the treatment plan is updated accordingly. Subsequently, new appliances can be immediately produced and delivered chair side to accommodate any changes to or deviations from the treatment plan.

Figure 40:
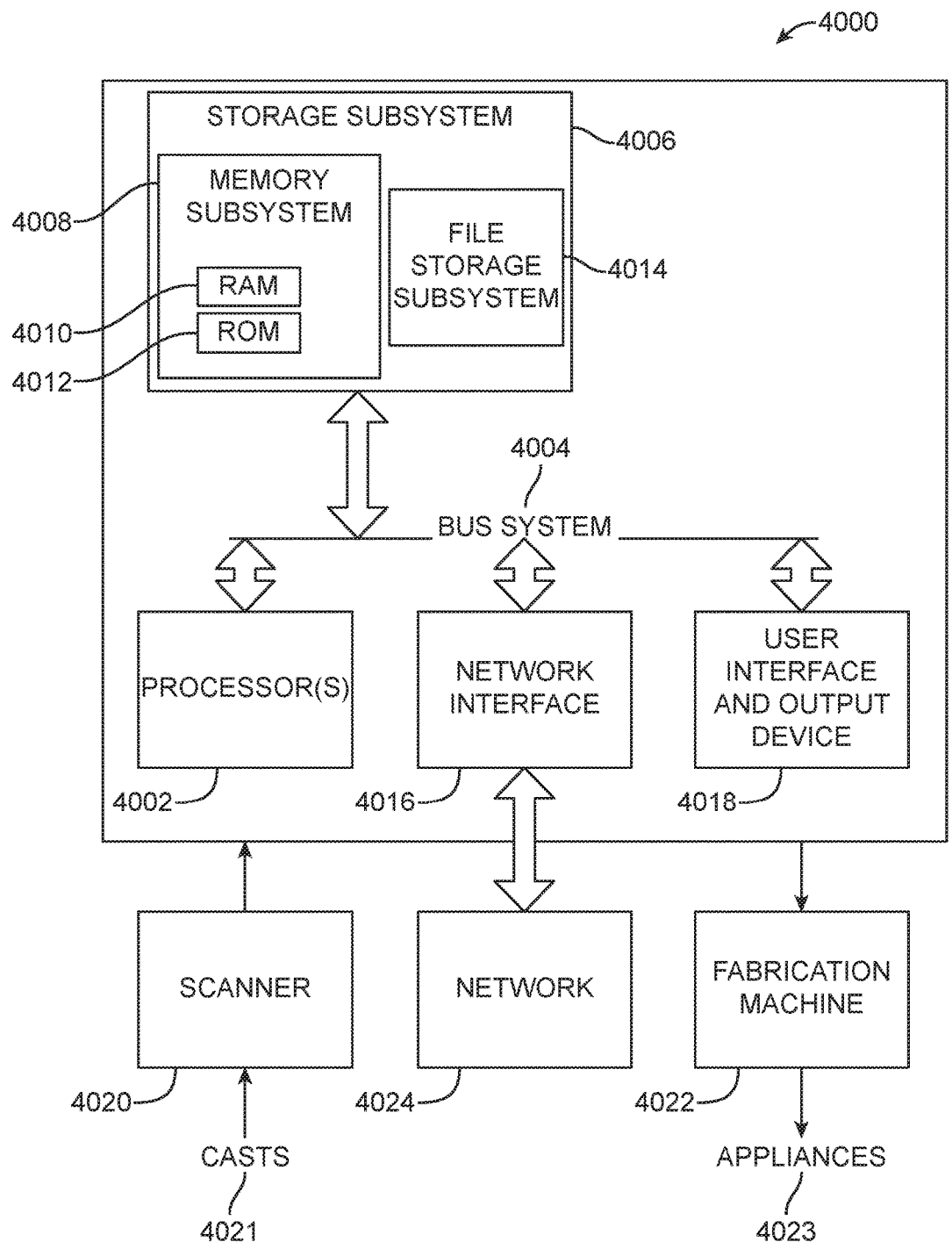
FIG. 40 is a simplified block diagram of a data processing system, in accordance with embodiments.

FIG. 40 is a simplified block diagram of a data processing system 4000 that may be used in executing methods and processes described herein. The data processing system 4000 typically includes at least one processor 4002 that communicates with one or more peripheral devices via bus subsystem 4004. These peripheral devices typically include a storage subsystem 4006 (memory subsystem 4008 and file storage subsystem 4014), a set of user interface input and output devices 4018, and an interface to outside networks 4016. This interface is shown schematically as "Network Interface" block 4016, and is coupled to corresponding interface devices in other data processing systems via communication network interface 4024. Data processing system 4000 can include, for example, one or more computers, such as a personal computer, workstation, mainframe, laptop, and the like.

The user interface input devices 4018 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 4006 maintains the basic required programming, including computer readable media having instructions (e.g., operating instructions, etc.), and data constructs. The program modules discussed herein are typically stored in storage subsystem 4006. Storage subsystem 4006 typically includes memory subsystem 4008 and file storage subsystem 4014. Memory subsystem 4008 typically includes a number of memories (e.g., RAM 4010, ROM 4012, etc.) including computer readable memory for storage of fixed instructions, instructions and data during program execution, basic input/output system, etc. File storage subsystem 4014 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 4020 includes any means for obtaining a digital representation (e.g., images, surface topography data, etc.) of a patient's teeth (e.g., by scanning physical models of the teeth such as casts 4021, by scanning impressions taken of the teeth, or by directly scanning the intraoral cavity), which can be obtained either from the patient or from treating professional, such as an orthodontist, and includes means of providing the digital representation to data processing system 4000 for further processing. Scanner 4020 may be located at a location remote with respect to other components of the system and can communicate image data and/or information to data processing system 4000, for example, via a network interface 4024. Fabrication system 4022 fabricates appliances 4023 based on a treatment plan, including data set information received from data processing system 4000. Fabrication machine 4022 can, for example, be located at a remote location and receive data set information from data processing system 4000 via network interface 4024.

The data processing aspects of the methods described herein can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing steps can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. An appliance for placement on teeth of a patient, the appliance comprising:
    a plurality of power arms comprising a first power arm having a first connection point for connecting to a shell or tooth and a second power arm having a second connection point for connecting to a shell or tooth;
    a connecting structure coupled to the first and second power arms to apply a first force to each of the first and second power arms; and
    a counter-force connector coupled to the first power arm and extending toward the second power arm to apply a second force to each of the first and second power arms opposing the first force when engaging the second power arm,
    wherein the connecting structure and the counter-force connector are coupled to the first power arm at respective locations separate from the first connection point, the connecting structure is coupled to the second power arm at a location separate from the second connection point, and the counter-force connector, when engaging the second power arm, contacts the second power arm at a location separate from the second connection point.

2. The appliance of claim 1, wherein the connecting structure comprises a rest length and the counter-force connector comprises a length different than the rest length of the connecting structure.

3. The appliance of claim 1, wherein the length of the counter-force connector is shorter than the rest length of the connecting structure such that the connecting structure is compressed when the counter-force connector engages the second power arm.

4. The appliance of claim 1, wherein the length of the counter-force connector is longer than the rest length of the connecting structure such that the connecting structure is stretched when the counter-force connector engages the second power arm.

5. The appliance of claim 1, wherein the connecting structure is an elastic spring structure.

6. The appliance of claim 1, wherein the first and second power arms each comprise an attachment structure for bonding to a surface of a respective tooth at the first and second connection points.

7. The appliance of claim 1, further comprising a shell comprising a plurality of tooth-receiving cavities, wherein the first and second power arms are coupled to the shell at the respective connection points.

8. The appliance of claim 7, wherein the plurality of power arms is integrally formed with the shell by direct fabrication.

9. The appliance of claim 1, wherein the first and second power arms are integrally formed with one or more of the connecting structure and the counter-force connector by direct fabrication.

10. A method for treating a patient's teeth, the method comprising:
placing the appliance of claim 1 on the patient's teeth; and
removing the counter-force connector from the appliance, such that the first force applied by the connecting structure to the plurality of power arms is transmitted to the patient's teeth.

* * * * *